(12) United States Patent
Secrist, III et al.

(10) Patent No.: US 8,637,485 B2
(45) Date of Patent: Jan. 28, 2014

(54) 5',-SUBSTITUTED ADENOSYNES PREPARATION THEREOF AND USE AS INHIBITORS OF S-ADENOSYLMETHIONINE DECARBOXYLASE

(75) Inventors: John A. Secrist, III, Birmingham, AL (US); Steven Ealick, Ithaca, NY (US); Shridhar Bale, Ithaca, NY (US); Anthony E. Pegg, Hershey, PA (US); Diane E. McCloskey, Hershey, PA (US); Wayne C. Guida, St. Pete Beach, FL (US)

(73) Assignees: Southern Research Institute, Birmingham, AL (US); Cornell University, Ithica, NY (US); H. Lee Moffitt Cancer and Research Institute, Tampa, FL (US); The Penn State Research Foundation, University Park, PA (US)

( * ) Notice: Subject to any disclaimer, the term of this patent is extended or adjusted under 35 U.S.C. 154(b) by 408 days.

(21) Appl. No.: 12/671,121

(22) PCT Filed: Aug. 1, 2008

(86) PCT No.: PCT/US2008/071999
§ 371 (c)(1),
(2), (4) Date: Sep. 27, 2010

(87) PCT Pub. No.: WO2009/018541
PCT Pub. Date: Feb. 5, 2009

(65) Prior Publication Data
US 2011/0009354 A1 Jan. 13, 2011

Related U.S. Application Data

(60) Provisional application No. 60/953,621, filed on Aug. 2, 2007.

(51) Int. Cl.
*A61K 31/70* (2006.01)
*C07H 19/167* (2006.01)
*C07H 19/173* (2006.01)

(52) U.S. Cl.
USPC .......... 514/46; 536/27.62; 536/27.8

(58) Field of Classification Search
None
See application file for complete search history.

(56) References Cited

U.S. PATENT DOCUMENTS

| 4,794,174 | A | 12/1988 | Secrist, III |
| 5,416,076 | A | 5/1995 | Casara et al. |
| 2004/0059104 | A1 | 3/2004 | Cook et al. |
| 2010/0261668 | A1* | 10/2010 | Xiang et al. .......... 514/46 |

OTHER PUBLICATIONS

Wolff, Manfred E. "Burger's Medicinal Chemistry, 5ed, Part I", John Wiley & Sons, 1995, pp. 975-977.*
Banker, G.S. et al, "Modern Pharmaceutics, 3ed.", Marcel Dekker, New York, 1996, pp. 451 and 596.*
Pegg et al., Biochemistry, 1986, vol. 25(14), 4091-97.*
Bhatnagar et al., Biochemistry, 1983, 22, pp. 6310-6317.*

* cited by examiner

*Primary Examiner* — Traviss C McIntosh, III
(74) *Attorney, Agent, or Firm* — Novak Druce Connolly Bove + Quigg LLP

(57) ABSTRACT

The crystal structure of the complex of S-adenosylmethionine methyl ester with hAdoMetDC F223A, a mutant where the stacking of the aromatic rings of F7, adenine and F223 would be eliminated. The structure of this mutant with the ester shows that the ligand still maintains a syn conformation aided by pi-pi interactions to F7, hydrogen bonds to the backbone of Glu67, and electrostatic interactions. Several series of AdoMet substrate analogues with a variety of substituents at the 8 position of adenine were synthesized and analyzed for their ability to inhibit hAdoMetDC. To understand these results, virtual modeling of the enzyme inhibitor complexes and the crystal structures of human AdoMetDC with 5'-deoxy-5'-[N-methyl-N-[2-(aminooxy)ethyl]amino-8-methyl]adenosine (MAOEMA) and 5'-deoxy-5'-[N-methyl-N-[4-(aminooxy)butyl]amino-8-ethyl]adenosine (MAOBEA) at the active site have been determined experimentally.

19 Claims, 5 Drawing Sheets

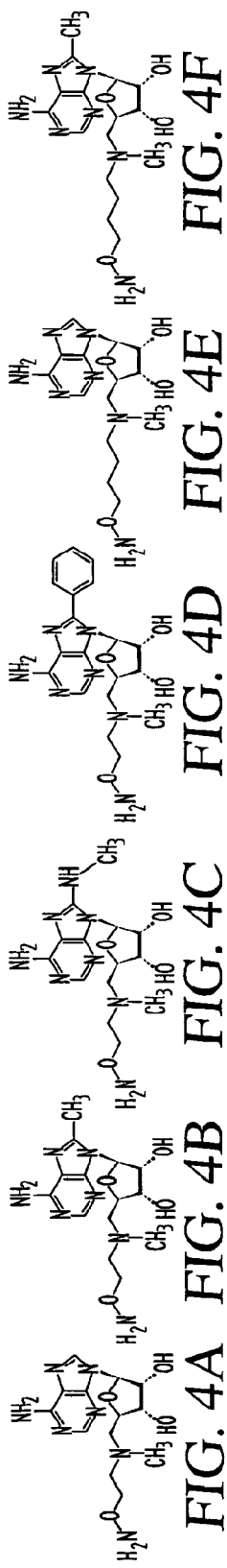
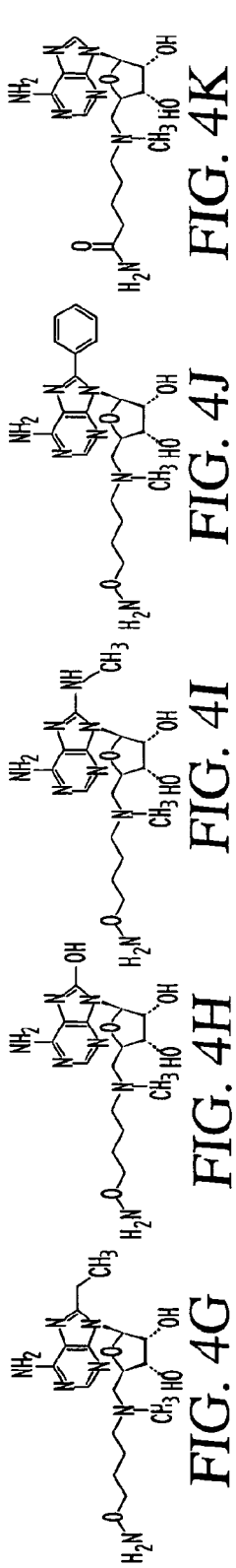
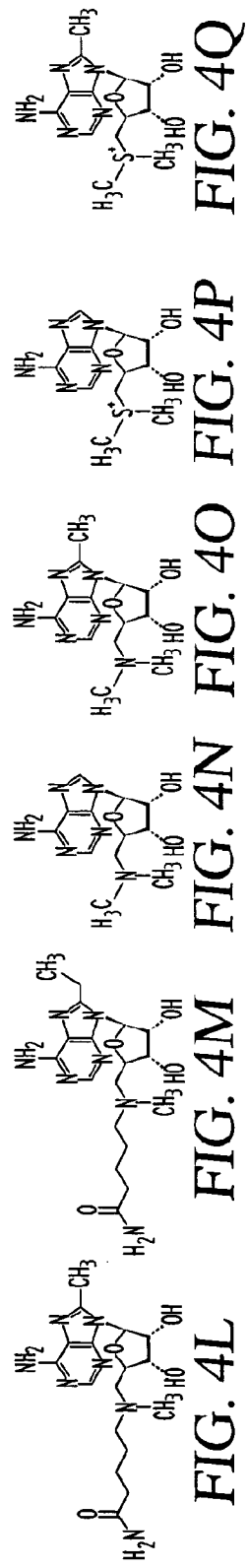
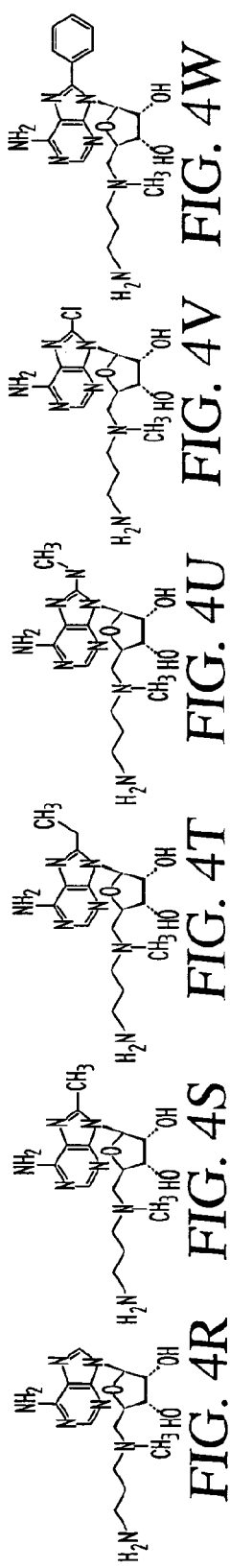
FIG. 4A  FIG. 4B  FIG. 4C  FIG. 4D  FIG. 4E  FIG. 4F
FIG. 4G  FIG. 4H  FIG. 4I  FIG. 4J  FIG. 4K
FIG. 4L  FIG. 4M  FIG. 4N  FIG. 4O  FIG. 4P  FIG. 4Q
FIG. 4R  FIG. 4S  FIG. 4T  FIG. 4U  FIG. 4V  FIG. 4W

5',-SUBSTITUTED ADENOSYNES PREPARATION THEREOF AND USE AS INHIBITORS OF S-ADENOSYLMETHIONINE DECARBOXYLASE

CROSS REFERENCE TO RELATED APPLICATIONS

This application is a National Phase filing under 35 U.S.C. §371 of PCT/US2008/071999 filed Aug. 1, 2008, which claims priority to U.S. Patent Application No. 60/953,621, filed on Aug. 2, 2007. The entire contents of each of the above-applications are incorporated herein by reference.

STATEMENT REGARDING FEDERALLY SPONSORED RESEARCH OR DEVELOPMENT

This invention was made using funds provided under PO1 CA-94000 from National Cancer Institute and the Biomedical Research Resource Program (RR-01646) of the National Institutes of Health and the U.S. government has certain rights in the invention.

TECHNICAL FIELD

The present disclosure relates to certain adenine derivatives and particularly to certain 5'-substituted adenosine compounds. The present disclosure is also related to use of the adenine derivatives as inhibitors of S-adenosylmethionine decarboxylase. The present disclosure also relates to use of the adenine derivatives to treat various maladies such as cancers and parasitic infections and especially in a mammal. The present disclosure is also concerned with processes for preparing the disclosed compounds.

BACKGROUND ART

S-Adenosylmethionine decarboxylase is a critical enzyme in the polyamine biosynthetic pathway and depends on a pyruvoyl group for the decarboxylation process. Inhibitors of this enzyme have potential as cancer chemotherapeutic drugs and for treating various parasitic infections. The crystal structures of the enzyme with various inhibitors at the active site have been determined previously and have shown that the adenine base of the ligands adopts an unusual syn conformation during interaction with the enzyme. For example, it is known that 8-substitution on adenine rings causes the nucleotide to adopt a syn conformation in solution (37-40). In the syn conformation, the adenine base stacks between the F223 and F7 residues of AdoMetDC. S-Adenosylmethionine decarboxylase (AdoMetDC) is a pyruvoyl dependent decarboxylase and a critical enzyme in the polyamine biosynthetic pathway which is found in all species (1-4). The polyamines putrescine, spermidine and spermine are essential for cell growth and play an important role in cell proliferation and differentiation (5-7). Polyamines have been found to be elevated in various types of cancer including non small cell lung cancer, prostate cancer, melanoma, and pancreatic cancer (8, 9). Polyamine levels in cells depend on the polyamine synthetic and catabolic pathways as well as on import and export of polyamines across the cellular membrane. Altering regulation of the key enzymes in the polyamine pathway is a therapeutic strategy for treatment of various types of cancers. AdoMetDC catalyzes the conversion of S-adenosylmethionine (AdoMet) to decarboxylated-S-adenosylmethionine (dcAdoMet), which then donates the aminopropyl group to putrescine or spermidine to form spermidine and spermine, respectively. AdoMetDC is at a key branch point in the pathway and its action commits AdoMet to polyamine biosynthesis and removes it from the pool available for methyl donation.

Attempts to regulate polyamine levels, have resulted in the development of inhibitors that target the biosynthetic enzymes ornithine decarboxylase (ODC) (10), AdoMetDC and the catabolic enzyme spermidine/spermine $N^1$-acetyl-transferase (SSAT) (11). The best-known inhibitor of ODC is α-difluoromethylornithine (DFMO) which irreversibly inactivates the enzyme. The success of DFMO in cancer therapy has been limited as the cells compensate for the decreased synthesis of polyamines through increased cellular uptake of polyamines (12). DFMO is currently being investigated as a chemopreventive agent against carcinogenesis (13-15). The development of drugs to inhibit AdoMetDC started with the competitive inhibitor methylglyoxal bis(guanylhydrazone) (MGBG) which is similar to spermidine in structure (16). Use of MGBG caused extreme toxicity in humans and many analogues of MGBG were developed in attempts to decrease the toxicity. One such AdoMet inhibitor that resulted was 4-amidinoindan-1-one-2'-amidinohydrazone (CGP48664A) which has gone on to clinical trials as a cancer chemotherapeutic agent (17). Alternately, inhibitors like MHZPA, MAOEA and MHZEA that are structural analogues of the natural substrate were developed. These compounds inactivate AdoMetDC by forming a Schiff base to the active site pyruvoyl group (18). Another known nucleoside inhibitor of AdoMetDC is 5'-(18)-5'-deoxyadenosine. This was designed as an enzyme-activated irreversible inhibitor (19) but subsequent experiments showed that it acted via by a transamination of the pyruvate prosthetic group (18).

The crystal structure of AdoMetDC and its S68A and H243A mutants were solved to understand the mechanisms of decarboxylation and autoprocessing (20-22). The crystal structures of AdoMetDC with inhibitors like MAOEA, MHZPA and MeAdoMet have been solved previously (23). These structures show that the adenine base of the inhibitors assumes an unusual syn conformation in the active site.

SUMMARY OF DISCLOSURE

It has been found according to this disclosure that certain adenine analogues result in ligands which favor the syn conformation in solution. The synthesis of several series of structural analogues of AdoMet with 8-substituted as well as unsubstituted adenine (i.e. the 8 substituent being H) and analysis of their abilities to inhibit AdoMetDC are disclosed herein. The crystal structures of the AdoMetDC F223A mutant complexed with MeAdoMet and the wild-type protein complexed with the inhibitors 5'-deoxy-5'-[N-methyl-N-[2-(aminooxy)ethyl]amino-8-methyl]adenosine (MAOEMA) and 5'-deoxy-5'-[N-methyl-N-[4-(aminooxy)butyl]amino-8-ethyl]adenosine (MAOBEA) are also disclosed. For convenience, the following abbreviations are used herein. AdoMetDC, S-adenosylmethionine decarboxylase; AdoMet, S-adenosylmethionine; MAOEMA, 5'-Deoxy-5'-[N-methyl-N-[4-(aminooxy)ethyl]amino-8-methyl]adenosine; MAOBEA, 5'-Deoxy-5'-[N-methyl-N-[4-(aminooxy)butyl]amino-8-ethyl]adenosine; MeAdoMet, methyl ester of S-adenosylmethionine; Tris, tris(hydroxymethyl)aminomethane; PEG, poly(ethylene glycol); CCD, charge-coupled device; MGBG, methylglyoxal bis(guanylhydrazone); CGP48664A, 4-amidinoindan-1-one-2'-amidinohydrazone; MAOEA, 5'-deoxy-5'-[N-methyl-N-[(2-aminooxy)ethyl]amino]adenosine; MHZPA, 5'-deoxy-5'-[N-methyl-N-(3-hydrazinopropyl)amino]adenosine; Hepes, N-(2-hydroxyethyl)piperazine-N'-2-ethanesulfonic acid; IPTG, isopropyl-1-thio-β-D-galactopyranoside; DTT, dithiothreitol; EDTA, ethylenediaminetetraacetic acid.

In particular, the present disclosure is concerned with compounds represented by the formula:

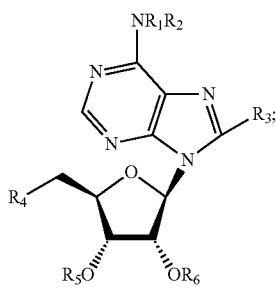

pharmaceutically acceptable salt thereof; solvate thereof, and prodrug thereof; wherein each of $R_1$ and $R_2$ individually is selected from the group consisting of H and alkyl; $R_3$ is selected from the group consisting of H, alkyl, $NR_1R_2$, $OR_1R_2$, aryl, heteroaryl, halo, and $CF_3$; $R_4$ is selected from the group consisting of $NR_7R_8$ and $SR_1R_2$; each of $R_7$ and $R_8$ individually is selected from the group consisting of H, alkyl, $(CH_2)_nNR_1R_2$, $(CH_2)_nCONR_1R_2$ and $(CH_2)_nC=ONR_1R_2$; wherein n is a whole number integer from 1 to 8; and each of $R_5$ and $R_6$ individually is selected from the group consisting of H and acyl.

The present disclosure is also concerned with pharmaceutical compositions comprising an effective amount of a compound or pharmaceutically acceptable salt thereof, or a solvate thereof, or prodrug thereof as disclosed above and a pharmaceutically acceptable carrier.

A further aspect of the present invention relates to inhibiting S-adenosylmethionine decarboxylase in a host in need thereof which comprises administering to said host an effective amount of a compound; pharmaceutically acceptable salt thereof solvate thereof, or prodrug thereof as described above.

A still further aspect of the present invention is concerned with treating a host suffering from a parasitic infection or infection caused by *Pneumocystis cainii*.

Still other objects and advantages of the present disclosure will become readily apparent by those skilled in the art from the following detailed description, wherein it is shown and described preferred embodiments, simply by way of illustration of the best mode contemplated. As will be realized the disclosure is capable of other and different embodiments, and its several details are capable of modifications in various obvious respects, without departing from the disclosure. Accordingly, the description is to be regarded as illustrative in nature and not as restrictive.

SUMMARY OF DRAWINGS

FIG. 4 shows structures of potential inhibitors of hAdoMetDC.

BEST AND VARIOUS MODES FOR CARRYING OUT DISCLOSURE

Figure 1A:
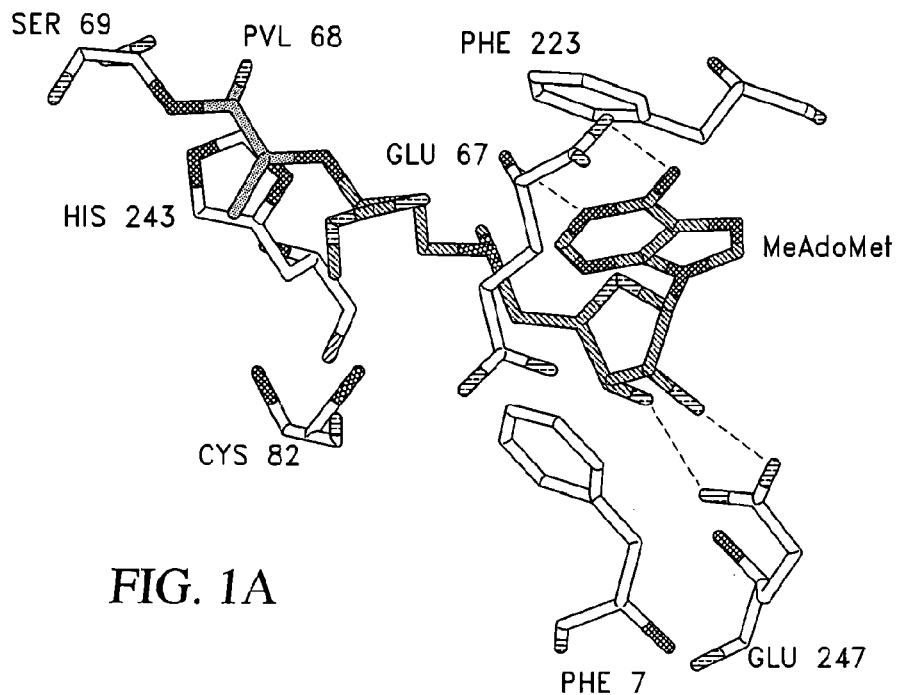
FIG. 1A illustrates the actual crystal structure of hAdoMetDC with MeAdoMet in the active site.

The present disclosure is concerned with compounds represented by the following formula:

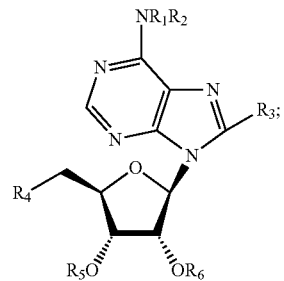

pharmaceutically acceptable salt thereof; solvate thereof, and prodrug thereof; wherein each of $R_1$ and $R_2$ individually is selected from the group consisting of H and alkyl; $R_3$ is selected from the group consisting of H, alkyl, $NR_1R_2$, $OR_1R_2$, aryl, heteroaryl, halo, and $CF_3$; $R_4$ is selected from the group consisting of $NR_7R_8$ and $SR_1R_2$; each of $R_7$ and $R_8$ individually is selected from the group consisting of H, alkyl, $(CH_2)_nNR_1R_2$, $(CH_2)_nCONR_1R_2$ and $(CH_2)_nC=ONR_1R_2$; wherein n is a whole number integer from 1 to 8; and each of $R_5$ and $R_6$ individually is selected from the group consisting of H and acyl.

Listed below are definitions of various terms used to describe this disclosure. These definitions apply to the terms as they are used throughout this specification, unless otherwise limited in specific instances, either individually or as part of a larger group. Also, in the formula described and claimed herein, it is intended that when any symbol appears more than once in a particular formula or substituent, its meaning in each instance is independent of the other.

"Effective amount" refers to an amount of a compound as described herein that may be therapeutically effective to enhance the efficacy of a pharmacological agent The precise amount of these compounds required will vary with the particular compounds or derivatives employed, the age and condition of the subject to be treated, and the nature and severity of the condition. However, the effective amount may be determined by one of ordinary skill in the art once aware of this disclosure without undue experimentation.

"Pharmaceutically acceptable" refers to those compounds, materials, compositions, and/or dosage forms which are, within the scope of sound medical judgment, suitable for contact with the tissues of human beings and animals without excessive toxicity, irritation, allergic response, or other problem complications commensurate with a reasonable benefit/ risk ratio.

"Pharmaceutically acceptable salts" refer to derivatives of the disclosed compounds wherein the parent compound is modified by making acid or base salts thereof. Examples of pharmaceutically acceptable salts include, but are not limited to, mineral or organic acid salts of basic residues such as amines; alkali or organic salts of acidic residues such as carboxylic acids; and the like. The pharmaceutically acceptable salts include the conventional non-toxic salts or the quaternary ammonium salts of the parent compound formed, for example, from non-toxic inorganic or organic acids. Typical inorganic acids used to form such salts include hydrochloric, hydrobromic, hydroiodic, nitric, sulfuric, phosphoric, hypophosphoric and the like. Salts derived from organic acids, such as aliphatic mono and dicarboxylic acids, phenyl substituted alkonic acids, hydroxyalkanoic and hydroxyalkandioic acids, aromatic acids, aliphatic and aromatic sulfonic acids, may also be used. Such pharmaceutically acceptable salts thus include acetate, phenylacetate, trifluoroacetate, acrylate, ascorbate, benzoate, chlorobenzoate, dinitrobenzoate, hydroxybenzoate, methoxybenzoate, methylbenzoate, o-acetoxybenzoate, naphthalene-2-benzoate, bromide, isobutyrate, phenylbutyrate, β-hydroxybutyrate, butyne-1,4-dioate, hexyne-1,4-dioate, cabrate, caprylate, chloride, cinnamate, citrate, formate, fumarate, glycollate, heptanoate, hippurate, lactate, malate, maleate, hydroxymaleate, malonate, mandelate, mesylate, nicotinate, isonicotinate, nitrate, oxalate, phthalate, teraphthalate, phosphate, monohydrogenphosphate, dihydrogenphosphate, metaphosphate, pyrophosphate, propiolate, propionate, phenylpropionate, salicylate, sebacate, succinate, suberate, sulfate, bisulfate, pyrosulfate, sulfite, bisulfite, sulfonate, benzene-sulfonate, p-bromobenzenesulfonate, chlorobenzenesulfonate, ethanesulfonate, 2-hydroxyethanesulfonate, methanesulfonate, naphthalene-1-sulfonate, naphthalene-2-sulfonate, p-toleunesulfonate, xylenesulfonate, tartarate, and the like.

Bases commonly used for formation of salts include ammonium hydroxide and alkali and alkaline earth metal hydroxides, carbonates, as well as aliphatic and primary, secondary and tertiary amines, aliphatic diamines. Bases especially useful in the preparation of addition salts include sodium hydroxide, potassium hydroxide, ammonium hydroxide, potassium carbonate, methylamine, diethylamine, and ethylene diamine.

A "Prodrug" is a compound that is converted within the body into its active form that has a medical effect. Prodrugs may be useful when the active drug may be too toxic to administer systemically, the active drug is absorbed poorly by the digestive tract, or the body breaks down the active drug before it reaches its target. Methods of making prodrugs are disclosed in Hans Bundgaard, *Design of Prodrugs* (Elsevier Science Publishers B.V. 1985), which is incorporated herein by reference in its entirety.

Prodrug forms of the compounds bearing various nitrogen functions (amino, hydroxyamino, hydrazino, guanidino, amidino, amide, etc.) may include the following types of derivatives where each R group individually may be hydrogen, substituted or unsubstituted alkyl, aryl, alkenyl, alkynyl, heterocycle, alkylaryl, aralkyl, aralkenyl, aralkynyl, cycloalkyl or cycloalkenyl groups as defined above.

Carboxamides, —NHC(O)R
Carbamates, —NHC(O)OR
(Acyloxy)alkyl Carbamates, NHC(O)OROC(O)R
Enamines, —NHCR(=CHCRO$_2$R) or —NHCR(=CH-CRONR$_2$)
Schiff Bases, —N=CR$_2$
Mannich Bases (from carboximide compounds), RCONHCH$_2$NR$_2$ Preparations of such prodrug derivatives are discussed in various literature sources (examples are: Alexander et al., *J. Med. Chem.* 1988, 31, 318; Aligas-Martin et al., PCT WO pp/41531, p. 30). The nitrogen function converted in preparing these derivatives is one (or more) of the nitrogen atoms of a compound of the invention.

Prodrug forms of carboxyl-bearing compounds of the disclosure include esters (—CO$_2$R) where the R group corresponds to any alcohol whose release in the body through enzymatic or hydrolytic processes would be at pharmaceutically acceptable levels.

Another prodrug derived from a carboxylic acid form of the disclosure may be a quaternary salt type

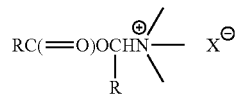

of structure described by Bodor et al., *J. Med. Chem.* 1980, 23, 469.

It is of course understood that the compounds of the present disclosure relate to all optical isomers and stereo-isomers at the various possible atoms of the molecule unless specified.

"Solvates" refers to the compound formed by the interaction of a solvent and a solute and includes hydrates. Solvates are usually crystalline solid adducts containing solvent molecules within the crystal structure, in either stoichiometric or non-stoichiometric proportions.

The term "halogen" or "halo" refers to fluorine, chlorine, bromine and iodine.

The term "aryl" refers to monocyclic or bicyclic aromatic hydrocarbon groups having 6 to 12 carbon atoms in the ring portion, such as phenyl, naphthyl, biphenyl and diphenyl groups, each of which may be substituted. The aromatic or aryl groups are more typically phenyl and alkyl substituted aromatic groups (aralkyl) such as phenyl C$_{1-3}$ alkyl and benzyl.

The term "aralkyl" or "alkylaryl" or "alaryl" refers to an aryl group bonded directly through an alkyl group, such as benzyl or phenethyl.

The term "substituted aryl" or "substituted alkylaryl" refers to an aryl group or alkylaryl group substituted by, for example, one to four substituents such as alkyl; substituted alkyl, halo and alkoxy. "Substituted benzyl" refers to a benzyl group substituted by, for example, any of the groups listed above for substituted aryl.

The term "alkyl" refers to straight or branched chain unsubstituted hydrocarbon groups of 1 to 20 carbon atoms, and more typically 1 to 8 carbon atoms and even more typically unsubstituted alkyl groups of 1 to 4 carbon atoms. Examples of suitable alkyl groups include methyl, ethyl and propyl. Examples of branched alkyl groups include isopropyl and t-butyl.

The term "heteroaryl", refers to an optionally substituted, unsaturated aromatic cyclic group, for example, which is a 4 to 7 membered monocyclic, 7 to 11 membered bicyclic, or 10 to 15 membered tricyclic ring system, which has at least one heteroatom and at least one carbon atom in the ring. Each ring of the heterocyclic group containing a heteroatom may have 1, 2 or 3 heteroatoms selected from nitrogen atoms, oxygen atoms and sulfur atoms, where the nitrogen and sulfur heteroatoms may also optionally be oxidized and the nitrogen heteroatoms may also optionally be quaternized. The heterocyclic group may be attached at any heteroatom or carbon atom. Examples of heteroaryls include, but are not limited to pyrrole, imidazole, pyrazole, pyridine, pyrazine, pyrimidine, pyridazine, indolizine, isoindole, indole, indazole, purine, quinoxaline, quinazoline, cinnoline, thiophene, furan and isopyrrole. The heteroaromatic moieties can be optionally substituted as described above for aryl, including substituted with one or more substituents selected from alkoxy, halo, and alkyl.
Typical aliphatic acyl groups contain 1 to 6 carbon atoms and include formyl, acetyl and propionyl.
Compounds according to the present invention can be prepared by the schemes that follow.
Scheme 1 presents the precursor nucleoside series 3 and 4 that were used along with their synthesis.
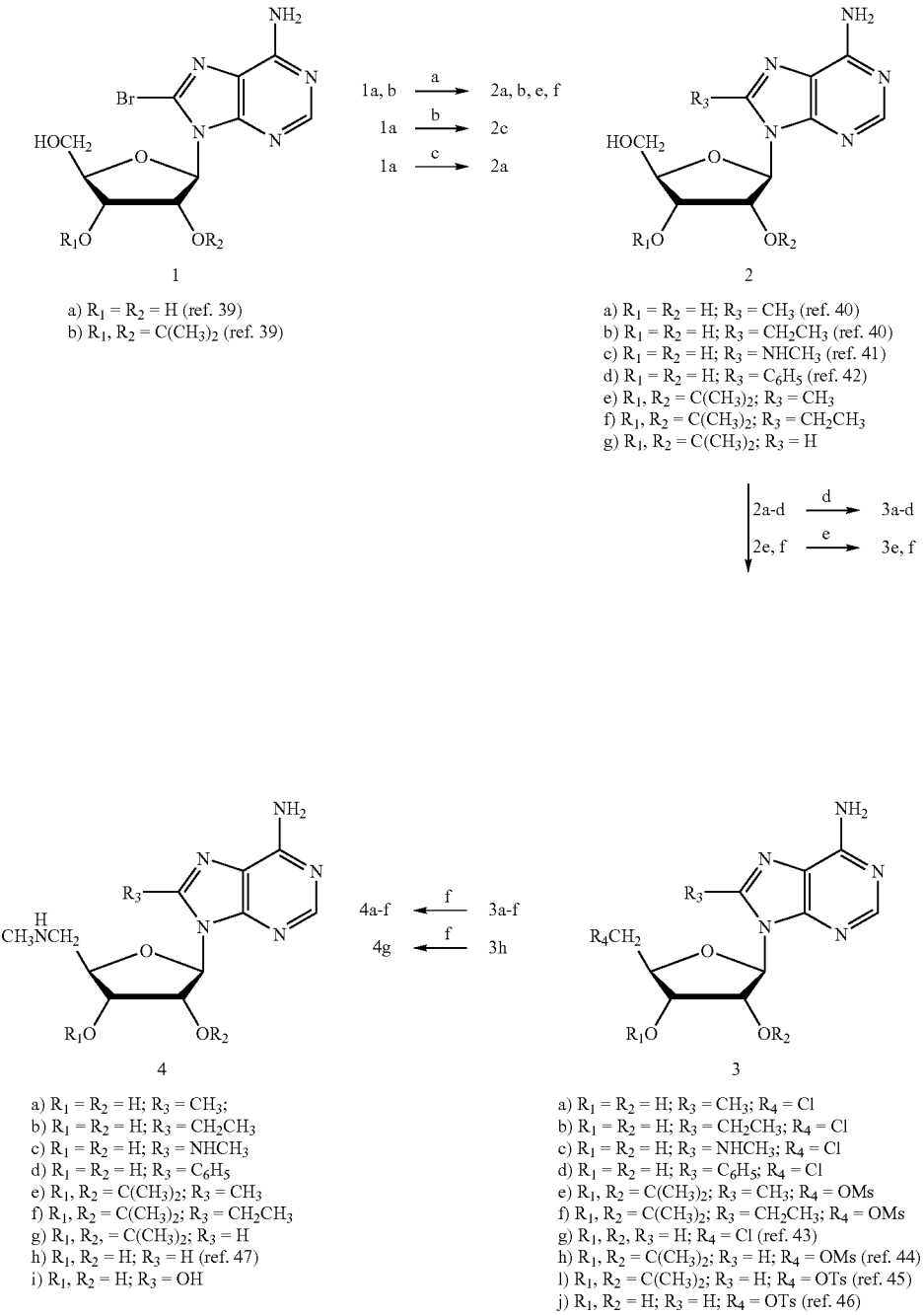

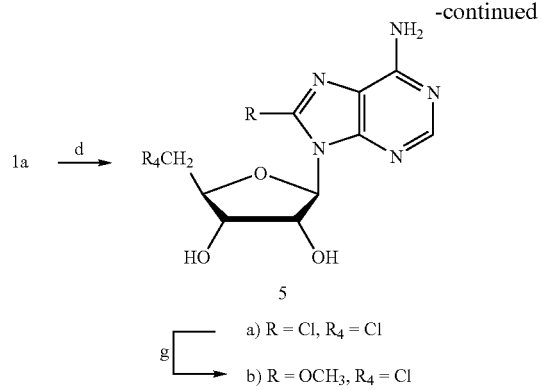

5
a) R = Cl, R$_4$ = Cl
b) R = OCH$_3$, R$_4$ = Cl

5b $\xrightarrow{f}$ 4l $^a$ (CH$_3$)$_4$Sn or (CH$_3$CH$_2$)$_4$Sn, HMDS/dioxane, NMP, (Ph$_3$P)$_4$Pd, 110° C.;
$^b$ CH$_3$NH$_2$, MeOH, 110° C.;
$^c$ C$_6$H$_5$B(OH)$_2$, K$_2$CO$_3$, (Ph$_3$P)$_4$Pd, 1,2-DME-H$_2$O (2:1), 90° C.;
$^d$ SOCl$_2$, CH$_3$CN/pyridine, 0° C. - RT, NH$_4$OH, RT;
$^e$ MsCl, pyridine, 0° C.;
$^f$ 33% CH$_3$NH$_2$, EtOH, RT (4e, f, g) or 90° C. (4a-d);
$^g$ NaOMe/MeOH, RT Target compounds with an aminooxyalkylamino side chain at C-5' were prepared using two different routes, as shown in Scheme 2. In the original sequence, which utilized a 2',3'-O-isopropylidene group for protection, the hydroxyalkylamino precursor 10 was generated by displacement of a tosyl group with the requisite amine. Using N-hydroxyphthalimide, triphenylphosphine and DEAD,[38] the aminooxy precursor 11 was produced and then converted to the desired target 12 under acidic conditions. Later it was found more effective to first generate the aminooxy precursors ethyl N-(2-bromoethoxy)ethanimidate[48] and ethyl N—(N-4-bromobutoxy)ethanimidate[49] (Scheme 2), which could be appended to C-5' by halide displacement with a 5'-methylamino-5'-deoxy-nucleoside to produce product series 6 and 8. Initially this displacement was carried out with an isopropylidene protecting group on the nucleoside. Subsequently it was determined that the reaction works as well or better without the protecting group. By the above means targets 7a-c and 9a-f were prepared.

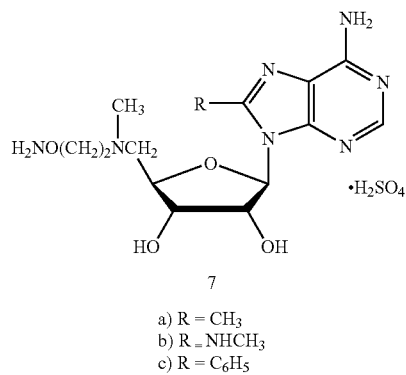

7
a) R = CH$_3$
b) R = NHCH$_3$
c) R = C$_6$H$_5$ 4c, d, e, f, g, l $\xrightarrow{c}$ Scheme 2

4a, c, d $\xrightarrow{a}$

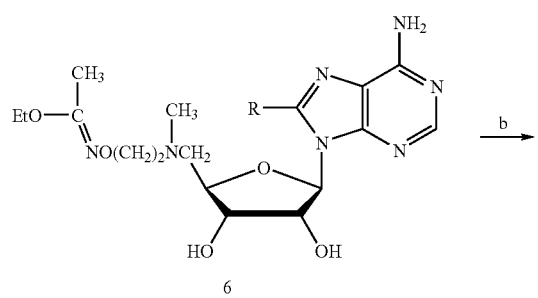

6
a) R = CH$_3$
b) R = NHCH$_3$
c) R = C$_6$H$_5$

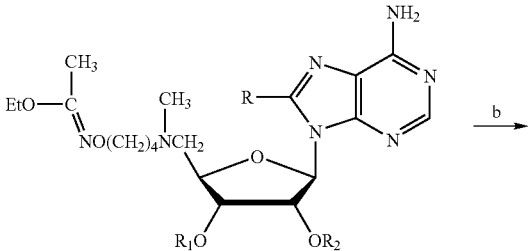

8
a) R$_1$, R$_2$ = H; R = NHCH$_3$
b) R$_1$, R$_2$ = H; R = C$_6$H$_5$
c) R$_1$, R$_2$ = H; R = OH
d) R$_1$, R$_2$ = C(CH$_3$)$_2$; R = CH$_3$
e) R$_1$, R$_2$ = C(CH$_3$)$_2$; R = CH$_2$CH$_3$
f) R$_1$, R$_2$ = C(CH$_3$)$_2$; R = H

-continued

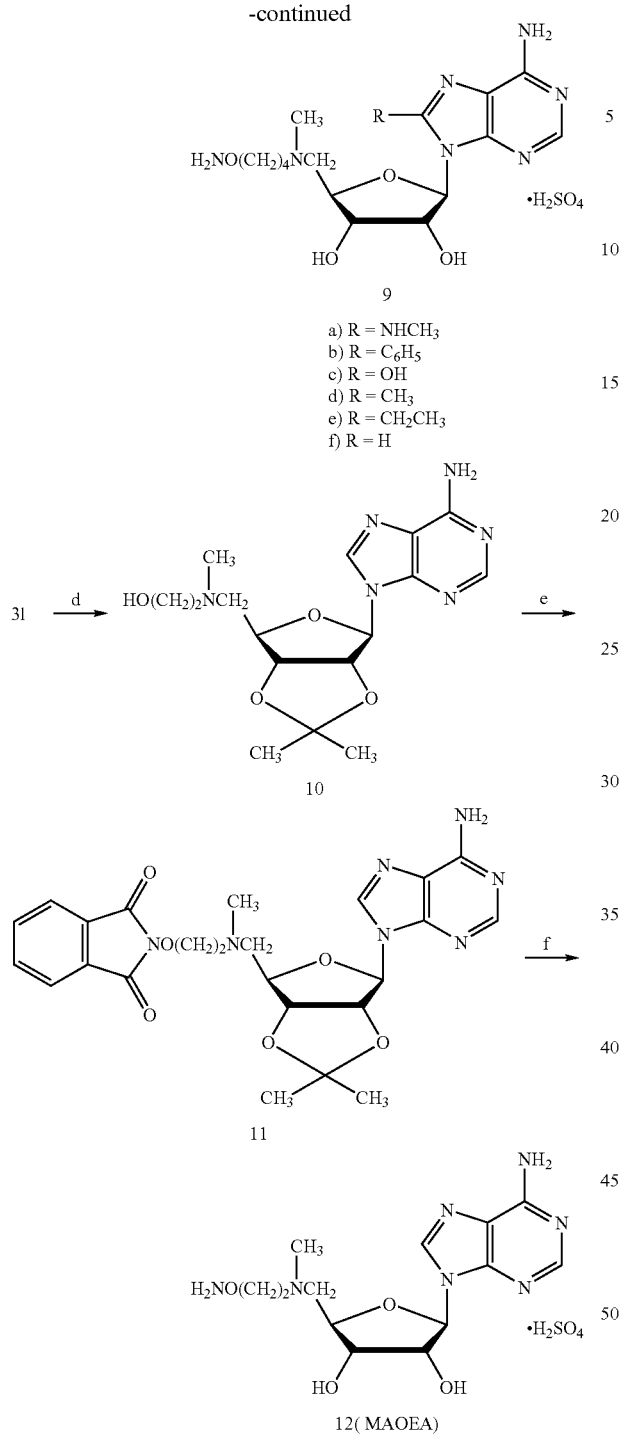

a) R = NHCH₃
b) R = C₆H₅
c) R = OH
d) R = CH₃
e) R = CH₂CH₃
f) R = H 12 (MAOEA)

$^a$ CH₃(OEt)C=NO(CH₂)₂Br (ref. 48), DMF, DIEA, 50° C.;
$^b$ 1N H₂SO₄, RT;
$^c$ CH₃(OEt)C=NO(CH₂)₄Br (ref. 49), DMF, DIEA, 50° C.;
$^d$ 2-(Methylaminoethanol), RT;
$^e$ N-Hydroxyphthalimide, PPh₃, DEAD, THF (ref. 38), RT;
$^f$ 1N H₂SO₄, 60° C.

All of the amides and hydrazides were made by similar procedures, as shown in Scheme 3. The 5'-methylamino-5'-deoxynucleosides were treated with the appropriate ω-chloroester followed by treatment with either ammonia or hydrazine. If an isopropylidene group was involved, then it was removed with an acidic deprotection step. In this manner targets 13d-f, j-m, with two different linker lengths and various 8-substituents, were prepared.

Scheme 3

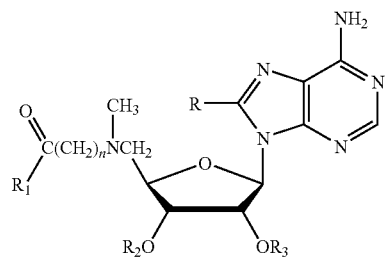

13 a) R = CH₃; R₁ = OEt; R₂, R₃ = H; n = 2
b) R = CH₂CH₃; R₁ = OEt; R₂, R₃ = H; n = 2
c) R = CH₃; R₁ = OEt; R₂, R₃ = H; n = 1
d) R = CH₃; R₁ = NH₂; R₂, R₃ = H; n = 2
e) R = CH₂CH₃; R₁ = NH₂; R₂, R₃ = H; n = 2
f) R = CH₃; R₁ = NH₂; R₂, R₃ = H; n = 1
g) R = H; R₁ = OEt; R₂, R₃ = H; n = 2
h) R = H; R₁ = OEt; R₂, R₃ = C(CH₃)₂; n = 2
i) R = H; R₁ = NH₂; R₂, R₃ = C(CH₃)₂; n = 2
j) R = H; R₁ = NH₂; R₂, R₃ = H; n = 2; H₂SO₄ salt
k) R = CH₃; R₁ = NHNH₂; R₂, R₃ = H; n = 2
l) R = H; R₁ = NHNH₂; R₂, R₃ = H; n = 2
m) R = CH₃; R₁ = NHNH₂; R₂, R₃ = H; n = 1

4a, b, g, h $\xrightarrow{a}$ 13a, b, c, g, h $\xrightarrow{b}$ 13d, e, f, i 13a, c, g $\xrightarrow{d}$ 13k, l, m $^a$ Cl(CH₂)ₙCO₂Et (n = 1 or 2), DMF, DIEA, 60° C.;
$^b$ NH₃/MeOH, RT;
$^c$ 1N H₂SO₄, RT;
$^d$ NH₂NH₂, H₂O, EtOH, reflux Targets with an aminoalkylamino side chain at C-5' were mainly prepared utilizing the displacement of a C-5' leaving group with the unsymmetrical amine (Scheme 4). For example, treatment of 3a with 3-methylaminoethylamine produced a mixture of 14f and 15d, which were separated to afford pure 14f, the desired target. In the case where this procedure involved a starting material with an isopropylidene group, treatment with acid produced the desired final product. In early work, compounds 17c, d were prepared by treatment of a 5'-methylamino-5'-deoxynucleoside with 3-bromopropylphthalimide followed by two deprotection steps.

Scheme 4

3a, c, d, h $\xrightarrow{a}$ 14a, b, c, d, e, f + 15a, b, c, d

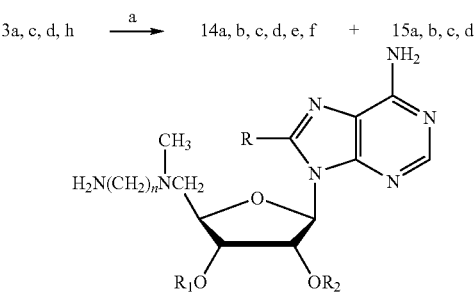

14 a) R = NHCH₃; R₁, R₂ = H; n = 3
b) R = C₆H₅; R₁, R₂ = H; n = 3
c) R = H; R₁, R₂ = C(CH₃)₂; n = 3

$\xrightarrow{b}$ d) R = H; R₁, R₂ = H; n = 3
e) R = H; R₁, R₂ = H; n = 2
f) R = CH₃; R₁, R₂ = H; n = 2

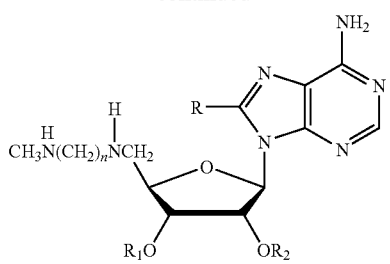

15 a) R = NHCH$_3$; R$_1$, R$_2$ = H; n = 3
b) R = C$_6$H$_5$; R$_1$, R$_2$ = H; n = 3
c) R = H; R$_1$, R$_2$ = H; n = 2
d) R = CH$_3$; R$_1$, R$_2$ = H; n = 2

4e, f $\xrightarrow{c}$

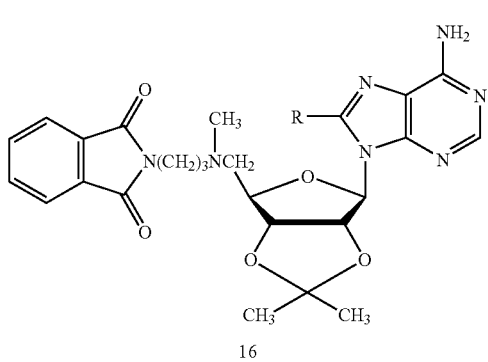

16 a) R = CH$_3$
b) R = CH$_2$CH$_3$ 16a, b $\xrightarrow{d}$ 17a, b

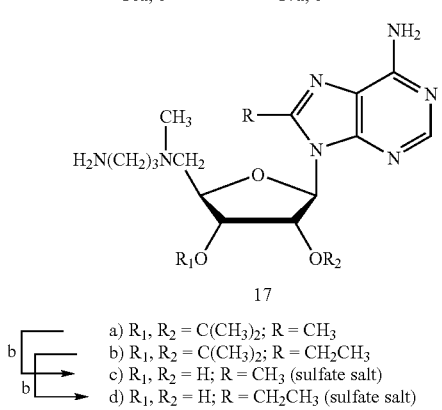

17 a) R$_1$, R$_2$ = C(CH$_3$)$_2$; R = CH$_3$
b) R$_1$, R$_2$ = C(CH$_3$)$_2$; R = CH$_2$CH$_3$
c) R$_1$, R$_2$ = H; R = CH$_3$ (sulfate salt)
d) R$_1$, R$_2$ = H; R = CH$_2$CH$_3$ (sulfate salt)

14e $\xrightarrow{e}$ 18a

3j $\xrightarrow{f, g}$ 18c

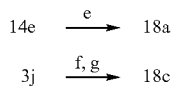

18a) R = $\mathrm{NC}\overset{\mathrm{H}}{\underset{\mathrm{NH_2}}{\diagdown}}\!\!\!\!\!\!=\!\!\!\!\overset{\mathrm{NH}}{\diagup}$ 18b) R = CN (ref.51)

18c) R = $\mathrm{C}\overset{\mathrm{NOH}}{\underset{\mathrm{NH_2}}{\diagup\!\!\!\!\!\diagdown}}$ $^a$ CH$_3$NH(CH$_2$)$_n$ NH$_2$ (n = 1 or 2), RT;
$^b$ 1N H$_2$SO$_4$, RT;
$^c$ 3-Bromopropylphthalimide, DMF, DIEA, 60° C.;
$^d$ NH$_2$NH$_2$, H$_2$O, reflux;
$^e$ 1H-Pyrazole-1-carboxamidine•HCl (ref. 50), MDF, DIEA, RT;
$^f$ 3-(Methylamino)propionitrile, RT (ref. 51);
$^g$ NH$_2$OH•HCl, MeOH, DMF KOH, RT Building on the aminoalkylamino side chain, reaction of 14e with 1-carboxamidinopyrazole[50] produced the guanidine target 18a. In a related sequence, the target amidoxime 18c was prepared by treating 3j with 3-(methylamino)propionitrile to produce the nitrile 18b,[51] which was treated with hydroxylamine hydrochloride under basic conditions.

The 5'-dimethylamino and 5'-dimethylsulfonio compounds 19a, b and 21a-d were prepared by routine methods (Scheme 5). The dimethylamino group was introduced by displacement of a 5'-chlorine on 3a or 3g[43] with dimethylamine. The 5'-methylthio compounds 20a, b were treated with methyl bromide to produce 21a and 21c. Ion exchange was utilized to prepare the chloride salts 21b and 21d. 8-Methyl-5'-methylthio nucleoside 20a was prepared by displacement of the 5'-chlorine in 3a with sodium thiomethoxide.

Scheme 5

3a, g $\xrightarrow{a}$

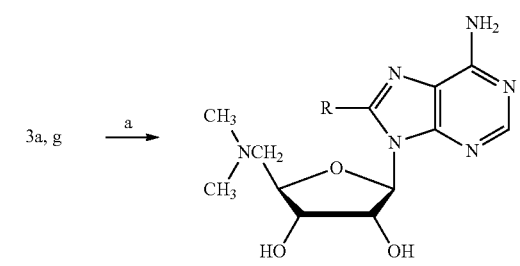

19 a) R = CH$_3$
b) R = H

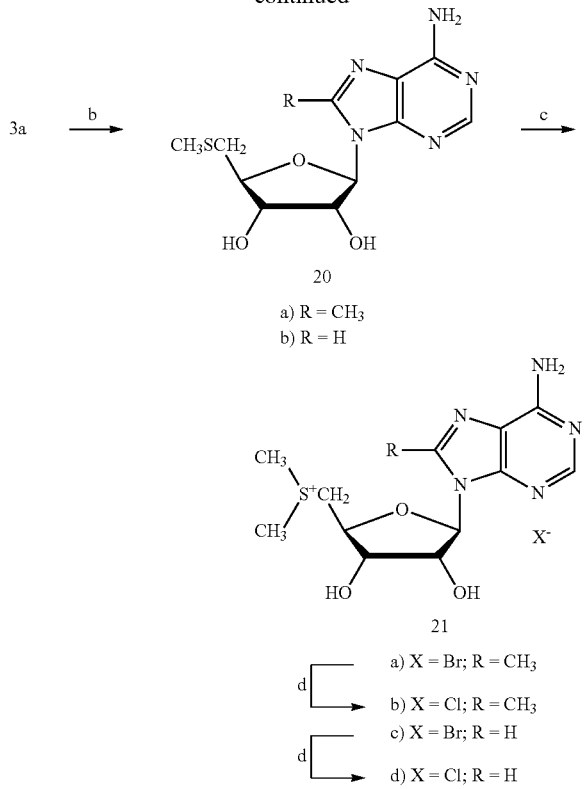

a) R = CH₃
b) R = H a) X = Br; R = CH₃
b) X = Cl; R = CH₃
c) X = Br; R = H
d) X = Cl; R = H $^a$ (CH₃)₂NH, 2M solution in MeOH, 90° C.;
$^b$ CH₃SNa, DMF, RT;
$^c$ CH₃Br, Et₂O, HCO₂H, HOAc, RT;
$^d$ IRA-400 (Cl⁻) ion exchange resin The following non-limiting examples are presented to further illustrate the present disclosure.

Example 1

5'-Chloro-5'-deoxy-8-methyladenosine (3a). To a stirred suspension of 2a[40] (892 mg, 3.17 mmol) in anhydrous pyridine (501 mg, 0.51 mL, 6.33 mmol) and CH₃CN (2.5 mL) cooled in an ice bath was slowly added SOCl₂ (1.88 g, 1.15 mL, 15.80 mmol). Stirring was continued at 0-5° C. for 3-4 h with subsequent warming to ambient temperature overnight. The resulting suspension was concentrated in vacuo. To this reaction mixture was added methanol (20 mL), water (2 mL) and NH₄OH (4 mL) followed by stirring for 0.5 h at room temperature. The reaction mixture was concentrated to dryness. The compound was dissolved in MeOH, silica gel (3g) was added and then solvent was removed. The mixture on silica gel was poured onto a column filled with silica gel and eluted with chloroform:methanol (7:1). Desired fractions were combined, concentrated and dried in vacuo: yield 661 mg (70%); MS m/z 300 (M+H)⁺; ¹HNMR (DMSO-d₆) δ 8.09 (bs, 1H, H-2), 7.15 (bs, 2H, 6-NH₂), 5.81 (d, 1H, H-1', $J_{1',2'}$=5.7 Hz), 5.49 (d, 1H, 2'-OH, $J_{2'-2'OH}$=6.1 Hz), 5.45 (d, 1H, 3'-OH, $J_{3'-3'OH}$=5.3 Hz), 5.13 (ddd, 1H, H-2', $J_{1',2'}$=5.7 Hz, $J_{2',3'}$=4.8 Hz, $J_{2'-2'OH}$=6.1 Hz), 4.31 (ddd, 1H, H-3', $J_{2',3'}$=4.8 Hz, $J_{3',4'}$=4.0 Hz, $J_{3'-3'OH}$=5.3 Hz), 4.03-4.10 (bm, 1H, H-4'), 3.93-3.99 (m, 1H, 5'-CH₂), 3.82-3.88 (m, 1H, 5'-CH₂), 2.55 (s, 3H, 8-CH₃).

Example 2

5'-Chloro-5'-deoxy-8-ethyladenosine (3b). The procedure was the same as reported above for 3a using 2b[40] (1.28 g, 4.33 mmol), pyridine (685 mg, 0.70 mL, 8.65 mmol), CH₃CN (10 mL), and SOCl₂ (2.57 g, 1.58 mL, 21.60 mmol): yield 498 mg (37%); MS m/z 314 (M+H)⁺; ¹HNMR (DMSO-d₆) δ 8.09 (bs, 1H, H-2), 7.14 (bs, 2H, 6-NH₂), 5.80 (d, 1H, H-1', $J_{1',2'}$=5.7 Hz), 5.48 (d, 1H, 2'-OH, $J_{2'-2'OH}$=6.1 Hz), 5.45 (d, 1H, 3'-OH, $J_{3'-3'OH}$=5.4 Hz), 5.20 (ddd, 1H, H-2', $J_{1',2'}$=5.7 Hz, $J_{2',3'}$=4.6 Hz, $J_{2'-2'OH}$=6.1 Hz), 4.30-4.37 (bm, 1H, H-3'), 4.03-4.10 (bm, 1H, H-4'), 3.94-4.0 (m, 1H, 5'-CH₂), 3.83-3.89 (m, 1H, 5'-CH₂), 2.89 (q, 2H, 8-CH₂CH₃), 1.31 (t, 3H, 8-CH₂CH₃).

Example 3

5'-Chloro-5'-deoxy-8-(methylamino)adenosine (3c). Compound 3c was prepared by the same procedure as described for the preparation of 3a using 2c[41] (2.9 g, 9.78 mmol), pyridine (1.54 g, 1.57 mL, 19.46 mmol), CH₃CN (5 mL), and SOCl₂ (5.82 g, 3.56 mL, 48.91 mmol): yield 1.95 g (63%); MS m/z 315 (M+H)⁺; ¹HNMR (DMSO-d₆) δ 7.91 (bs, 1H, H-2), 6.78 (q, 1H, 8CH₃—NH), 6.50 (bs, 2H, 6-NH₂), 5.70 (d, 1H, H-1', $J_{1',2'}$=5.0 Hz), 5.41 (d, 1H, 2'-OH, $J_{2'-2'OH}$=5.6 Hz), 5.32 (d, 1H, 3'-OH, $J_{3'-3'OH}$=5.3 Hz), 5.18 (ddd, 1H, H-2', $J_{1',2'}$=5.0 Hz, $J_{2',3'}$=5.4 Hz, $J_{2'-2'OH}$=5.6 Hz), 4.33 (ddd, 1H, H-3', $J_{2',3'}$=5.4 Hz, $J_{3',4'}$=4.4 Hz, $J_{3'-3'OH}$=5.3 Hz), 3.91-4.02 (bm, 2H, H-4',5'-CH₂), 3.76-3.82 (m, 1H, 5'-CH₂), 2.88 (d, 3H, 8NH—CH₃, J=4.5 Hz).

Example 4

5'-Chloro-5'-deoxy-8-phenyladenosine (3d). The procedure described for 3a was used to prepare 3d from 2d[42] (4.5 g, 13.10 mmol), pyridine (2.07 g, 2.12 mL, 26.2 mmol), CH₃CN (6 mL), and SOCl₂ (7.79 g, 4.78 mL, 65.47 mmol): yield 2.21 g (47%); MS m/z 362 (M+H)⁺; ¹HNMR (DMSO-d₆) δ 8.20 (s, 1H, H-2), 7.71-7.76 (m, 2H, 8-phenyl o-H's), 7.59-7.64 (m, 3H, 8-phenyl m- and p-H's), 7.40 (bs, 2H, 6-NH₂), 5.75 (d, 1H, H-1', $J_{1',2'}$=6.0 Hz), 5.52 (d, 1H, 2'-OH, $J_{2'-2'OH}$=5.6 Hz), 5.39-5.44 (m, 2H, H-2',3'-OH), 4.33 (bs, 1H, H-3'), 3.98-4.06 (bm, 2H, H-4',5'-CH₂), 3.88-3.94 (m, 2H, 5'-CH₂).

Example 5

5'-Deoxy-5'-methylamino-8-methyladenosine (4a). A mixture of 3a (660 mg, 2.20 mmol) in 33% methylamine/ethanol solution (30 mL) in a steel bomb was heated for 2 days at 90° C. The reaction mixture was concentrated to dryness and purified by column chromatography (elution with 4:1:0.3 chloroform:methanol:NH₄OH). The desired fractions were combined, concentrated and dried in vacuo: yield 294 mg (45%); MS m/z 295 (M+H)⁺; ¹HNMR (DMSO-d₆) δ 8.08 (bs, 1H, H-2), 7.14 (bs, 2H, 6-NH₂), 5.72 (d, 1H, H-1', $J_{1',2'}$=6.5 Hz), 5.30 (d, 1H, 2'-OH, $J_{2'-2'OH}$=6.3 Hz), 5.17 (bd, 1H, 3'-OH, $J_{3'-3'OH}$=3.5 Hz), 5.01 (ddd, 1H, H-2', $J_{1',2'}$=6.5 Hz, $J_{2',3'}$=5.5 Hz, $J_{2'-2'OH}$=6.3 Hz), 4.16 (bs, 1H, H-3'), 3.96-4.0 (m, 1H, H-4'), 2.64-2.77 (bm, 2H, 5'-CH₂), 2.53 (s, 3H, 8-CH₃), 2.29 (s, 3H, 5'NH—CH₃).

Example 6

5'-Deoxy-5'-methylamino-8-ethyladenosine (4b). The procedure was the same as reported above for 4a using 3b (1.00 g, 3.18 mmol) and 33% methylamine/ethanol solution (30 mL). After column chromatography (elution with 5:1:0.3 chloroform:methanol:NH₄OH), a yellow glassy solid was obtained: 498 mg (50%); MS m/z 309 (M+H)⁺; ¹HNMR (DMSO-d₆) δ 8.08 (bs, 1H, H-2), 7.13 (bs, 2H, 6-NH₂), 5.70 (d, 1H, H-1', $J_{1',2'}$=6.6 Hz), 5.30 (d, 1H, 2'-OH, $J_{2'-2'OH}$=6.4 Hz), 5.16 (d, 1H, 3'-OH, $J_{3'-3'OH}$=4.5 Hz), 5.08 (ddd, 1H, H-2', $J_{1',2'}$=6.6 Hz, $J_{2',3'}$=5.4 Hz, $J_{2'-2'OH}$=6.4 Hz), 4.14-4.18 (m, 1H, H-3'), 3.96-4.0 (m, 1H, H-4'), 2.88 (q, 2H, 8-CH$_2$CH$_3$), 2.64-2.78 (m, 2H, 5'-CH$_2$), 2.29 (s, 3H, 5'NH—CH$_3$), 1.30 (t, 3H, 8CH$_2$CH$_3$).

Example 7

5'-Deoxy-5',8-bis(methylamino)adenosine (4c). Compound 4c was prepared by the same procedure as described for the preparation of 4a using 3c (1.00 g, 3.17 mmol) and 33% methylamine/ethanol solution (30 mL). After column chromatography (elution with 7:1:0.4 chloroform:methanol:NH$_4$OH), a yellow glassy solid was obtained: 505 mg (51%); MS m/z 310 (M+H)$^+$; $^1$HNMR (DMSO-d$_6$) δ 7.89 (bs and q, 2H, H-2 and 8CH$_3$—NH), 6.44 (bs, 2H, 6-NH$_2$), 5.84 (d, 1H, H-1', $J_{1',2'}$=7.0 Hz), 5.22 (d, 1H, 2'-OH, $J_{2'-2'OH}$=6.4 Hz), 5.12 (d, 1H, 3'-OH, $J_{3'-3'OH}$=4.0 Hz), 4.66 (ddd, 1H, H-2', $J_{1',2'}$=7.0 Hz, $J_{2',3'}$=5.4 Hz, $J_{2'-2'OH}$=6.4 Hz), 4.14 (bm, 1H, H-3'), 3.94-4.0 (bm, 1H, H-4'), 2.90 (d, 3H, 8NH—CH$_3$, J=4.4 Hz), 2.77-2.83 (m, 1H, 5'-CH$_2$), 2.57-2.62 (m, 1H, 5'-CH$_2$), 2.35 (s, 3H, 5'NH—CH$_3$).

Example 8

5'-Deoxy-5'-methylamino-8-phenyladenosine (4d). Compound 4d was prepared by the same procedure as described for the preparation of 4a using 3d (2.00 g, 5.52 mmol) and 33% methylamine/ethanol solution (40 mL). After column chromatography (elution with 4:1:0.2 chloroform:methanol:NH$_4$OH), a yellow glassy solid was obtained: 963 mg (49%); MS m/z 357 (M+H)$^+$; $^1$HNMR (DMSO-d$_6$) δ 8.19 (s, 1H, H-2), 7.72-7.76 (m, 2H, 8-phenyl o-H's), 7.58-7.61 (m, 3H, 8-phenyl m- and p-H's), 7.40 (bs, 2H, 6-NH$_2$), 5.70 (d, 1H, H-1', $J_{1',2'}$=6.4 Hz), 5.38 (d, 1H, 2'-OH, $J_{2'-2'OH}$=6.2 Hz), 5.29 (ddd, 1H, H-2', $J_{1',2'}$=6.4 Hz, $J_{2',3'}$=5.1 Hz, $J_{2'-2'OH}$=6.2 Hz), 5.14 (bs, 1H, 3'-OH), 4.19 (bs, 1H, H-3'), 3.95-4.0 (m, 1H, H-4'), 2.82 (d, 2H, 5'-CH$_2$, J=5.2 Hz), 2.34 (s, 3H, 5'NH—CH$_3$).

Example 9

5'-Deoxy-5'-[[2-[[(1-ethoxyethylidene)amino]oxy]ethyl]methylamino]-8-methyladenosine (6a). A mixture of compound 4a (416 mg, 1.41 mmol), ethyl N-(2-bromoethoxy)ethanamidate[48] (350 mg, 1.66 mmol), and DIEA (11 mg, 0.014 mL, 0.085 mmol) in DMF (5 mL) was heated at 50° C. overnight under nitrogen. The reaction mixture was concentrated to dryness. The resulting syrup was purified by column chromatography (elution with 7:1:0.1 chloroform:methanol:NH$_4$OH). The desired fractions were combined, concentrated and dried in vacuo to give a yellow glassy sticky solid: yield 50 mg (8%); MS m/z 424 (M+H)$^+$; $^1$HNMR (DMSO-d$_6$) δ 8.07 (s, 1H, H-2), 7.11 (bs, 2H, 6-NH$_2$), 5.73 (d, 1H, H-1', $J_{1',2'}$=5.5 Hz), 4.31 (d, 1H, 2'-OH, $J_{2'-2'OH}$=6.3 Hz), 5.15 (d, 1H, 3'-OH, $J_{3'-3'OH}$=5.5 Hz), 5.04 (ddd, 1H, H-2', $J_{1',2'}$=5.5 Hz, $J_{2',3'}$=5.1 Hz, $J_{2'-2'OH}$=6.3 Hz), 4.13 (ddd, 1H, H-3', $J_{2',3'}$=5.1 Hz, $J_{3',4'}$=4.7 Hz, $J_{3'-3'OH}$=5.5 Hz), 3.92 (q, 2H, CH$_2$CH$_3$), 3.88 (t, 2H, NO—CH$_2$), 2.72-2.78 (m, 1H, 5'-CH$_2$), 2.56-2.62 (m, 4H, 5'-CH$_2$, H-4', N(CH$_3$)—CH$_2$), 2.53 (s, 3H, 8-CH$_3$), 2.21 (s, 3H, N—CH$_3$), 1.83 (s, 3H, C—CH$_3$), 1.19 (t, 3H, OCH$_2$CH$_3$).

Example 10

5'-Deoxy-5'-[[2-[[(1-ethoxyethylidene)amino]oxy]ethyl]methylamino]-8-(methylamino)adenosine (6b). Compound 6b was prepared by the same procedure as reported for 6a using 4c (500 mg, 1.61 mmol), ethyl N-(2-bromoethoxy)ethanamidate[48] (407 mg, 1.93 mmol), DIEA (104 mg, 0.14 mL, 0.80 mmol), and DMF (5 mL). After column chromatography (elution with 7:1:0.3 chloroform:methanol:NH$_4$OH), a yellow glassy sticky solid was obtained: yield 209 mg (30%), MS: m/z 439 (M+H)$^+$; $^1$HNMR (DMSO-d$_6$) δ 7.89 (s, 1H, H-2), 6.85 (q, 1H, 8CH$_3$—NH), 6.47 (bs, 2H, 6-NH$_2$), 5.69 (d, 1H, H-1', $J_{1',2'}$=5.0 Hz), 5.27 (d, 1H, 2'-OH, $J_{2'-2'OH}$=5.5 Hz), 5.06 (d, 1H, 3'-OH, $J_{3'-3'OH}$=5.0 Hz), 4.88 (ddd, 1H, H-2', $J_{1',2'}$=5.0 Hz, $J_{2',3'}$=5.8 Hz, $J_{2'-2'OH}$=5.5 Hz), 4.17 (ddd, 1H, H-3', $J_{2',3'}$=5.8 Hz, $J_{3',4'}$=4.7 Hz, $J_{3'-3'OH}$=5.0 Hz), 3.86-3.95 (m, 3H, H-4', NO—CH$_2$), 3.92 (q, 2H, CH$_2$CH$_3$), 2.88 (d, 3H, 8NH—CH$_3$, J=4.6 Hz), 2.71-2.77 (m, 1H, 5'-CH$_2$), 2.56-2.67 (m, 3H, 5'-CH$_2$, N(CH$_3$)—CH$_2$), 2.24 (s, 3H, N—CH$_3$), 1.83 (s, 3H, C—CH$_3$), 1.19 (t, 3H, OCH$_2$CH$_3$).

Example 11

5'-Deoxy-5'-[[2-[[(1-ethoxyethylidene)amino]oxy]ethyl]methylamino]-8-phenyladenosine (6c). The procedure described for 6a was used to prepare 6c from 4d (400 mg, 1.12 mmol), ethyl N-(2-bromoethoxy)ethanamidate[48] (283 mg, 1.34 mmol), and DIEA (72 mg, 0.10 mL, 0.55 mmol). After column chromatography (elution with 7:1 chloroform:methanol), a yellow glassy sticky solid was obtained: yield 105 mg (20%), MS: m/z 486 (M+H)$^+$; $^1$HNMR (DMSO-d$_6$) δ 8.17 (s, 1H, H-2), 7.72-7.78 (m, 2H, 8-phenyl o-H's), 7.58-7.63 (m, 3H, 8-phenyl m- and p-H's), 7.36 (bs, 2H, 6-NH$_2$), 5.67 (d, 1H, H-1', $J_{1',2'}$=5.2 Hz), 5.29-5.34 (m, 2H, 2'-OH, H-2'), 5.13 (d, 1H, 3'-OH, 5.3 Hz), 4.14-4.18 (m, 1H, H-3'), 3.88-3.97 (m, 3H, H-4', NO—CH$_2$), 3.92 (q, 2H, CH$_2$CH$_3$), 2.78-2.84 (m, 1H, 5'-CH$_2$), 2.60-2.70 (m, 3H, 5'-CH$_2$, N(CH$_3$)—CH$_2$), 2.24 (bs, 3H, N—CH$_3$), 1.83 (s, 3H, C—CH$_3$), 1.19 (t, 3H, OCH$_2$CH$_3$).

Example 12

5'-[(2-Aminooxyethyl)methylamino]-5'-deoxy-8-methyladenosine sulfate (2.2:1 salt) (7a). Compound 6a (50 mg, 0.11 mmol) was dissolved in 2 mL of 2N H$_2$SO$_4$ and stirred for 2 days at room temperature. The reaction mixture was neutralized with NaHCO$_3$ and lyophilized. The compound was extracted with EtOH (2×10 mL) and concentrated to dryness. The residue was purified by column chromatography (silica gel 230-400 mesh, elution with 7:1:0.3 chloroform:methanol:NH$_4$OH). The desired fractions were combined, concentrated, and dried in vacuo. The product was dissolved in 3 mL of EtOH and 2N H$_2$SO$_4$ was added dropwise. The resulting sulfate salt that precipitated out was filtered, and washed with EtOH. This product, which was hygroscopic in nature, was dissolved in water (2 mL) and lyophilized to give a white solid: yield 20 mg (29%), MS: m/z 354 (M+H)$^+$; $^1$HNMR (DMSO-d$_6$) δ 8.25 (s, 1H, H-2), 7.80 (bs, 2H, O—NH$_2$), 5.87 (d, 1H, H-1', $J_{1',2'}$=5.7 Hz), 4.88 (t, 1H, H-2', $J_{2',3'}$=5.2 Hz), 4.35-4.40 (bm, 1H, H-4'), 4.23 (t, 1H, H-3', $J_{2',3'}$=3.2 Hz), 4.10 (t, 2H, NH$_2$O—CH$_2$), 3.50-3.57 (m, 1H, 5'-CH$_2$), 3.65-3.72 (m, 1H, 5'-CH$_2$), 3.45 (bm, 2H, N(CH$_3$)—CH$_2$), 2.85 (s, 3H, N—CH$_3$), 2.58 (s, 3H, 8-CH$_3$); UV $\lambda_{max}$, nm, pH 1, 274 (∈ 15,200), pH 7, 276 (∈ 15,500), pH 13, 277 (∈ 15,900). Anal. (C$_{14}$H$_{23}$N$_7$O$_4$.2.2H$_2$SO$_4$.0.1C$_2$H$_5$OH.0.5H$_2$O) C, H, N.

Example 13

5'-[(2-Aminooxyethyl)methylamino]-5'-deoxy-8-(methylamino)adenosine sulfate (2.1:1 salt) (7b). The procedure described for 7a was used to prepare 7b from 6b (200 mg, 0.45 mmol): yield 125 mg (46%), MS: m/z 369 (M+H)$^+$; $^1$HNMR (DMSO-d$_6$) δ 8.16 (s, 1H, H-2), 7.50-7.65 (bm, 2H, O—NH$_2$), 5.83 (d, 1H, H-1', J$_{1',2'}$=5.3 Hz), 6.56 (bs, 2H, 6-NH$_2$), 4.96 (t, 1H, H-2', J$_{2',3'}$=4.8 Hz), 4.28-4.35 (bm, 1H, H-4'), 4.25 (t, 1H, H-3', J$_{2,3}$=4.1 Hz), 3.96 (t, 2H, NH$_2$O—CH$_2$), 3.59-3.66 (m, 1H, 5'-CH$_2$), 3.49-3.57 (m, 1H, 5'-CH$_2$), 3.36-3.40 (bm, 2H, N(CH$_3$)—CH$_2$), 2.94 (s, 3H, 8NH—CH$_3$), 2.81 (s, 3H, N—CH$_3$); UV λ$_{max}$, nm, pH 1, 274 (∈ 14,300), pH 7, 276.7 (∈ 17,100), pH 13, 276.1 (∈ 17,500). Anal. (C$_{14}$H$_{24}$N$_8$O$_4$.2.1H$_2$SO$_4$.0.3C$_2$H$_5$OH.0.2H$_2$O) C, H, N, S.

Example 14

5'-[(2-Aminooxyethyl)methylamino]-5'-deoxy-8-phenyladenosine sulfate (2:1 salt) (7c). Compound 7c was prepared by the same procedure as described for the preparation of 7a using 6c (99 mg, 0.20 mmol): yield 57 mg (42%), MS: m/z 416 (M+H)$^+$; $^1$HNMR (D$_2$O) δ 8.37 (s, 1H, H-2), 7.73-7.76 (m, 2H, 8-phenyl o-H's), 7.60-7.70 (m, 3H, 8-phenyl m- and p-H's), 6.02 (d, 1H, H-1', J$_{1',2'}$=5.7 Hz), 5.25 (t, 1H, H-2', J$_{2',3'}$=4.9 Hz), 4.46-4.54 (bm, 2H, H-3', 4'), 4.03 (t, 2H, NH$_2$O—CH$_2$), 3.87-4.0 (m, 1H, 5'-CH$_2$), 3.61-3.67 (m, 1H, 5'-CH$_2$), 3.50-3.55 (m, 2H, N(CH$_3$)—CH$_2$), 3.0 (s, 3H, N—CH$_3$); UV λ$_{max}$, nm, pH 1, 275 (∈ 21,600), pH 7, 275 (∈ 17,100), pH 13, 274.4 (∈ 16,800). Anal. (C$_{19}$H$_{25}$N$_7$O$_4$.2.0H$_2$SO$_4$.3H$_2$O) C, H, N, S.

Example 15

5'-Deoxy-5'-[[4-[[(1-ethoxyethylidene)amino]oxy]butyl]methylamino]-8-(methylamino)adenosine (8a). Compound 8a was prepared by the same procedure as reported for 6a using 4c (1.00 g, 3.23 mmol), ethyl N-(4-bromobutoxy)ethanimidate[49] (924 mg, 3.87 mmol), and DIEA (209 mg, 0.28 mL, 1.6 mmol): yield 635 mg (42%), MS: m/z 467 (M+H)$^+$; $^1$HNMR (DMSO-d$_6$) δ 7.89 (s, 1H, H-2), 6.87 (q, 1H, 8CH$_3$—NH), 6.46 (bs, 2H, 6-NH$_2$), 5.69 (d, 1H, H-1', J$_{1',2'}$=4.8 Hz), 5.25 (d, 1H, 2'-OH, J$_{2'-2'OH}$=5.6 Hz), 5.06 (d, 1H, 3'-OH, J$_{3'-3'OH}$=5.4 Hz), 4.91 (ddd, 1H, H-2', J$_{1',2'}$=4.8 Hz, J$_{2',3'}$=5.4 Hz, J$_{2'-2'OH}$=5.6 Hz), 4.16 (ddd, 1H, H-3', J$_{2',3'}$=5.4 Hz, J$_{3',4'}$=4.9 Hz, J$_{3'-3'OH}$=5.4 Hz), 3.85-3.94 (m, 1H, H-4'), 3.92 (q, 2H, OCH$_2$CH$_3$), 3.80 (t, 2H, NO—CH$_2$), 2.88 (d, 3H, 8NH—CH$_3$, J=4.6 Hz), 2.65-2.74 (m, 1H, 5'-CH$_2$), 2.46-2.58 (m, 1H, 5'-CH$_2$), 2.34 (t, 2H, N(CH$_3$)—CH$_2$), 2.17 (s, 3H, N—CH$_3$), 1.83 (s, 3H, C—CH$_3$), 1.37-1.61 (bm, 4H, NOCH$_2$—CH$_2$CH$_2$), 1.19 (t, 3H, OCH$_2$CH$_3$).

Example 16

5'-Deoxy-5'-[[4-[[(1-ethoxyethylidene)amino]oxy]butyl]methylamino]-8-phenyladenosine (8b). The same procedure as described for 6a, was used to prepare 8b from 4d (450 mg, 1.26 mmol), ethyl N-(4-bromobutoxy)ethanimidate[49] (360 mg, 1.51 mmol), and DIEA (81 mg, 0.10 mL, 0.62 mmol). After column chromatography (elution with 7:1 chloroform:methanol), a yellow glassy sticky solid was obtained: yield 312 mg (48%), MS: m/z 514 (M+H)$^+$; $^1$HNMR (DMSO-d$_6$) δ 8.17 (s, 1H, H-2), 7.71-7.78 (m, 2H, 8-phenyl o-H's), 7.58-7.64 (m, 3H, 8-phenyl m- and p-H's), 7.36 (bs, 2H, 6-NH$_2$), 5.67 (d, 1H, H-1', J$_{1',2'}$=5.7 Hz), 5.32 (bs, 1H, 2'-OH), 5.31 (t, 1H, H-2', J$_{1',2'}$=5.7 Hz, J$_{2,3}$=5.4 Hz), 5.11 (d, 1H, 3'-OH, J$_{3'-3'OH}$=4.8 Hz), 4.16 (bddd, 1H, H-3', J$_{2',3'}$=5.4 Hz, J$_{3',4'}$=4.0 Hz), 3.92-3.97 (m, 1H, H-4'), 3.91 (q, 2H, OCH$_2$CH$_3$), 3.79 (t, 2H, NO—CH$_2$), 2.72-2.80 (m, 1H, 5'-CH$_2$), 2.54-2.59 (m, 1H, 5'-CH$_2$), 2.34 (bt, 2H, N(CH$_3$)—CH$_2$), 2.17 (bs, 3H, N—CH$_3$), 1.83 (s, 3H, C—CH$_3$), 1.39-1.60 (bm, 4H, NOCH$_2$—CH$_2$CH$_2$), 1.18 (t, 3H, OCH$_2$CH$_3$).

Example 17

5'-Deoxy-5'-[[4-[[(1-ethoxyethylidene)amino]oxy]butyl]methylamino]-8-oxoadenosine (8c).

The procedure described for 6a was used to prepare 8c from 4i[45] (500 mg, 1.68 mmol), ethyl N-(4-bromobutoxy)ethanimidate[49] (481 mg, 2.01 mmol), DIEA (109 mg, 0.14 mL, 0.84 mmol), and DMF (5 mL). After column chromatography (elution with 4:1:0.2 chloroform:methanol:NH$_4$OH), a yellow glassy sticky solid was obtained: yield 200 mg (26%), MS: m/z 454 (M+H)$^+$; $^1$HNMR (DMSO-d$_6$) δ 10.34 (bs, 1H, 8-OH), 8.02 (s, 1H, H-2), 6.49 (bs, 2H, 6-NH$_2$), 5.62 (d, 1H, H-1', J$_{1',2'}$=5.0 Hz), 4.99 (bs, 1H, 3'-OH), 5.19 (bs, 1H, 2'-OH), 4.90 (t, 1H, H-2', J$_{2',3'}$=5.4 Hz), 4.16-4.24 (bm, 1H, H-3'), 3.83-3.89 (m, 1H, H-4'), 3.92 (q, 2H, OCH$_2$CH$_3$), 3.77 (t, 2H, NO—CH$_2$), 2.62-3.68 (m, 1H, 5'-CH$_2$), 2.40-2.46 (m, 1H, 5'-CH$_2$), 2.30 (t, 2H, N(CH$_3$)—CH$_2$), 2.13 (s, 3H, N—CH$_3$), 1.84 (s, 3H, C—CH$_3$), 1.35-1.60 (bm, 4H, NOCH$_2$—CH$_2$CH$_2$), 1.21 (t, 3H, OCH$_2$CH$_3$).

Example 18

5'-Deoxy-2',3'-isopropylidene-5'-[[4-[[(1-ethoxyethylidene)amino]oxy]butyl]methylamino]-8-methyladenosine (8d). Compound 8d was prepared by the same procedure as reported for 6a using 4e (1.00 g, 3.11 mmol), MsCl (392 mg, 0.26 mL, 3.42 mmol), methylamine (25 mL), ethyl N-(4-bromobutoxy)ethanimidate (853 mg, 3.58 mmol), DIEA (200 mg, 0.27 mL, 1.54 mmol), and DMF (8 mL). After column chromatography (95:5 chloroform:methanol), a glassy solid was obtained: yield 176 mg (12%), MS: m/z 492 (M+H)$^+$; $^1$HNMR (CDCl$_3$) δ 8.27 (s, 1H, H-2), 5.99 (d, 1H, H-1', J$_{1,2}$=1.8 Hz), 5.75 (dd, 1H, H-2', J$_{1,2}$=1.8 Hz, J$_{2,3}$=6.4 Hz), 5.39 (bs, 2H, 6-NH$_2$), 5.08 (dd, 1H, H-3', J$_{2,3}$=6.4 Hz, J$_{3,4}$=3.5 Hz), 4.27-4.34 (m, 1H, H-4'), 4.0 (q, 2H, OCH$_2$CH$_3$), 3.84 (t, 2H, NO—CH$_2$), 2.64 (s, 3H, 8-CH$_3$), 2.55-2.61 (m, 1H, 5'-CH$_2$), 2.45-2.55 (m, 1H, 5'-CH$_2$), 2.29-2.34 (m, 2H, N(CH$_3$)—CH$_2$), 2.21 (s, 3H, N—CH$_3$), 1.91 (s, 3H, C—CH$_3$), 1.61 and 1.40 (2s, 6H, C(CH$_3$)$_2$), 1.51-1.60 (m, 2H, NOCH$_2$—CH$_2$), 1.37-1.45 (m, 2H, N(CH$_3$)CH$_2$—CH$_2$), 1.27 (t, 3H, OCH$_2$CH$_3$).

Example 19

5'-Deoxy-2',3'-isopropylidene-5'-[[4-[[(1-ethoxyethylidene)amino]oxy]butyl]methylamino]-8-ethyladenosine (8e). The procedure described for 6a was used to prepare 8e from 4f (1.00 g, 2.98 mmol), MsCl (375 mg, 0.25 mL, 3.27 mmol), methylamine (25 mL), ethyl N-(4-bromobutoxy) ethanimidate (852 mg, 3.57 mmol), DIEA (192 mg, 0.25 mL, 1.48 mmol), and DMF (10 mL). After column chromatography (95:5 chloroform:methanol), a glassy solid was obtained: yield 159 mg (11%), MS: m/z 506 (M+H)$^+$; $^1$HNMR (CDCl$_3$) δ 8.27 (s, 1H, H-2), 5.99 (d, 1H, H-1', J$_{1,2}$=2.0 Hz), 5.73 (dd, 1H, H-2', J$_{1,2}$=2.0 Hz, J$_{2,3}$=6.4 Hz), 5.40 (bs, 2H, 6-NH$_2$), 5.09 (dd, 1H, H-3', J$_{2,3}$=6.4 Hz, J$_{3,4}$=3.6 Hz), 4.26-4.33 (m, 1H, H-4'), 4.0 (q, 2H, OCH$_2$CH$_3$), 3.84 (t, 2H, NO—CH$_2$), 2.91-2.99 (m, 2H, CH$_2$ of 8-Et), 2.59-2.65 (m, 1H, 5'-CH$_2$), 2.46-2.53 (m, 1H, 5'-CH$_2$), 2.30-2.35 (m, 2H, N(CH$_3$)—CH$_2$), 2.21 (s, 3H, N—CH$_3$), 1.91 (s, 3H, C—CH$_3$), 1.61 and 1.40 (2s, 6H, C(CH$_3$)$_2$), 1.51-1.59 (m, 2H, NOCH$_2$—CH$_2$), 1.49-1.38 (m, 2H, N(CH$_3$)CH$_2$—CH$_2$), 1.43 (s, 31-1, CH$_3$ of 8-Et), 1.27 (t, 3H, OCH$_2$CH$_3$).

Example 20

5'-Deoxy-2',3'-isopropylidene-5'-[[4-[[(1-ethoxyethylidene)amino]oxy]butyl]methylamino]-adenosine (81). Compound 8f was prepared by the same procedure as reported for 6a using 4g[43] (1.00 g, 3.25 mmol), MsCl (447 mg, 0.30 mL, 3.90 mmol), methylamine (25 mL), ethyl N-(4-bromobutoxy)ethanimidate (511 mg, 2.15 mmol), DIEA (125 mg, 0.17 mL, 0.96 mmol), and DMF (5 mL). After column chromatography (95:5 chloroform:methanol), a pale yellow syrup was obtained: yield 839 mg (86%), MS: m/z 478 (M+H)$^+$; $^1$HNMR (CDCl$_3$) δ 8.36 (s, 1H, H-2), 7.96 (s, 1H, H-8), 6.07 (d, 1H, H-1', J$_{1',2'}$=2.2 Hz), 5.60 (bs, 2H, 6-NH$_2$), 5.49 (dd, 1H, H-2', J$_{1',2'}$=2.2 Hz, J$_{2',3'}$=6.4 Hz), 4.95 (dd, 1H, H-3', J$_{2',3'}$=6.4 Hz, J$_{3',4'}$=3.4 Hz), 4.36-4.40 (m, 1H, H-4'), 4.0 (q, 2H, OCH$_2$CH$_3$), 3.86 (t, 2H, NO—CH$_2$), 2.61 (dd, 1H, 5'-CH$_2$), 2.55 (dd, 1H, 5'-CH$_2$), 2.38 (bt, 2H, N(CH$_3$)—CH$_2$), 2.26 (s, 3H, N—CH$_3$), 1.91 (s, 3H, C—CH$_3$), 1.61 and 1.40 (2s, 6H, C(CH$_3$)$_2$), 1.55-1.61 (m, 2H, NOCH$_2$—CH$_2$), 1.44-1.52 (m, 2H, N(CH$_3$)CH$_2$—CH$_2$), 1.27 (t, 3H, OCH$_2$CH$_3$).

Example 21

5'-[(4-Aminooxybutyl)methylamino]-5'-deoxy-8-(methylamino)adenosine sulfate (0.4:1 salt) (9a). The same procedure used to prepare 7a was used to prepare 9a using 8a (600 mg, 1.28 mmol) and 2N H$_2$SO$_4$ (10 mL): yield 514 mg (87%), MS: m/z 510 (M+H)$^+$; $^1$HNMR (DMSO-d$_6$) δ 7.91 (s, 1H, H-2), 6.88 (bq, 1H, 8CH$_3$—NH), 6.50 (bs, 2H, 6-NH$_2$), 5.72 (d, 1H, H-1', J$_{1',2'}$=5.1 Hz), 5.08-5.39 (bm, 2H, 2',3'-OH), 4.0-5.02 (m, 1H, H-2'), 4.19 (t, 1H, H-3'), 3.94-4.06 (bm, 1H, H-4'), 3.45 (bt, 2H, NH$_2$O—CH$_2$), 3.36-3.54 (m, 2H, 5'-CH$_2$), 2.89 (d, 3H, 8NH—CH$_3$), 2.78-2.95 (bm, 2H, NCH$_3$—CH$_2$), 2.04 (bs, 3H, N—CH$_3$), 1.38-1.52 (bm, 4H, NH$_2$OCH$_2$—CH$_2$CH$_2$); UV λ$_{max}$, nm, pH 1, 274.8 (∈ 14,300), pH 7, 276 (∈ 16,700), pH 13, 277 (∈ 17,400). Anal. (C$_{16}$H$_{28}$N$_8$O$_4$.0.4H$_2$SO$_4$.0.2C$_2$H$_5$OH.0.9H$_2$O) C, H, N, S.

Example 22

5'-[(4-Aminooxybutyl)methylamino]-5'-deoxy-8-phenyladenosine sulfate (1.75:1 salt) (9b). Compound 9b was prepared by the same procedure as described for the preparation of 7a using 8b (305 mg, 0.59 mmol) and 2N H$_2$SO$_4$ (4 mL): yield 252 mg (64%), MS: m/z 444 (M+H)$^+$; $^1$HNMR (DMSO-d$_6$) δ 8.18 (s, 1H, H-2), 7.20-7.78 (m, 2H, 8-phenyl o-H's), 7.59-7.61 (m, 3H, 8-phenyl m- and p-H's), 7.37 (bs, 2H, 6-NH$_2$), 5.85 (s, 2H, O—NH$_2$), 5.68 (d, 1H, H-1', J$_{1',2'}$=5.7 Hz), 5.31 (t, 1H, H-2', J$_{2',3'}$=5.5 Hz), 5.13 (bd, 1H, 3'-OH), 4.18 (t, 1H, H-3', J$_{3',4'}$=3.9 Hz), 3.94-3.99 (bm, 1H, H-4'), 3.49 (t, 2H, NH$_2$O—CH$_2$), 2.73-2.79 (m, 1H, 5'-CH$_2$), 2.54-2.62 (m, 1H, 5'-CH$_2$), 2.27-2.36 (bm, 2H, N(CH$_3$)—CH$_2$), 2.16 (bs, 3H, N—CH$_3$), 1.33-1.53 (bm, 4H, NH$_2$OCH$_2$—CH$_2$CH$_2$); $^1$HNMR (D$_2$O) δ 8.36 (s, 1H, H-2), 7.72-7.78 (m, 2H, 8-phenyl o-H's), 7.63-7.71 (m, 3H, 8-phenyl m- and p-H's), 6.02 (d, 1H, H-1', J$_{1',2'}$=5.8 Hz), 5.28-5.41 (bm, 1H, H-2'), 4.43-4.53 (bm, 2H, H-3', 4'), 3.92-4.03 (m, 1H, 5'-CH$_2$), 3.90 (t, 2H, NH$_2$O—CH$_2$), 3.49-3.59 (m, 1H, 5'-CH$_2$), 3.22-3.32 (bm, 2H, N(CH$_3$)—CH$_2$), 2.92 (bs, 3H, N—CH$_3$), 1.61-1.83 (bm, 4H, NH$_2$OCH$_2$—CH$_2$CH$_2$); UV λ$_{max}$, nm, pH 1, 275 (∈ 21,400), pH 7, 274.5 (∈ 16,900), pH 13, 274.8 (∈ 16,700). Anal. (C$_{21}$H$_{29}$N$_7$O$_4$.1.75H$_2$SO$_4$.0.05C$_2$H$_5$OH.2.4H$_2$O) C, H, N, S.

Example 23

5'-[(4-Aminooxybutyl)methylamino]-5'-deoxy-8-oxoadenosine sulfate (1.9:1 salt) (9c). The procedure was the same as reported above for 7a using 8c (190 mg, 0.41 mmol) and 2N H$_2$SO$_4$ (3 mL). The compound was purified by column chromatography (elution with 4:1:0.5 chloroform:methanol:NH$_4$OH): yield 208 mg (82%), MS: m/z 384 (M+H)$^+$; $^1$HNMR (DMSO-d$_6$) δ 10.45 (bs, 1H, 8-OH), 8.05 (s, 1H, H-2), 6.58 (bs, 2H, 6-NH$_2$), 5.77 (d, 1H, H-1', J$_{1',2'}$=5.0 Hz), 5.37-5.71 (bm, 2H, O—NH$_2$), 4.83 (t, 1H, H-2', J$_{2',3'}$=4.2 Hz), 4.18-4.29 (m, 2H, H-3', H-4'), 3.88 (t, 2H, NH$_2$O—CH$_2$), 3.34-3.54 (m, 2H, 5'-CH$_2$), 3.06 (bt, 2H, N(CH$_3$)—CH$_2$), 2.73 (s, 3H, N—CH$_3$), 1.46-1.74 (bm, 4H, NH$_2$OCH$_2$—CH$_2$CH$_2$); UV λ$_{max}$, nm, pH 1, 263.3 (∈ 12,200), pH 7, 268.9 (∈ 13,600), pH 13, 279.9 (∈ 15,600). Anal. (C$_{15}$H$_{25}$N$_7$O$_5$.1.9H$_2$SO$_4$.0.1C$_2$H$_5$OH.2H$_2$O) C, H, N, S.

Example 24

5'-[(4-Aminooxybutyl)methylamino]-5'-deoxy-8-methyladenosine sulfate (1.9:1 salt) (9d). Compound 8d (149 mg, 0.30 mmol) was dissolved in 2.5 mL of 1N H$_2$SO$_4$ and stirred for 12 days at room temperature. The reaction mixture was neutralized with NaHCO$_3$ and lyophilized. The compound was extracted with EtOH (2×10 mL) and concentrated to dryness. The residue was purified by column chromatography (silica gel 230-400 mesh, elution with 4:1:0.2 chloroform:methanol:NH$_4$OH). The desired fractions were collected, concentrated, and dried in vacuo. The product was dissolved in 8 mL of EtOH and 2N H$_2$SO$_4$ was added dropwise. The sulfate salt that precipitated out was filtered and washed with EtOH. This product was dissolved in water (2 mL) and lyophilized to give a white solid: yield 59 mg (33%), MS: m/z 382 (M+H)$^+$; $^1$HNMR (D$_2$O) δ 8.39 (s, 1H, H-2), 6.08 (d, 1H, H-1', J$_{1',2'}$=5.5 Hz), 5.0-5.19 (bm, 1H, H-2'), 4.51-4.58 (bm, 2H, H-3', 4'), 4.08 (t, 2H, NH$_2$O—CH$_2$), 3.73-4.0 (m, 1H, 5'-CH$_2$), 3.44-3.69 (m, 1H, 5'-CH$_2$), 3.16-3.36 (bm, 2H, N(CH$_3$)—CH$_2$), 2.92 (bs, 3H, N—CH$_3$), 2.70 (s, 3H, 8-CH$_3$), 1.68-1.88 (bm, 4H, NH$_2$OCH$_2$—CH$_2$CH$_2$); UV λ$_{max}$, nm, pH 1, 258.2 (∈ 15,400), pH 7, 259.7 (∈ 15,500), pH 13, 260.9 (∈ 15,900). Anal. (C$_{16}$H$_{27}$N$_7$O$_4$.1.9H$_2$SO$_4$.0.4C$_2$H$_5$OH) C, H, N.

Example 25

5'-[(4-Aminooxybutyl)methylamino]-5'-deoxy-8-ethyladenosine sulfate (1.9:1 salt) (9e). The procedure was the same as reported above for 9d using 8e (155 mg, 0.30 mmol): yield 55 mg (30%), MS: m/z 396 (M+H)$^+$; $^1$HNMR (D$_2$O) δ8.39 (s, 1H, H-2), 6.09 (d, 1H, H-1', J$_{1',2'}$=5.6 Hz), 5.07-5.23 (bm, 1H, H-2'), 4.50-4.60 (bm, 2H, H-3', 4'), 4.06 (t, 2H, NH$_2$O—CH$_2$), 3.82-3.96 (m, 1H, 5'-CH$_2$), 3.45-3.69 (m, 1H, 5'-CH$_2$), 3.27 (bs, 2H, N(CH$_3$)—CH$_2$), 3.0-3.10 (m, 2H, 8CH$_2$CH$_3$), 2.91 (bs, 3H, N—CH$_3$), 1.68-1.86 (bm, 4H, NH$_2$OCH$_2$—CH$_2$CH$_2$), 1.39 (t, 3H, 8CH$_2$CH$_3$); UV λ$_{max}$, nm, pH 1, 259.1 (∈ 16,400), pH 7, 260 (∈ 15,700), pH 13, 260.2 (∈ 15,900). Anal. (C$_{17}$H$_{29}$N$_7$O$_4$.1.9H$_2$SO$_4$.0.2C$_2$H$_5$OH) C, H, N.

Example 26

5'-[(4-Aminooxybutyl)methylamino]-5'-deoxyadenosine sulfate (2:1 salt) (90. The procedure was the same as reported above for 9d using 8f (750 mg, 1.5 mmol): yield 457 mg (48%), MS: m/z 368 (M+H)$^+$; $^1$HNMR (DMSO-d$_6$) δ 8.43 (s, 1H, H-8), 8.23 (s, 1H, H-2), 7.58 (bs, 2H, 6-NH$_2$), 6.03 (d, 1H, H-1', J$_{1',2'}$=5.4 Hz), 4.75 (t, 1H, H-2', J$_{1',2'}$=5.4 Hz, J$_{2',3'}$=4.8

Hz), 4.32-4.40 (bm, 2H, H-4'), 4.23 (t, 1H, H-3', $J_{3',4'}$=3.8 Hz), 3.93 (t, 2H, NH$_2$O—CH$_2$), 3.68 (dd, 1H, 5'-CH$_2$), 3.49 (bdd, 1H, 5'-CH$_2$), 3.13 (bt, 2H, N(CH$_3$)—CH$_2$), 2.80 (s, 3H, N—CH$_3$), 1.50-1.78 (bm, 4H, NH$_2$OCH$_2$—CH$_2$CH$_2$). Anal. (C$_{15}$H$_{25}$N$_7$O$_4$.2.0H$_2$SO$_4$.0.3C$_2$H$_5$OH.1.5H$_2$O) C, H, N, S.

Example 27

5'-Deoxy-2',3'-O-isopropylidene-5'-[(2-hydroxyethyl)methylamino]adenosine (10). Compound 3i[45] (8.20 g, 17.79 mmol) was dissolved in 2-(methylamino)ethanol (54 mL, 673 mmol) and stirred at room temperature for 41 h. The solvent was evaporated to give a yellow residue. The residue was dissolved in 100 mL of chloroform and washed with NaHCO$_3$ (3×50 mL). The organic layer was dried over Na$_2$SO$_4$ and concentrated to dryness to give yellow foam. The residue was purified by column chromatography (silica gel 230-400 mesh, elution with 9:1:0.1 chloroform:methanol:NH$_4$OH). The desired fractions were combined, concentrated, and dried in vacuo: yield 2.55 g (39%), MS: m/z 365 (M+H)$^+$; $^1$HNMR (DMSO-d$_6$) δ 8.34 (s, 1H, H-2), 8.18 (s, 1H, H-8), 7.33 (bs, 2H, 6-NH$_2$), 6.13 (d, 1H, H-1', $J_{1',2'}$=2.5 Hz), 5.48 (dd, 1H, H-2', $J_{2',3'}$=6.3 Hz), 4.96 (dd, 1H, H-3', $J_{3',4'}$=3.0 Hz), 4.33 (t, 1H, OH), 4.24 (dt, 1H, H-4'), 3.44 (t, 2H, OH—CH$_2$), 2.64 (dd, 1H, 5'-CH$_2$), 2.35-2.49 (m, 3H, 5'-CH$_2$, N(CH$_3$)—CH$_2$), 2.18 (s, 3H, N—CH$_3$), 1.54 and 1.33 (2s, 6H, C(CH$_3$)$_2$).

Example 28

5'-Deoxy-2',3'-O-isopropylidene-5'-[(2-phthalimidooxyethyl)methylamino]-adenosine (11). To a solution of compound 10 (989 mg, 2.714 mmol), N-hydroxyphthalimide (1.107 g, 6.786 mmol) and P(Ph)$_3$ (1.780 g, 6.787 mmol) in 50 mL of anhydrous THF was added DEAD (1.07 mL, 6.8 mmol) in THF (10 mL) under nitrogen over a period of 3 min at room temperature. After 5 min 2% of sodium carbonate (75 mL) was added to the reaction mixture followed by dichloromethane (100 mL). The organic layer was washed with 2% Na$_2$CO$_3$ (75 mL) and then with saturated NaCl (2×75 mL). The organic layer was dried over Na$_2$SO$_4$ and concentrated to dryness to give a foam. The residue was purified by column chromatography and eluted from the column with 1:3 dichloromethane:acetone). The desired fractions were combined, concentrated, and dried in vacuo: yield 842 mg (61%), MS: m/z 510 (M+H)$^+$)$^+$; $^1$HNMR (CDCl$_3$) δ 8.36 (s, 1H, H-2), 8.07 (s, 1H, H-8), 7.79-7.83 (m, 2H, phthalimido aromatic H's), 7.63-7.72 (m, 2H, phthalimido aromatic H's), 6.12 (d, 1H, H-1', $J_{1',2'}$=2.2 Hz), 5.87 (bs, 2H, 6-NH$_2$), 5.49 (dd, 1H, H-2', $J_{1',2'}$=2.2 Hz, $J_{2',3'}$=6.4 Hz), 5.05 (dd, 1H, H-3', $J_{2',3'}$=6.4 Hz, $J_{3',4'}$=3.3 Hz), 4.40-4.45 (m, 1H, H-4'), 4.29 (t, 2H, NO—CH$_2$), 2.89 (t, 2H, NOCH$_2$—CH$_2$), 2.83-2.89 (m, 1H, 5'-CH$_2$), 2.72-2.79 (m, 1H, 5'-CH$_2$), 2.40 (s, 3H, N—CH$_3$), 1.62 and 1.40 (2s, 6H, C(CH$_3$)$_2$).

Example 29

5'-[(2-Aminooxyethyl)methylamino]-5'-deoxyadenosine sulfate (1:1 salt) (12). A solution of 11 (373 mg, 0.73 mmol) in 1N H$_2$SO$_4$ (5 mL) was heated at 60° C. for 3 h. The reaction mixture was neutralized with NaHCO$_3$ and lyophilized. The compound was extracted with EtOH (2×20 mL) and concentrated to dryness. The residue was purified by column chromatography, eluting with 77:20:3 chloroform:methanol:NH$_4$OH). The desired fractions were collected, concentrated, and dried in vacuo. The product was dissolved in 10 mL of EtOH and 1N H$_2$SO$_4$ was added dropwise with cooling to precipitate the salt, which was filtered and washed with EtOH and dried in vacuo: yield 100 mg; MS: m/z 340 (M+H)$^+$; $^1$HNMR (DMSO-d$_6$) δ 8.42 (s, 1H, H-8), 8.25 (s, 1H, H-2), 7.68 (bs, 2H, 6-NH$_2$), 5.99 (d, 1H, H-1', $J_{1',2'}$=5.3 Hz), 5.67 (t, 1H, H-2', $J_{2',3'}$=4.6 Hz), 4.33-4.39 (bm, 1H, H-4'), 4.22 (t, 1H, H-3', $J_{3',4'}$=4.7 Hz), 4.06 (bt, 2H, NH$_2$O—CH$_2$), 3.63-3.71 (dd, 1H, 5'-CH$_2$), 3.52-3.3.59 (bdd, 1H, 5'-CH$_2$), 3.43 (bm, 2H, N(CH$_3$)—CH$_2$), 2.84 (s, 3H, N—CH$_3$); UV $\lambda_{max}$, nm, pH 1, 258.2 (∈ 14,300), pH 7, 259 (∈ 14,600), pH 13, 259 (∈ 15,500). Anal. (C$_{13}$H$_{21}$N$_7$O$_4$.1.0H$_2$SO$_4$. 0.5C$_2$H$_5$OH.1.0H$_2$O) C, H, N.

Example 30

5'-[(2-Carboethoxyethyl)methylamino]-5'-deoxy-8-methyladenosine (13a). A mixture of 4a (500 mg, 1.69 mmol), ethyl 3-chloropropionate (270 mg, 1.97 mmol), DIEA (109 mg, 0.14 mL, 0.84 mmol), and DMF (5 mL) was heated at 60° C. for 2 days. Starting material remained but since the solution was getting darker, heating was stopped. The reaction mixture was concentrated to dryness. The product was purified by column chromatography (7:1:0.1 chloroform:methanol:NH$_4$OH) to give a sticky solid: yield 210 mg (31%); MS m/z 395 (M+H)$^+$; $^1$HNMR (DMSO-d$_6$) δ 8.08 (s, 1H, H-2), 7.11 (bs, 2H, 6-NH$_2$), 5.74 (d, 1H, H-1', $J_{1',2'}$=5.6 Hz), 5.33 (bd, 1H, OH-2'), 5.16 (bd, 1l1, OH-3'), 5.12 (bdd, 1H, H-2', $J_{1',2'}$=5.6 Hz, $J_{2',3'}$=5.5 Hz), 4.21 (bdd, 1H, H-3', $J_{2',3'}$=5.5 Hz, $J_{3',4'}$=4.3 Hz), 4.01 (q, 2H, OCH$_2$CH$_3$), 3.91-4.00 (m, 1H, H-4'), 2.70-2.77 (m, 1H, 5'-CH$_2$), 2.54-2.66 (m, 3H, 5'-CH$_2$, CO—CH$_2$), 2.53 (s, 3H, 8-CH$_3$), 2.38 (t, 2H, N(CH$_3$)—CH$_2$), 2.16 (bs, 3H, N—CH$_3$), 1.15 (t, 3H, OCH$_2$CH$_3$).

Example 31

5'-[(2-Carboethoxyethyl)methylamino]-5'-deoxy-8-ethyladenosine (13b). Compound 13b was prepared by the same procedure as described for the preparation of 13a using 4b (260 mg, 0.84 mmol), ethyl 3-chloropropionate (138 mg, 1.0 mmol), DIEA (53 mg, 0.07 mL, 0.41 mmol), and DMF (4 mL). After column chromatography (elution with 7:1:0.1 chloroform:methanol:NH$_4$OH), a glassy sticky solid was obtained: yield 153 mg (44%), MS: m/z 409 (M+H)$^+$; $^1$HNMR (DMSO-d$_6$) δ 8.08 (s, 1H, H-2), 7.10 (bs, 2H, 6-NH$_2$), 5.71 (d, 1H, H-1', $J_{1',2'}$=5.5 Hz), 5.32 (bd, 1H, OH-2', $J_{2'-2'OH}$=5.0 Hz), 5.16 (bd, 1H, OH-3', $J_{3'-3'OH}$=5.1 Hz), 5.12 (ddd, 1H, H-2', $J_{1',2'}$=5.5 Hz, $J_{2',3'}$=5.7 Hz, $J_{2'-2'OH}$=5.0 Hz), 4.14 (ddd, 1H, H-3', $J_{2',3'}$=5.7 Hz, $J_{3',4'}$=4.1 Hz, $J_{3'-3'OH}$=5.1 Hz), 4.01 (q, 2H, OCH$_2$CH$_3$), 3.91-3.98 (m, 1H, H-4'), 2.87 (q, 2H, CH$_2$ of 8-Et), 2.71-2.79 (m, 1H, 5'-CH$_2$), 2.51-2.65 (m, 3H, 5'-CH$_2$, CO—CH$_2$), 2.38 (t, 2H, N(CH$_3$)—CH$_2$), 2.16 (bs, 3H, N—CH$_3$), 1.30 (t, 3H, CH$_3$ of 8-Et), 1.15 (t, 3H, OCH$_2$CH$_3$).

Example 32

5'-[(Carboethoxymethyl)methyamino]-5'-deoxy-8-methyladenosine (13c). Compound 13c was prepared by the same procedure as described for the preparation of 13a using 4a (415 mg, 1.41 mmol), ethyl chloroacetate (207 mg, 0.18 mL, 1.68 mmol), DIEA (91 mg, 0.12 mL, 0.70 mmol), and DMF (5 mL): yield 204 mg (38%), MS: m/z 381 (M+H)$^+$; $^1$HNMR (DMSO-d$_6$) δ 8.06 (s, 1H, H-2), 7.11 (bs, 2H, 6-NH$_2$), 5.73 (d, 1H, H-1', $J_{1',2'}$=5.4 Hz), 5.33 (bd, 1H, OH-2', $J_{2'-2'OH}$=4.7 Hz), 5.19 (bd, 1H, OH-3', $J_{3'-3'OH}$=4.9 Hz), 5.03 (ddd, 1H, H-2', $J_{1',2'}$=5.4 Hz, $J_{2',3'}$=5.7 Hz, $J_{2'-2'OH}$=4.7 Hz), 4.17 (ddd, 1H, H-3', $J_{2',3'}$=5.7 Hz, $J_{3',4'}$=4.4 Hz, $J_{3'-3'OH}$=4.9 Hz), 4.02 (q, 2H, OCH$_2$CH$_3$), 3.92-3.99 (m, 1H, H-4'), 3.27 (bs, 2H, N(CH$_3$)—CH$_2$), 2.83-2.90 (m, 1H, 5'-CH$_2$), 2.70-

2.79 (m, 1H, 5'-CH$_2$), 2.53 (s, 3H, 8-CH$_3$), 2.31 (s, 3H, N—CH$_3$), 1.13 (t, 3H, OCH$_2$CH$_3$); UV $\lambda_{max}$, nm, pH 1, 258.9 ($\in$ 16,100), pH 7, 260 ($\in$ 15,900), pH 13, 260.1 ($\in$ 16,200). Anal. (C$_{16}$H$_{24}$N$_6$O$_5$.0.5CHCl$_3$.0.3CH$_3$OH) C, H, N.

Example 33

5'-[(2-Carboxamidoethyl)methylamino]-5'-deoxy-8-methyladenosine sulfate (1.5:1 salt) (13d). Compound 13a (89 mg, 0.22 mmol) was dissolved in 5 mL of methanolic ammonia and stirred the solution for 5 days at room temperature. The reaction mixture was concentrated to dryness and purified by column chromatography (4:1:0.2 chloroform:methanol:NH$_4$OH). The desired fractions were collected, concentrated, and dried in vacuo. The product was dissolved in 8 mL of EtOH and 2N H$_2$SO$_4$ was added dropwise. The salt that precipitated out was filtered and washed with EtOH. This product, which was hygroscopic in nature, was dissolved in water (2 mL) and lyophilized to give a white solid: yield 65 mg (55%), MS: m/z 366 (M+H)$^+$; $^1$HNMR (D$_2$O) δ 8.43 (s, 1H, H-2), 6.09 (d, 1H, H-1', J$_{1',2'}$=5.9 Hz), 5.0-5.30 (bm, 1H, H-2'), 4.61-4.70 (bm, 1H, H-4'), 4.51-4.54 (bm, 1H, H-3'), 3.30-3.89 (bm, 5H, N—CH$_3$ and N(CH$_3$)—CH$_2$), 2.96 (bs, 2H, 5'-CH$_2$), 2.77 (bs, 2H, NH$_2$CO—CH$_2$), 2.70 (s, 3H, 8-CH$_3$); UV $\lambda_{max}$, nm, pH 1, 258.4 ($\in$14,900), pH 7, 260.1 ($\in$ 14,900), pH 13, 260.1 ($\in$ 15,300). Anal. (C$_{15}$H$_{23}$N$_7$O$_4$.1.5H$_2$SO$_4$.0.8H$_2$O) C, H, N, S.

Example 34

5'-[(2-Carboxamidoethyl)methyamino]-5'-deoxy-8-ethyladenosine sulfate (1.1:1 salt) (13e). The procedure was the same as reported above for 13d using 13b (149 mg, 0.36 mmol) and methanolic ammonia (5 mL): yield 94 mg (51%), MS: m/z 380 (M+H)$^+$; $^1$HNMR (DMSO-d$_6$) δ 8.08 (s, 1H, H-2), 7.31 (bs, 1H, CO—NH$_2$), 7.10 (bs, 2H, 6-NH$_2$), 6.71 (bs, 1H, CO—NH$_2$), 5.72 (d, 1H, H-1', J$_{1',2'}$=5.4 Hz), 5.31 (d, 1H, OH-2', J$_{2'-2'OH}$=6.2 Hz), 5.16 (d, 1H, OH-3', J$_{3'-3'OH}$=5.5 Hz), 5.09 (ddd, 1H, H-2', J$_{1',2'}$=5.4 Hz, J$_{2',3'}$=5.7 Hz, J$_{2'-2'OH}$=6.2 Hz), 4.17 (ddd, 1H, H-3', J$_{2',3'}$=5.7 Hz, J$_{3',4'}$=4.3 Hz, J$_{3'-3'OH}$=5.5 Hz), 3.92-3.99 (m, 1H, H-4'), 2.87 (q, 2H, 8-CH$_2$CH$_3$), 2.69-2.75 (m, 1H, 5'-CH$_2$), 2.52-2.60 (m, 3H, CO—CH$_2$, 5'-CH$_2$), 2.18 (bs, 2H, N(CH$_3$)—CH$_2$), 2.16 (s, 3H, N—CH$_3$), 1.30 (t, 3H, CH$_3$ of 8-Et); $^1$HNMR (D$_2$O) δ 8.38 (s, 1H, H-2), 6.09 (d, 1H, H-1', J$_{1',2'}$=6.2 Hz), 5.33 (bs, 1H, H-2'), 4.56-4.62 (m, 1H, H-4'), 4.51-4.54 (m, 1H, H-3'), 3.87-3.96 (bm, 2H, NH$_2$CO—CH$_2$), 3.56 (s, 3H, N—CH$_3$), 2.98-3.80 (bm, 2H, 8-CH$_2$CH$_3$), 2.96 (bs, 2H, 5'-CH$_2$), 2.72-2.82 (m, 2H, N(CH$_3$)—CH$_2$), 1.39 (s, 3H, CH$_3$ of 8-Et); UV $\lambda_{max}$, nm, pH 1, 259.4 ($\in$15,200), pH 7, 260.8 ($\in$15,100), pH 13, 260.6 ($\in$ 15,500). Anal. (C$_{16}$H$_{25}$N$_7$O$_4$.1.1H$_2$SO$_4$.1.05H$_2$O) C, H, N, S.

Example 35

5'-[(Carboxamidomethyl)methylamino]-5'-deoxy-8-methyladenosine sulfate (1.45:1 salt) (13f). The same procedure used to prepare 13d was used to prepare 13f using 13c (200 mg, 0.52 mmol) and methanolic ammonia (5 mL): yield 105 mg (39%), MS: m/z 352 (M+H)$^+$; $^1$HNMR (DMSO-d$_6$) δ 8.08 (s, 1H, H-2), 7.11 (bs, 2H, CO—NH$_2$), 7.07 (bs, 2H, 6-NH$_2$), 5.74 (d, 1H, H-1', J$_{1',2'}$=5.2 Hz), 5.34 (d, 1H, OH-2', J$_{2'-2'OH}$=5.9 Hz), 5.21 (d, 1H, OH-3', J$_{3'-3'OH}$=5.7 Hz), 4.97 (ddd, 1H, H-2', J$_{1',2'}$=5.2 Hz, J$_{2',3'}$=5.5 Hz, J$_{2'-2'OH}$=5.9 Hz), 4.21 (ddd, 1H, H-3', J$_{2',3'}$=5.5 Hz, J$_{3',4'}$=5.2 Hz, J$_{3'-3'OH}$=5.7 Hz), 3.94-4.01 (m, 1H, H-4'), 2.94 (d, 1H, N(CH$_3$)—CH$_2$, J=15.7 Hz), 2.88 (d, 1H, N(CH$_3$)—CH$_2$, J=15.7 Hz), 2.75-2.80 (m, 1H, 5'-CH$_2$), 2.63-2.70 (m, 1H, 5'-CH$_2$), 2.53 (s, 3H, 8-CH$_3$), 2.23 (s, 3H, N—CH$_3$), $^1$HNMR (D$_2$O) δ 8.40 (s, 1H, H-2), 6.08 (d, 1H, H-1', J$_{1',2'}$=4.8 Hz), 5.01 (t, 1H, H-2', J$_{2',3'}$=5.2 Hz), 4.60 (t, 1H, H-3', J$_{3',4'}$=4.9 Hz), 4.50-4.59 (m, 1H, H-4'), 4.03-4.17 (m, 2H, NH$_2$CO—CH$_2$), 3.82-3.92 (m, 1H, 5'-CH$_2$), 3.68-3.76 (m, 1H, 5'-CH$_2$), 3.03 (s, 31-1, N—CH$_3$), 2.70 (s, 3H, 8-CH$_3$); UV $\lambda_{max}$, nm, pH 1, 259 ($\in$ 15,900), pH 7, 259.7 ($\in$ 16,100), pH 13, 260.2 ($\in$ 16,100). Anal. (C$_{14}$H$_{21}$N$_7$O$_4$.1.45H$_2$SO$_4$.0.2C$_2$H$_5$OH.1.3H$_2$O) C, H, N, S.

Example 36

5'-[(2-Carboethoxyethyl)methylamino]-5'-deoxyadenosine (13g). The general procedure previously described for 13a was used to prepare 13g using 4h$^{47}$ (400 mg, 1.42 mmol), ethyl 3-chloropropionate (214 mg, 1.56 mmol), DIEA (92 mg, 0.12 mL, 0.71 mmol), and DMF (5 mL). The reaction mixture was heated at 60° C. for 2 days. The product was purified by column chromatography (7:1 chloroform:methanol) to give a solid: yield 102 mg (19%); MS m/z 381 (M+H)$^+$.

Example 37

5'-Deoxy-5'-[(carboethoxyethyl)methylamino]-2',3'-O-isopropylideneadenosine (13h). To compound 4g (380 mg, 1.18 mmol) in anhydrous CH$_3$CN (5 mL) was added ethyl 3-chloropropionate (195 mg, 0.18 mL, 1.42 mmol) and diisopropylethylamine (153 mg, 0.2 mL, 1.18 mmol) and the reaction mixture was stirred at 75-80° C. for 72 h under nitrogen. The reaction mixture was evaporated to dryness and the residue was purified by column chromatography (silica gel 230-400 mesh, elution with 9:1 methylene chloride:methanol). The desired fractions were combined, concentrated, and dried in vacuo: yield 260 mg (52%), MS: m/z 421 (M+H)$^+$

Example 38

5'-[(Carboxamidoethyl)methylamino]-5'-deoxy-2',3'-O-isopropylideneadenosine (13i). A mixture of 13h (80 mg, 0.19 mmol) in saturated methanolic ammonia (15 mL) was stirred for 12 days at room temperature. The resulting solution was concentrated to dryness and the residue was purified by column chromatography (elution with 9:1:0.1 methylene chloride:methanol:NH$_4$OH). The desired fractions were combined, concentrated, and dried in vacuo: yield 40 mg (55%), MS: m/z 392 (M+H)$^+$

Example 39

5'-[(2-Carboxamidoethyl)methylamino]-5'-deoxyadenosine sulfate (1.9:1 salt) (13j). Compound 13i (20 mg) was dissolved in 1N H$_2$SO$_4$ (2 mL) and the solution was stirred at room temperature for 36 h. The reaction mixture was concentrated to 0.5 mL, absolute ethanol (3 mL) was added to the solution to produce a slight turbidity and the mixture was chilled at 0° C. The solid was filtered, washed with ethanol and dried under high vacuum: yield 15 mg (51%), MS: m/z 352 (M+H)$^+$; $^1$HNMR (DMSO-d$_6$) δ 8.64 (s, 1H, H-8), 8.43 (s, 1H, H-2), 7.59 (bs, 1H, NH$_2$), 7.17 (bs, 1H, NH$_2$), 6.02 (bdd, 1H, H-1', J$_{1',2'}$=3.4 Hz), 4.65 (t, 1H, H-2', J$_{2',3'}$=6.4 Hz), 4.17-4.21 (bm, 1H, H-3'), 3.34-3.42 (bm, 1H, H-4'), 3.52-3.67 (bm, 4H, 5'-CH$_2$, N(CH$_3$)—CH$_2$), 2.80 (bs, 3H, N—CH$_3$), 2.54-2.60 (bm, 2H, CO—CH$_2$); UV $\lambda_{max}$, nm, pH 1, 256.3 ($\in$ 15,200), pH 7, 258.5 (∈ 15,400), pH 13, 259.6 (∈ 16,100). Anal. ($C_{14}H_{21}N_7O_4 \cdot 1.9H_2SO_4 \cdot 1.6H_2O$) C, H, N, S.

Example 40

5'-Deoxy-5'-[(2-hydrazinocarbonylethyl)methylamino]-8-methyladenosine sulfate (2:1 salt) (13k). Compound 13a (115 mg, 0.29 mmol) was dissolved in 10 mL of anhydrous ethanol and hydrazine monohydrate (73 mg, 0.07 mL, 1.46 mmol) was added to the solution. The reaction mixture was heated to reflux overnight. Hydrazine monohydrate (0.07 mL) was added again and heating was continued overnight. The resulting solution was evaporated to dryness. The crude product was purified by column chromatography (4:1:0.5 chloroform:methanol:$NH_4OH$). The desired fractions were collected, concentrated, and dried in vacuo to yield a sticky solid. The product was dissolved in 8 mL of EtOH and 2N $H_2SO_4$ was added drop wise. The salt that was precipitated out was filtered and washed with EtOH. This salt, which was hygroscopic in nature, was dissolved in water (2 mL) and lyophilized to give a white solid: yield 71 mg (65%), MS: m/z 381 (M+H)$^+$; $^1$HNMR ($D_2O$) δ 8.44 (s, 1H, H-2), 6.09 (d, 1H, H-1', $J_{1',2'}$=5.6 Hz), 5.10 (dd, 1H, H-2', $J_{2',3'}$=4.5 Hz), 4.53-4.62 (bm, 2H, H-3', H-4'), 3.86-3.94 (m, 1H, 5'-$CH_2$), 3.52-3.66 (m, 3H, 5'-$CH_2$, N($CH_3$)—$CH_2$), 2.95 (s, 3H, N—$CH_3$), 2.86 (t, 2H, NHCO—$CH_2$), 2.70 (s, 3H, 8-$CH_3$); UV $\lambda_{max}$, nm, pH 1, 258.4 (∈ 15,000), pH 7, 259.3 (∈ 15,200), pH 13, 260.4 (∈ 15,700). Anal. ($C_{15}H_{24}N_8O_4 \cdot 2.0H_2SO_4 \cdot 2.7H_2O$) C, H, N, S.

Example 41

5'-Deoxy-5'-[(2-hydrazinocarbonylethyl)methylamino]-adenosine sulfate (2:1 salt) (13l). The procedure was the same as reported above for 13k using 13g (95 mg, 0.25 mmol) and hydrazine monohydrate (63 mg, 0.06 mL, 1.25 mmol): yield 39 mg (43%), MS: m/z 367 (M+H)$^+$; $^1$HNMR ($D_2O$) δ 8.47 (s, 1H, H-8), 8.45 (s, 1H, H-2), 6.17 (d, 1H, H-1', $J_{1',2'}$=4.7 Hz), 4.90 (dd, 1H, H-2', $J_{2',3'}$=5.2 Hz), 4.56-4.60 (bm, 1H, H-4'), 4.48 (dd, 1H, H-3', $J_{3',4'}$=5.0 Hz), 3.82 (dd, 1H, 5'-$CH_2$), 3.66 (dd, 1H, 5'-$CH_2$), 3.59 (bt, 2H, N($CH_3$)—$CH_2$), 2.97 (s, 3H, N—$CH_3$), 2.86 (t, 2H, NHCO—$CH_2$); UV $\lambda_{max}$, nm, pH 1, 256.8 (∈ 16,600), pH 7, 258.5 (∈ 16,800), pH 13, 259.5 (∈ 17,600). Anal. ($C_{14}H_{22}N_8O_4 \cdot 2.0H_2SO_4 \cdot 2.0H_2O$) C, H, N.

Example 42

5'-Deoxy-5'-[(hydrazinocarbonylmethyl)methylamino]-8-methyladenosine (13m). The same procedure used to prepare 13k was used to prepare 13m using 13c (167 mg, 0.44 mmol) and hydrazine monohydrate (109 mg, 0.11 mL, 2.18 mmol). After the column it yielded a white solid: yield 154 mg (96%), MS: m/z 367 (M+H)$^+$; $^1$HNMR (DMSO-$d_6$) δ 8.75 (bs, 1H, NH), 8.09 (s, 1H, H-2), 7.10 (bs, 2H, NH—$NH_2$), 5.74 (d, 1H, H-1', $J_{1',2'}$=5.2 Hz), 5.31 (d, 1H, OH-2', $J_{2'-2'OH}$=6.0 Hz), 5.18 (d, 1H, OH-3', $J_{3'-3'OH}$=5.6 Hz), 5.0 (ddd, 1H, H-2', $J_{1',2'}$=5.2 Hz, $J_{2',3'}$=5.7 Hz, $J_{2'-2'OH}$=6.0 Hz), 4.19 (ddd, 1H, H-3', $J_{2',3'}$=5.7 Hz, $J_{3',4'}$=4.9 Hz, $J_{3'-3'OH}$=5.6 Hz), 3.94-3.99 (m, 1H, H-4'), 3.01 (d, 1H, CO—CHaHb, J=15.2 Hz), 2.95 (d, 1H, CO—CHa Hb, J=15.2 Hz), 2.78 (dd, 1H, 5'-$CH_2$), 2.66 (dd, 1H, 5'-$CH_2$), 2.53 (s, 3H, 8-$CH_3$), 2.22 (s, 3H, N—$CH_3$); UV $\lambda_{max}$, nm, pH 1, 258.9 (∈ 15,300), pH 7, 259.3 (∈ 15,600), pH 13, 260.1 (∈ 16,100). Anal. ($C_{14}H_{22}N_8O_4 \cdot 0.2CH_3OH \cdot 0.4H_2O$) C, H, N.

Example 43

5'-[(3-Aminopropyl)methylamino]-5'-deoxy-8-(methylamino)adenosine sulfate (2.4:1 salt) (14a) and 5'-deoxy-8-(methylamino)-5'(3-methylaminopropylamino)adenosine sulfate (2.4:1 salt) (15a). A solution of 3c (175 mg, 0.55 mmol) in 2 mL of N-methyl-1,3-propanediamine was stirred for 4 days at ambient temperature. The mixture was poured into diethyl ether (20 mL). Decantation of the ether layer left an oil, which was purified by column chromatography. The column was eluted with 4:1:0.5 chloroform:methanol:$NH_4OH$. The desired fractions were collected, concentrated, and dried in vacuo yielding two isomers. These separated isomers were dissolved in 6 mL of EtOH and 5 mL of EtOH respectively, and 2N $H_2SO_4$ was added dropwise. The sulfate salts that precipitated out were filtered and washed with EtOH. These salts, which were hygroscopic in nature, were dissolved in water (2 mL) and lyophilized to give white solids: 14a yield 50 mg (15%), MS: m/z 367 (M+H)$^+$; $^1$HNMR (DMSO-$d_6$) δ 7.91 (s, 1H, H-2), 6.90 (bs, 1H, 8$CH_3$—NH), 6.49 (bs, 2H, 6-$NH_2$), 5.70 (d, 1H, H-1', $J_{1',2'}$=4.8 Hz), 4.92 (t, 1H, H-2', $J_{2',3'}$=5.5 Hz), 4.17 (t, 1H, H-3', $J_{3',4'}$=5.2 Hz), 3.89-3.96 (bm, 1H, H-4'), 2.89 (s, 3H, 8NH—$CH_3$), 2.53-2.70 (m, 4H, $NH_2$—$CH_2$, 5'-$CH_2$), 2.38 (t, 2H, N($CH_3$)—$CH_2$), 2.17 (s, 3H, N—$CH_3$), 1.48-1.60 (m, 2H, $NH_2CH_2$—$CH_2$), $^1$HNMR ($D_2O$) δ 8.28 (s, 1H, H-2), 5.87 (d, 1H, H-1', $J_{1',2'}$=5.1 Hz), 5.18 (t, 1H, H-2', $J_{2',3'}$=5.1 Hz), 4.54 (t, 1H, H-3', $J_{3',4'}$=5.1 Hz), 4.46-4.51 (m, 1H, H-4'), 3.01-3.82 (bm, 6H, 5'-$CH_2$, $NH_2$—$CH_2$, N($CH_3$)—$CH_2$), 3.05 (s, 3H, 8NH—$CH_3$), 2.94 (s, 3H, N—$CH_3$), 2.05-2.18 (bm, 2H, $NH_2CH_2$—$CH_2$); UV $\lambda_{max}$, nm, pH 1, 275.5 (∈ 14,500), pH 7, 275 (∈ 17,200), pH 13, 277 (∈ 17,500). Anal. ($C_{15}H_{26}N_8O_3 \cdot 2.4H_2SO_4 \cdot 0.2C_2H_5OH$) C, H, N; 15a yield 29 mg (7%), MS: m/z 367 (M+H)$^+$; $^1$HNMR (DMSO-$d_6$) δ 7.96 (s, 1H, H-2), 7.0 (bs, 1H, 8$CH_3$—NH), 6.57 (bs, 2H, 6-$NH_2$), 5.80 (d, 1H, H-1', $J_{1',2'}$=5.5 Hz), 4.97 (t, 1H, H-2', $J_{2',3'}$=5.5 Hz), 5.4 (bs, 2H, 2',3'-OH's), 4.33 (t, 1H, H-3', $J_{3',4'}$=3.7 Hz), 4.17-4.24 (bm, 1H, H-4'), 3.20-3.50 (m, 2H, 5'-$CH_2$), 3.05-3.85 (m, 4H, NH—$CH_2$), 2.88 (s, 3H, 8NH—$CH_3$), 2.49 (s, 3H, NH—$CH_3$), 1.85-2.0 (bm, 2H, NH$CH_2$—$CH_2$), $^1$HNMR ($D_2O$) δ 8.27 (s, 1H, H-2), 5.86 (d, 1H, H-1', $J_{1',2'}$=5.2 Hz), 5.16 (t, 1H, H-2', $J_{2',3'}$=5.5 Hz), 4.55 (t, 1H, H-3', $J_{3',4'}$=4.5 Hz), 4.36-4.44 (m, 1H, H-4'), 3.47-3.69 (m, 2H, 5'-$CH_2$), 3.22 (t, 2H, NH—$CH_2$), 3.10 (t, 2H, $CH_3$NH—$CH_2$), 3.05 (s, 3H, 8NH—$CH_3$), 2.71 (s, 3H, NH—$CH_3$), 2.04-2.18 (bm, 2H, NH$CH_2$—$CH_2$); UV $\lambda_{max}$, nm, pH 1, 274.1 (∈ 14,300), pH 7, 276 (∈ 17,100), pH 13, 277.1 (∈ 18,700). Anal. ($C_{15}H_{26}N_8O_3 \cdot 2.4H_2SO_4 \cdot 0.2C_2H_5OH$) C, H, N.

Example 44

5'-[(3-Aminopropyl)methylamino]-5'-deoxy-8-phenyladenosine sulfate (2.2:1 salt) (14b) and 5'-deoxy-5'-(3-methylaminopropylamino)-8-phenyladenosine sulfate (1.7:1 salt) (15b). The same procedure as described above for 14a was used to prepare 14b and 15b from 3d (200 mg, 0.55 mmol), and N-methyl-1,3-propanediamine (3 mL) except in this case, after 1 day of stirring at room temperature, the reaction mixture was heated at 65° C. for 2 days. The column was eluted with 4:1:0.2 chloroform:methanol:$NH_4OH$. After the same work up two isomers were obtained: 14b yield 124 mg (34%), MS: m/z 414 (M+H)$^+$; $^1$HNMR (DMSO-$d_6$) δ 8.38 (s, 1H, H-2), 7.61-7.84 (m, 7H, 8-phenyl, 6-$NH_2$), 5.88 (d, 1H, H-1', $J_{1',2'}$=6.3 Hz), 5.17-5.30 (bm, 1H, H-2'), 4.34-4.38 (bm, 1H, H-3'), 4.25-4.31 (bm, 1H, H-4'), 3.10-3.85 (bm, 4H, N($CH_3$)—$CH_2$, 5'-$CH_2$), 2.80-2.94 (m, 2H, $NH_2$—$CH_2$), 2.78 (s, 3H, N—$CH_3$), 1.81-2.0 (bm, 2H, $NH_2CH_2$—$CH_2$); UV $\lambda_{max}$, nm, pH 1, 274.2 (∈ 20,500), pH 7, 275.8 (∈ 16,300), pH 13, 274.5 (∈ 16,400). Anal. ($C_{20}H_{27}N_7O_3 \cdot 2.2H_2SO_4 \cdot 0.1C_2H_5OH \cdot 2.5H_2O$) C, H, N, S; 15b yield 151 mg (42%), MS: m/z 414 (M+H)$^+$; $^1$HNMR (DMSO-$d_6$) δ 8.23 (s, 1H, H-2), 7.0-7.74 (m, 2H, 8-phenyl o-H's), 7.60-7.65 (m, 3H, 8-phenyl m- and p-H's), 7.46 (bs, 2H, 6-$NH_2$), 5.80 (d, 1H, H-1', $J_{1,2}$=6.2 Hz), 5.25 (t, 1H, H-2', $J_{2,3}$=4.9 Hz), 5.5-6.0 (m, 2H, NH's), 4.29-4.35 (bm, 1H, H-3'), 4.12-4.20 (m, 1H, H-4'), 3.40-3.47 (m, 1H, 5'-$CH_2$), 3.19-3.25 (m, 1H, 5'-$CH_2$), 2.94 (m, 4H, NH—$CH_2$, $CH_3$NH—$CH_2$), 2.54 (s, 3H, NH—$CH_3$), 1.80-1.95 (bm, 2H, NH$CH_2$—$CH_2$); UV $\lambda_{max}$, nm, pH 1, 275.5 (∈ 20,600), pH 7, 274.9 (∈ 16,200), pH 13, 274.9 (∈ 16,300). Anal. ($C_{20}H_{22}N_2O_3 \cdot 1.7H_2SO_4 \cdot 0.05C_2H_5OH \cdot 3.3H_2O$) C, H, N, S.

Example 45

5'-[(3-Aminopropyl)methylamino]-5'-deoxy-2',3'-O-isopropylideneadenosine (14c). A mixture of 3h[44] (1.0 g, 2.60 mmol) and N-methyl-1,3-propanediamine (1.35 mL, 13.0 mmol) were stirred overnight under an argon atmosphere. The reaction mixture was concentrated to dryness and the crude was purified by column chromatography using chloroform:methanol:$NH_4OH$ (6:1:0.1) as eluent. The desired fractions were combined, concentrated, and dried in vacuo to give a semi-solid. This material was dissolved in 3 mL of water and lyophilized: yield 361 mg (37%), MS: m/z 378 (M+H)$^+$; $^1$HNMR (DMSO-$d_6$) δ 8.33 (s, 1H, H-8), 8.17 (s, 1H, H-2), 7.33 (bs, 2H, 6-$NH_2$), 6.13 (d, 1H, H-1', $J_{1',2'}$=2.3 Hz), 5.49 (dd, 1H, H-2', $J_{2',3'}$=4.0 Hz), 4.94 (dd, 1H, H-3', $J_{3',4'}$=2.9 Hz), 4.21-4.27 (m, 1H, H-4'), 2.52-2.58 (m, 2H, $NH_2$—$CH_2$), 2.26-2.38 (m, 4H, 5'-$CH_2$, N($CH_3$)—$CH_2$), 2.12 (s, 3H, N—$CH_3$), 1.53 and 1.33 (2s, 6H, C($CH_3$)$_2$), 1.37-1.47 (m, 2H, $NH_2CH_2$—$CH_2$).

Example 46

5'-[(3-Aminopropyl)methylamino]-5'-deoxyadenosine sulfate (2:1 salt) (14d). The procedure described for 13j was used to prepare 14d from 14c (200 mg, 0.53 mmol): yield 121 mg (41%), MS: m/z 338 (M+H)$^+$; $^1$HNMR (DMSO-$d_6$) δ 8.47 (bs, 1H, H-8), 8.29 (bs, 1H, H-2), 7.0-10.0 (broad peaks, $NH_2$s+$H_2SO_4$), 5.97 (d, 1H, H-1', $J_{1',2'}$=4.7 Hz), 5.70 (bs, 1H, 2'-OH), 5.56 (bs, 1H, 3'-OH), 4.72 (bt, 1H, H-2'), 4.30 (bm, 1H, H-4'), 4.21 (bt, 1H, H-3'), 3.30-3.70 (bm, 2H, 5'-$CH_2$), 3.08 (bs, 2H, N($CH_3$)—$CH_2$), 2.83 (bm, 2H, $NH_2$—$CH_2$), 2.70 (bs, 3H, N—$CH_3$), 1.84-1.92 (m, 2H, $NH_2CH_2$—$CH_2$); UV $\lambda_{max}$, nm, pH 1, 257 (∈ 14,700), pH 7, 259.2 (∈ 15,000), pH 13, 260 (∈ 15,300). Anal. ($C_{14}H_{23}N_7O_3 \cdot 2.0H_2SO_4 \cdot 0.25C_2H_5OH \cdot 0.7H_2O$) C, H, N.

Example 47

5'-[(2-Aminoethyl)methylamino]-5'-deoxyadenosine (14e) and 5'-deoxy-5'-(2-methylaminoethylamino)adenosine (15c). A mixture of 3g[43] (1.0 g, 3.5 mmol) and N-methylethylenediamine (8 mL) was stirred at room temperature for 12 days. The reaction mixture was poured into diethyl ether (50 mL). The ether layer was decanted and the resulting syrup was purified by column chromatography (silica gel 230-400 mesh, elution with 4:1:0.5 chloroform:methanol:$NH_4OH$). The desired fractions were combined, concentrated, and dried in vacuo to give the two isomers: yield (14e) 576 mg (51%), MS: m/z 324 (M+H)$^+$; $^1$HNMR (DMSO-$d_6$) δ 8.35 (s, 1H, H-8), 8.15 (s, 1H, H-2), 7.27 (bs, 2H, 6-$NH_2$), 5.85 (d, 1H, H-1', $J_{1',2'}$=5.3 Hz), 4.64 (dd, 1H, H-2', $J_{2',3'}$=5.3 Hz), 4.11 (dd, 1H, H-3', $J_{3',4'}$=4.3 Hz), 3.95-4.0 (m, 1H, H-4'), 2.90-3.60 (bs, 4H, 2',3'-OHs+NHs), 2.70 (dd, 1H, 5'-$CH_2$), 2.50-2.60 (bm, 3H, 5'-$CH_2$, N($CH_3$)—$CH_2$), 2.36 (t, 2H, $NH_2$—$CH_2$), 2.19 (s, 3H, N—$CH_3$); UV $\lambda_{max}$, nm, pH 1, 256.9 (∈14,100), pH 7, 259.5 (∈ 14,700), pH 13, 259.2 (∈ 15,300). Anal. ($C_{13}H_{21}N_7O_3 \cdot 0.25CHCl_3 \cdot 0.5H_2O$) C, H, N; yield (15c) 323 mg (29%), MS: m/z 324 (M+H)$^+$; $^1$HNMR (DMSO-$d_6$) δ 8.35 (s, 1H, H-8), 8.14 (s, 1H, H-2), 7.28 (bs, 2H, 6-$NH_2$), 5.84 (d, 1H, H-1', $J_{1',2'}$=5.9 Hz), 4.69 (dd, 1H, H-2', $J_{2',3'}$=5.3 Hz), 4.12 (dd, 1H, H-3', $J_{3',4'}$=3.5 Hz), 3.94-3.99 (m, 1H, H-4'), 2.90-3.60 (bs, 4H, 2', 3'-OHs+NHs), 2.80 (dd, 1H, 5'-$CH_2$), 2.73 (dd, 1H, 5'-$CH_2$), 2.50-2.62 (bm, 4H, $NHCH_3$—$CH_2$, NH—$CH_2$), 2.25 (s, 3H, NH—$CH_3$); UV $\lambda_{max}$, nm, pH 1, 256.4 (∈ 13,900), pH 7, 259 (∈ 13,900), pH 13, 259.8 (∈ 14,000). Anal. ($C_{13}H_{21}N_7O_3 \cdot 0.05CH_3OH \cdot 0.1H_2O$) C, H, N.

Example 48

5'-[(2-Aminoethyl)methylamino]-5'-deoxy-8-methyladenosine (14f) and 5'-deoxy-8-methyl-5'-(2-methylaminoethylamino)adenosine (15d). The procedure described above for 14e/15c was used to prepare 14f/15d from 3a (300 mg, 1.0 mmol) and N-methylethylenediamine (3 mL): yield (14f) 69 mg (18.3%), MS: m/z 338 (M+H)$^+$; $^1$HNMR (DMSO-$d_6$) δ 8.08 (s, 1H, H-2), 7.11 (bs, 2H, 6-$NH_2$), 5.74 (d, 1H, H-1', $J_{1',2'}$=5.4 Hz), 5.31 (bs, 1H, 2'-OH), 5.04 (dd, 1H, H-2', $J_{2',3'}$=5.6 Hz), 4.17 (dd, 1H, H-3', $J_{3',4'}$=4.5 Hz), 4.08 (bs, 1H, 3'-OH), 3.93-3.98 (m, 1H, H-4'), 2.70 (dd, 1H, 5'-$CH_2$), 2.53-2.57 (bm, 3H, 5'-$CH_2$, N($CH_3$)—$CH_2$), 2.53 (s, 3H, 8-$CH_3$), 2.30-2.35 (m, 2H, $NH_2$—$CH_2$), 2.16 (s, 3H, N—$CH_3$); UV $\lambda_{max}$, nm, pH 1, 258.5 (∈15,600), pH 7, 259.1 (∈16,000), pH 13, 260 (∈ 16,200). Anal. ($C_{14}H_{23}N_7O_3 \cdot 0.5 CH_3OH \cdot 0.3H_2O$) C, H, N; yield (15d) 58 mg (15.4%), MS: m/z 338 (M+H)$^+$; $^1$HNMR (DMSO-$d_6$) δ 8.07 (s, 1H, H-2), 7.12 (bs, 2H, 6-$NH_2$), 5.72 (d, 1H, H-1', $J_{1',2'}$=6.4 Hz), 5.27 (bs, 1H, 2'-OH), 5.02 (dd, 1H, H-2', $J_{2',3'}$=5.4 Hz), 4.17 (dd, 1H, H-3', $J_{3',4'}$=3.1 Hz), 3.94-3.99 (m, 1H, H-4'), 2.80 (dd, 1H, 5'-$CH_2$), 2.74 (dd, 1H, 5'-$CH_2$), 2.54-2.63 (bm, 4H, $NHCH_3$—$CH_2$, NH—$CH_2$), 2.54 (s, 3H, 8-$CH_3$), 2.24 (s, 3H, NH—$CH_3$); UV $\lambda_{max}$, nm, pH 1, 258.4 (∈ 15,400), pH 7, 259.5 (∈ 15,400), pH 13, 260 (∈ 15,900). Anal. ($C_{14}H_{23}N_7O_3 \cdot 0.4CH_3OH \cdot 0.7H_2O$) C, H, N.

Example 49

5'-Deoxy-2',3'-O-isopropylidene-5'-[(3-phthalimidopropyl)methylamino]-8-methyladenosine (16a). To a cold solution of compound 2e (500 mg, 1.5 mmol) in anhydrous pyridine (2 mL) was added methanesulfonyl chloride (196 mg, 0.13 mL, 1.7 mmol) and the solution was stirred for 2 h at 0° C. The reaction mixture was concentrated to dryness to afford crude 3e. Methylamine (33% solution in EtOH, 12 mL) was added to this crude mixture and the solution was stirred for 3 days at room temperature. The reaction mixture was evaporated to dryness. The resulting crude 4e was dissolved in anhydrous DMF (3 mL), DIEA (0.07 mL) and N-(3-bromopropyl)phthalimide (502 mg, 1.87 mmol) were added and the reaction mixture was heated overnight at 60° C. The solution was evaporated to dryness and the residue was dissolved in $CHCl_3$ (10 mL), washed with water, dried over $Na_2SO_4$, and concentrated to dryness. The resulting syrup was purified by column chromatography. The column was eluted with 97:3 chloroform:methanol. Desired fractions were combined, concentrated and dried in vacuo: yield 108 mg (13%); MS m/z 522 (M+H)$^+$; $^1$HNMR (CDCl$_3$) δ 8.26 (s, 1H, H-2), 7.82-7.86 (m, 2H, phthalimido aromatic H's), 7.69-7.73 (m, 2H, phthalimido aromatic H's), 5.98 (d, 1H, H-1', $J_{1',2'}$=1.8 Hz), 5.76 (dd, 1H, H-2', $J_{1',2'}$=1.8 Hz, $J_{2',3'}$=6.5 Hz), 5.38 (bs, 2H, 6-$NH_2$), 5.10 (dd, 1H, H-3', $J_{2',3'}$=6.5 Hz, $J_{3',4'}$=3.5 Hz), 4.26-4.32 (m, 1H, H-4'), 3.60-3.76 (m, 2H, N—$CH_2$), 2.64 (s, 3H, 8-$CH_3$), 2.58-2.63 (m, 1H, 5'-$CH_2$), 241-2.48 (m, 1H, 5'-CH$_2$), 2.38 (t, 2H, N(CH$_3$)—CH$_2$), 2.21 (s, 3H, N—CH$_3$), 1.68-1.80 (m, 2H, NCH$_2$—CH$_2$), 1.61 and 1.40 (2s, 6H, C(CH$_3$)$_2$).

Example 50

5'-Deoxy-2',3'-O-isopropylidene-5'-[(3-phthalimidopropyl)methylamino]-8-ethyladenosine (16b). The same procedure as described for 16a was used to prepare 16b from 2f (600 mg, 1.78 mmol), MsCl (225 mg, 0.15 mL, 1.96 mmol), methylamine (12 mL), and N-(3-bromopropyl)phthalimide (553 mg, 2.06 mmol): yield 81 mg (8.5%), MS: m/z 536 (M+H)$^+$; $^1$HNMR (CDCl$_3$) δ 8.26 (s, 1H, H-2), 7.81-7.86 (m, 2H, phthalimido aromatic H's), 7.67-7.72 (m, 2H, phthalimido aromatic H's), 5.98 (d, 1H, H-1', J$_{1',2'}$=2.0 Hz), 5.75 (dd, 1H, H-2', J$_{1',2'}$=2.0 Hz, J$_{2',3'}$=6.5 Hz), 5.37 (bs, 2H, 6-NH$_2$), 5.12 (dd, 1H, H-3', J$_{2',3'}$=6.5 Hz, J$_{3',4'}$=3.5 Hz), 4.25-4.33 (m, 1H, H-4'), 3.61-3.75 (m, 2H, N—CH$_2$), 2.94 (q, 2H, CH$_2$ of 8-Et), 2.62-2.68 (m, 1H, 5'-CH$_2$), 243-2.49 (m, 1H, 5'-CH$_2$), 2.38 (bt, 2H, N(CH$_3$)—CH$_2$), 2.22 (s, 3H, N—CH$_3$), 1.70-1.80 (m, 2H, NCH$_2$—CH$_2$), 1.60 and 1.40 (2s, 6H, C(CH$_3$)$_2$), 1.42 (t, 3H, CH$_3$ of 8-Et).

Example 51

5'-Deoxy-2',3'-O-isopropylidene-5'-[(3-aminopropyl)methylamino]-8-methyladenosine (17a). To a boiling solution of 16a (100 mg, 0.19 mmol) in 3 mL of ethanol was added hydrazine monohydrate (50 mg, 0.048 mL, 0.99 mmol) and the solution was heated to refluxed for 1 h. The reaction mixture was cooled down to room temperature and the solid was filtered and washed with ethanol. The filtrate was evaporated to dryness. This crude product was purified by column chromatography using chloroform:methanol: NH$_4$OH (7:1:0.2) for elution: yield 69 mg (92%), MS: m/z 392 (M+H)$^+$; $^1$HNMR (DMSO-d$_6$) δ 8.12 (s, 1H, H-2), 7.18 (bs, 2H, 6-NH$_2$), 6.06 (d, 1H, H-1', J$_{1',2'}$=1.9 Hz), 5.79 (dd, 1H, H-2', J$_{1',2'}$=1.9 Hz, J$_{2',3'}$=6.3 Hz), 5.0 (dd, 1H, H-3', J$_{2',3'}$=6.3 Hz, J$_{3',4'}$=3.1 Hz), 4.15-4.21 (m, 1H, H-4'), 2.56 (s, 3H, 8-CH$_3$), 2.40-2.50 (m, 2H, N(CH$_3$)—CH$_2$), 2.13-2.31 (bm, 4H, NH$_2$—CH$_2$, 5'-CH$_2$), 2.07 (s, 3H, N—CH$_3$), 1.53 and 1.33 (2s, 6H, C(CH$_3$)$_2$), 1.22-1.32 (m, 2H, NH$_2$CH$_2$—CH$_2$).

Example 52

5'-Deoxy-2',3'-O-isopropylidene-5'-[(3-aminopropyl)methylamino]-8-ethyladenosine (17b). Compound 17b was prepared by the same procedure as reported for 17a using 16b (76 mg, 0.14 mmol) and hydrazine monohydrate (38 mg, 0.036 mL, 0.76 mmol): yield 47 mg (82%), MS: m/z 406 (M+H)$^+$; $^1$HNMR (DMSO-d$_6$) δ 8.12 (s, 1H, H-2), 7.16 (bs, 2H, 6-NH$_2$), 6.03 (d, 1H, H-1', J$_{1',2'}$=2.0 Hz), 5.76 (dd, 1H, H-2', J$_{1',2'}$=2.0 Hz, J$_{2',3'}$=6.4 Hz), 5.01 (dd, 1H, H-3', J$_{2',3'}$=6.4 Hz, J$_{3',4'}$=3.0 Hz), 4.15-4.22 (m, 1H, H-4'), 2.87-2.94 (bm, 2H, 5'-CH$_2$), 2.38-2.53 (m, 2H, CH$_2$ of 8-Et), 2.13-2.34 (m, 4H, N(CH$_3$)—CH$_2$, NH$_2$—CH$_2$), 2.08 (s, 3H, N—CH$_3$), 1.53 and 1.33 (2s, 6H, C(CH$_3$)$_2$), 1.22-1.39 (m, 2H, NH$_2$CH$_2$—CH$_2$), 1.31 (t, 3H, CH$_3$ of 8-Et).

Example 53

5'-[(3-Aminopropyl)methylamino]-5'-deoxy-8-methyladenosine sulfate (2:1 salt) (17c). Compound 17a (66 mg, 0.168 mmol) was dissolved in 2 mL of 1N H$_2$SO$_4$ and stirred overnight. To this solution was added ethanol (10 mL), causing a fine solid to separate. The solvent was decanted, the compound was dissolved in water (1 mL) and 15 mL of ethanol was added. The resulting solid was dissolved in water (2 mL) and lyophilized to give a white solid: yield 66 mg (67%), MS: m/z 352 (M+H)$^+$; $^1$HNMR (DMSO-d$_6$) δ 8.16 (s, 1H, H-2), 7.74 (bs, 2H, CH$_2$—NH$_2$), 7.24 (bs, 2H, 6-NH$_2$), 5.84 (d, 1H, H-1', J$_{1',2'}$=6.0 Hz), 5.62 (bs, 2H, 2',3'-OH's), 4.98 (t, 1H, H-2', J$_{2,3}$=4.4 Hz), 4.29-4.36 (bm, 1H, H-4'), 4.23 (t, 1H, H-3'), 3.40-3.68 (bm, 2H, 5'-CH$_2$), 2.99-3.19 (bm, 2H, N(CH$_3$)—CH$_2$), 2.83 (t, 2H, NH$_2$—CH$_2$), 2.70 (bs, 3H, N—CH$_3$), 2.55 (s, 3H, 8-CH$_3$), 1.80-1.93 (m, 2H, NH$_2$CH$_2$—CH$_2$); UV λ$_{max}$, nm, pH 1, 258.7 (∈ 14,900), pH 7, 259.5 (∈ 15,100), pH 13, 260.7 (∈ 15,300). Anal. (C$_{15}$H$_{25}$N$_7$O$_3$.2.0H$_2$SO$_4$.2.5H$_2$O) C, H, N, S.

Example 54

5'-[(3-Aminopropyl)methylamino]-5'-deoxy-8-ethyladenosine sulfate (2.5:1 salt) (17d). The procedure described for 17c was used to prepare 17d from 17b (44 mg, 0.108 mmol). In this case after the addition of EtOH a fine solid came out which was collected by centrifugation. It was then dissolved in water (2 mL) and lyophilized: yield 30 mg (69%), MS: m/z 366 (M+H)$^+$; $^1$HNMR (DMSO-d$_6$) δ; 8.15 (s, 1H, H-2), 7.68 (bs, 2H, CH$_2$—NH$_2$), 7.21 (bs, 2H, 6-NH$_2$), 5.82 (d, 1H, H-1', J$_{1',2'}$=6.0 Hz), 5.61 (bs, 2H, 2',3'-OH's), 5.04 (t, 1H, H-2'), 4.19-4.27 (bm, 2H, H-3', 4'), 3.22-3.43 (bm, 4H, 5'-CH$_2$, N(CH$_3$)—CH$_2$), 2.90 (q, 2H, 8CH$_2$CH$_3$), 2.81 (t, 2H, NH$_2$—CH$_2$), 2.50 (bs, 3H, N—CH$_3$), 1.73-1.88 (bm, 2H, NH$_2$CH$_2$—CH$_2$), 1.32 (t, 3H, 8CH$_2$CH$_3$); UV λ$_{max}$, nm, pH 1, 259.3 (∈ 15,100), pH 7, 260.5 (∈ 15,100), pH 13, 260.3 (∈ 15,100). Anal. (C$_{16}$H$_{27}$N$_7$O$_3$.2.5H$_2$SO$_4$.2.5H$_2$O) C, H, N.

Example 55

5'-Deoxy 5'-[(2-guanidinoethyl)methylamino]adenosine (18a). To a stirred solution of 14e (218 mg, 0.67 mmol) and 1H-pyrazole-1-carboxamidine hydrochloride[50] (196 mg, 1.34 mmol) in anhydrous DMF (5 mL) was added DIEA (479 mg, 0.65 mL, 3.7 mmol) under nitrogen at 5° C. Stirring was continued at room temperature overnight. The reaction mixture was concentrated to dryness and the product was purified by column chromatography (silica gel 230-400 mesh, elution with 4:1:0.3 chloroform:methanol:NH$_4$OH). The desired fractions were combined, concentrated, and dried in vacuo to give a white solid: yield 219 mg (89%), MS: m/z 366 (M+H)$^+$; $^1$HNMR (DMSO-d$_6$) δ 8.34 (s, 1H, H-8), 8.15 (s, 1H, H-2), 7.48, 7.37, 7.28 (bs, NHs), 5.87 (d, 1H, H-1', J$_{1',2'}$=5.2 Hz), 5.50 (d, 1H, 2'-OH, J$_{2'-2'OH}$=5.7 Hz), 5.28 (d, 1H, 3'-OH, J$_{3'-3'OH}$=4.5 Hz), 4.65 (ddd, 1H, H-2', J$_{1',2'}$=5.2 Hz, J$_{2',3'}$=5.1 Hz, J$_{2'-2'OH}$=5.7 Hz), 4.12 (ddd, 1H, H-3', J$_{2',3'}$=5.1 Hz, J$_{3',4'}$=4.6 Hz, J$_{3'-3'OH}$=4.5 Hz), 4.0-4.10 (bm, 1H, H-4'), 3.30-3.50 (bm, 2H, 5'-CH$_2$), 3.12-3.28 (bm, 2H, NH—CH$_2$), 2.55-2.65 (bm, 2H, N(CH$_3$)—CH$_2$), 2.25 (bs, 3H, N—CH$_3$); UV λ$_{max}$, nm, pH 1, 256.3 (∈ 10,900), pH 7, 259 (∈ 11,300), pH 13, 259 (∈ 11,000). Anal. (C$_{14}$H$_{23}$N$_9$O$_3$.0.05CHCl$_3$.3.5H$_2$O) C, H, N.

Example 56

5'-[(2-Cyanoethyl)methylamino]-5'-deoxyadenosine (18b). A solution of 3j[46] (1.0 g, 2.37 mmol) in 10 mL of 3-(methylamino)propionitrile was stirred at room temperature for 5 days. The reaction mixture was poured into diethyl ether (50 mL). The ether layer was decanted and the resulting syrup was purified by column chromatography (silica gel, elution with 7:1:0.1 chloroform:methanol:NH$_4$OH). The desired fractions were combined, concentrated, and dried in vacuo: yield 685 mg (87%), MS: m/z 324 (M+H)$^+$; $^1$HNMR (DMSO-d$_6$) δ 8.34 (s, 1H, H-8), 8.15 (s, 1H, H-2), 7.29 (bs, 2H, 6-NH$_2$), 5.87 (d, 1H, H-1', J$_{1',2'}$=5.4 Hz), 5.46 (bd, 1H, 2'-OH), 5.22 (bd, 1H, 3'-OH), 4.65 (m, 1H, H-2'), 4.13 (m, 1H, H-3'), 3.97-4.03 (m, 1H, H-4'), 2.78 (dd, 1H, 5'-CH$_2$), 2.58-2.68 (bm, 5H, 5'-CH$_2$, NC—CH$_2$CH$_2$), 2.24 (s, 3H, N—CH$_3$).

Example 57

5'-Deoxy-5'-[(2-hydroxyamidinoethyl)methylamino]adenosine (18c). To a solution of 18b (470 mg, 1.4 mmol) in 20 mL of anhydrous MeOH and 4 mL of anhydrous DMF under nitrogen was added hydroxylamine hydrochloride (258 mg, 3.7 mmol) and potassium hydroxide (206 mg, 3.7 mmol) and the resulting suspension was stirred at room temperature for 2 days. The reaction mixture was concentrated to dryness and the crude product was extracted with EtOAc (2×40 mL) and washed with brine solution (20 mL). The organic layer was dried over Na$_2$SO$_4$, filtered, washed with EtOAc and concentrated to dryness. The product was purified by column chromatography. The column was eluted with 4:1:0.5 chloroform:methanol:NH$_4$OH and the desired fractions were combined, concentrated, and dried in vacuo to give a solid: yield 165 mg (32%), MS: m/z 367 (M+H)$^+$; $^1$HNMR (DMSO-d$_6$) δ 8.70 (bs, 1H, NOH), 8.33 (s, 1H, H-8), 8.15 (s, 1H, H-2), 7.27 (bs, 2H, 6-NH$_2$), 5.86 (d, 1H, H-1', J$_{1',2'}$=5.3 Hz), 5.43 (d, 1H, 2'-OH, J$_{2'-2'}$=6.0 Hz), 5.35 (bs, 2H, C—NH$_2$), 5.20 (d, 1H, 3'-OH, J$_{3'-3'OH}$=5.2 Hz), 4.63 (ddd, 1H, H-2', J$_{1',2'}$=5.3 Hz, J$_{2',3'}$=4.9 Hz, J$_{2'-2'OH}$=6.0 Hz), 4.10 (ddd, 1H, H-3', J$_{2',3'}$=4.9 Hz, J$_{3',4'}$=3.5 Hz, J$_{3'-3'OH}$=5.2 Hz), 3.96-4.0 (m, 1H, H-4'), 2.64-2.75 (bm, 2H, 5'-CH$_2$), 2.56 (t, 2H, N(CH$_3$)—CH$_2$), 2.20 (s, 3H, N—CH$_3$), 2.09 (t, 2H, C—CH$_2$). Anal. (C$_{14}$H$_{22}$N$_8$O$_4$.1.2C$_2$H$_5$OH.0.2CH$_3$OH) C, H, N.

Example 58

5'-Deoxy-5'-(N,N-dimethylamino)-8-methyladenosine (19a). A mixture of 3a (150 mg, 0.50 mmol) and a 2M solution of dimethylamine in methanol (10 mL) in a steel bomb was heated for 2 days at 90° C. The reaction mixture was concentrated to dryness and purified by column chromatography (elution with 4:1:0.15 chloroform:methanol:NH$_4$OH). The desired fractions were combined, concentrated and dried in vacuo: yield 38 mg (25%); MS m/z 309 (M+H)$^+$; $^1$HNMR (DMSO-d$_6$) δ 8.08 (s, 1H, H-2), 7.11 (bs, 2H, 6-NH$_2$), 5.74 (d, 1H, H-1', J$_{1',2'}$=5.5 Hz), 5.31 (d, 1H, OH-2', J$_{2'-2'OH}$=5.9 Hz), 5.18 (d, 1H, OH-3', J$_{3'-3'OH}$=5.4 Hz), 5.03 (ddd, 1H, H-2', J$_{1',2'}$=5.5 Hz, J$_{2',3'}$=4.6 Hz, J$_{2'-2'OH}$=5.9 Hz), 4.15 (ddd, 1H, H-3', J$_{2',3'}$=4.6 Hz, J$_{3',4'}$=5.5 Hz, J$_{3'-3'OH}$=5.4 Hz), 3.91-3.96 (m, 1H, H-4'), 2.55-2.61 (m, 1H, 5'-CH$_2$), 2.53 (s, 3H, 8-CH$_3$), 2.42-2.48 (m, 1H, 5'-CH$_2$), 2.14 (bs, 6H, N—(CH$_3$)$_2$); UV λ$_{max}$, nm, pH 1, 258.5 (∈ 15,300), pH 7, 259.3 (∈ 15,300), pH 13, 260.1 (∈ 15,500). Anal. (C$_{13}$H$_{20}$N$_6$O$_3$.0.35CHCl$_3$.0.5C$_2$H$_5$OH) C, H, N.

Example 59

5'-Deoxy-5'-(N,N-dimethylamino)adenosine (19b). Compound 19b was prepared by the same procedure as described for the preparation of 19a using 3g$^{43}$ (500 mg, 1.75 mmol) and a 2M solution of dimethylamine in methanol (20 mL): yield 238 mg (46%); MS m/z 295 (M+H)$^+$; $^1$HNMR (DMSO-d$_6$) δ 8.33 (s, 1H, H-8), 8.15 (s, 1H, H-2), 7.29 (bs, 2H, 6-NH$_2$), 5.86 (d, 1H, H-1', J$_{1',2'}$=5.4 Hz), 5.45 (d, 1H, OH-2', J$_{2'-2'OH}$=5.9 Hz), 5.22 (bd, 1H, OH-3', J$_{3'-3'OH}$=3.9 Hz), 4.65 (ddd, 1H, H-2', J$_{1',2'}$=5.4 Hz, J$_{2',3'}$=5.5 Hz, H$_{2'-2'OH}$=5.9 Hz), 4.10 (ddd, 1H, H-3', J$_{2',3'}$=5.5 Hz, J$_{3',4'}$=4.5 Hz, J$_{3'-3'OH}$=3.9 Hz), 3.94-4.0 (m, 1H, H-4'), 2.62 (dd, 1H, 5'-CH$_2$), 2.48 (dd, 1H, 5'-CH$_2$), 2.18 (bs, 6H, N—(CH$_3$)$_2$); UV λ$_{max}$, nm, pH 1, 256.3 (∈ 15,100), pH 7, 259.2 (∈ 15,500), pH 13, 259.7 (∈ 15,600). Anal. (C$_{12}$H$_{18}$N$_6$O$_3$.0.35CH$_3$OH) C, H, N.

Example 60

5'-Deoxy-5'-methylthio-8-methyladenosine (20a). A solution of 3a (200 mg, 0.66 mmol) and sodium thiomethoxide (47 mg, 0.67 mmol) in 2 mL of anhydrous DMF was stirred for 2 days at room temperature and then concentrated to dryness. The crude product was purified by column chromatography using chloroform:methanol (7:1) as eluent. The desired fractions were collected, concentrated and dried in vacuo: yield 102 mg (49%); MS m/z 312 (M+H)$^+$; $^1$HNMR (DMSO-d$_6$) δ 8.09 (s, 1H, H-2), 7.12 (bs, 2H, 6-NH$_2$), 5.77 (d, 1H, H-1', J$_{1',2'}$=5.7 Hz), 5.38 (bd, 1H, OH-2', J$_{2'-2'OH}$=4.4 Hz), 5.31 (d, 1H, OH-3', J$_{3'-3'OH}$=4.2 Hz), 5.15 (bddd, 1H, H-2', J$_{1',2'}$=5.7 Hz, J$_{2',3'}$=5.7 Hz, J$_{2'-2'OH}$=4.4 Hz), 4.20 (ddd, 1H, H-3', J$_{2',3'}$=5.7 Hz, J$_{3',4'}$=3.6 Hz, J$_{3'-3'OH}$=4.2 Hz), 3.97-4.05 (m, 1H, H-4'), 2.74-2.92 (m, 2H, 5'-CH$_2$), 2.54 (s, 3H, 8-CH$_3$), 2.03 (s, 3H, S—CH$_3$).

Example 61

5'-Deoxy-5'-dimethylsulfonio-8-methyladenosine bromide (21a). Compound 20a (78 mg, 0.25 mmol) in a 2:1 mixture (4 mL) of formic and acetic acid was treated with a 2M solution of bromomethane in diethyl ether (5 mL) and stirred for 6 days in darkness at room temperature. Solvents were removed in vacuo and a solution of the residue in water (10 mL) was extracted with (3×10 mL) ether. The aqueous layer was concentrated to dryness. The resulting product was dissolved in MeOH (10 mL), filtered and treated with diethyl ether to precipitate out the salt. The salt was filtered, washed with ether, and dried in vacuo to give white solid: yield 79 mg (78%); MS m/z 326 (M)$^+$; $^1$HNMR (D$_2$O) δ 8.24 (s, 1H, H-2), 6.03 (d, 1H, H-1', J$_{1',2'}$=5.4 Hz), 5.29 (t, 1H, H-2', J$_{2',3'}$=5.7 Hz), 4.80 (t, 1H, H-3', J$_{3',4'}$=4.8 Hz), 4.52-4.60 (m, 1H, H-4'), 4.11-4.20 (m, 1H, 5'-CH$_2$), 3.81-3.90 (m, 1H, 5'-CH$_2$), 2.92 and 2.89 (2s, 6H, S—(CH$_3$)$_2$), 2.67 (s, 3H, 8-CH$_3$).

Example 62

5'-Deoxy-5'-dimethylsulfonio-8-methyladenosine chloride (21b). Ion exchange resin (IRA-400, Cl$^−$ form) was washed repeatedly with water and loaded into the column. The column was left overnight and washed again repeatedly with water. The bromide salt 21a (50 mg) was dissolved in water (1 mL) and put on the column. The column was eluted with water very slowly in the dark. The desired fractions were combined and lyophilized to yield 30 mg (68%); MS m/z 326 (M)$^+$; $^1$HNMR (D$_2$O) δ 8.24 (s, 1H, H-2), 6.03 (d, 1H, H-1', J$_{1',2'}$=5.4 Hz), 5.29 (t, 1H, H-2', J$_{2',3'}$=5.6 Hz), 4.80 (t, 1H, H-3', J$_{3',4'}$=4.9 Hz), 4.52-4.60 (m, 1H, H-4'), 3.82-4.11 (m, 1H, 5'-CH$_2$), 3.75-3.83 (m, 1H, 5'-CH$_2$), 2.95 and 2.92 (2s, 6H, S—(CH$_3$)$_2$), 2.69 (s, 3H, 8-CH$_3$); UV λ$_{max}$, nm, pH 1, 258.8 (∈ 15,000), pH 7, 259.1 (∈ 14,700), pH 13, 263.5 (∈ 13,000). Anal. (C$_{13}$H$_{20}$ClN$_5$O$_3$S.2H$_2$O) C, H, N.

Example 63

5'-Deoxy-5'-dimethylsulfonioadenosine bromide (21c). The procedure described for 21a was used to prepare 21c from 20b (58 mg, 0.19 mmol): yield 49 mg (65%); MS m/z 312 (M)$^+$.

5'-Deoxy-5'-dimethylsulfonioadenosine chloride (21d). Ion exchange resin (IRA-400, Cl⁻ form) was washed with water and loaded into the column. The column was left overnight and washed again repeatedly with water. The salt 21c (48 mg) was dissolved in water (1 mL) and put on the column. The column was eluted with water very slowly in the dark. The desired fractions were combined together and lyophilized to yield 30 mg (44%); MS m/z 312 (M)⁺; $^1$HNMR (D$_2$O) δ 8.29 (s, 1H, H-8), 8.27 (s, 1H, H-2), 6.12 (d, 1H, H-1', $J_{1',2'}$=4.4 Hz), 4.99 (t, 1H, H-2', $J_{2',3'}$=5.1 Hz), 4.55-4.62 (m, 2H, H-3', H-4'), 3.84-4.0 (m, 2H, 5'-CH$_2$), 2.95 and 2.93 (2s, 6H, S—(CH$_3$)$_2$); UV $\lambda_{max}$, nm, pH 1, 256.4 (∈ 14,300), pH 7, 259.6 (∈ 14,400), pH 13, 266 (∈ 12,300). Anal. (C$_{12}$H$_{18}$ClN$_5$O$_3$S.1.5H$_2$O.0.1C$_2$H$_5$OH) C, H, N, S.

Example 64

5'-[[4-[[(1-ethoxyethylidene)amino]oxy]butyl]methylamino]-5'-deoxy-8-hydroxyadenosine (23a). The procedure described for 6a was used to prepare 23a from 4e (500 mg, 1.68 mm), 13 (481 mg, 2.01 mm), DIEA (109 mg, 0.14 ml, 0.84 mm), and DMF (5 ml). After column chromatography (elution with 4:1:0.2 chloroform:methanol:NH$_4$OH), a yellow glassy sticky solid was obtained: yield 200 mg (26%), MS: m/z 454 (M+H)⁺; $^1$HNMR (DMSO-d$_6$) δ 10.34 (bs, 1H, 8-OH), 8.02 (s, 1H, H-2), 6.49 (bs, 2H, 6-NH$_2$), 5.62 (d, 1H, H-1', $J_{1',2'}$=5.0 Hz), 4.99 (bs, 1H, 3'-OH), 5.19 (bs, 1H, 2'-OH), 4.90 (t, 1H, H-2', $J_{2',3'}$=5.4 Hz), 4.16-4.24 (bm, 1H, H-3'), 3.83-3.89 (m, 1H, H-4'), 3.92 (q, 2H, CH$_3$—CH$_2$), 3.77 (t, 2H, NH$_2$O—CH$_2$), 2.62-3.68 (m, 1H, 5'-CH$_2$), 2.40-2.46 (m, 1H, 5'-CH$_2$), 2.30 (t, 2H, NCH$_3$—CH$_2$), 2.13 (s, 3H, N—CH$_3$), 1.84 (s, 3H, C—CH$_3$), 1.35-1.60 (bm, 4H, NOCH$_2$—CH$_2$CH$_2$), 1.21 (t, 3H, OCH$_2$—CH$_3$).

Example 65

5'-[[4-[[(1-ethoxyethylidene)amino]oxy]butyl]methylamino]-5'-deoxy-8-hydroxyadenosine (23b). Compound 23b was prepared by the same procedure as reported for 6a using 4c (1.00 g, 3.23 mm), 13 (924 mg, 3.87 mm), and DIEA (209 mg, 0.28 ml, 1.6 mm): yield 635 mg (42%), MS: m/z 467 (M+H)⁺; $^1$HNMR (DMSO-d$_6$) δ 7.89 (s, 1H, H-2), 6.87 (q, 1H, 8CH$_3$—NH), 6.46 (bs, 2H, 6-NH$_2$), 5.69 (d, 1H, H-1', $J_{1',2'}$=4.8 Hz), 5.25 (d, 1H, 2'-OH, $J_{2'-2'OH}$=5.6 Hz), 5.06 (d, 1H, 3'-OH, $J_{3'-3'OH}$=5.4 Hz), 4.91 (ddd, 1H, H-2', $J_{1',2'}$=4.8 Hz, $J_{2',3'}$=5.4 Hz, $J_{2'-2'OH}$=5.6 Hz), 4.16 (ddd, 1H, H-3', $J_{2',3'}$=5.4 Hz, $J_{3',4'}$=4.9 Hz, $J_{3'-3'OH}$=5.4 Hz), 3.85-3.94 (m, 1H, H-4'), 3.92 (q, 2H, CH$_3$—CH$_2$), 3.80 (t, 2H, NO—CH$_2$), 2.88 (d, 3H, 8NH—CH$_3$, J=4.6 Hz), 2.65-2.74 (m, 1H, 5'-CH$_2$), 2.46-2.58 (m, 1H, 5'-CH$_2$), 2.34 (t, 2H, NCH$_3$—CH$_2$), 2.17 (s, 3H, N—CH$_3$), 1.83 (s, 3H, C—CH$_3$), 1.37-1.61 (bm, 4H, NOCH$_2$—CH$_2$CH$_2$), 1.19 (t, 3H, OCH$_2$—CH$_3$).

Example 66

5'-[[4-[[(1-ethoxyethylidene)amino]oxy]butyl]methylamino]-5'-deoxy-84 methylamino)adenosine (23c). The same procedure as described for 6a, was used to prepare 23c from 4d (450 mg, 1.26 mm), 13 (360 mg, 1.51 mm), and DIEA (81 mg, 0.10 ml, 0.62 mm). After column chromatography (elution with 7:1 chloroform:methanol), a yellow glassy sticky solid was obtained: yield 312 mg (48%), MS: m/z 514 (M+H)⁺; $^1$HNMR (DMSO-d$_6$) δ 8.17 (s, 1H, H-2), 7.71-7.78 (m, 2H, 8C$_6$H$_5$-OrthoH), 7.58-7.64 (m, 3H, 8C$_6$H$_5$-Meta and ParaH), 7.36 (bs, 2H, 6-NH$_2$), 5.67 (d, 1H, H-1', $J_{1',2'}$=5.7 Hz), 5.32 (bs, 1H, 2'-OH), 5.31 (t, 1H, H-2', $J_{1',2'}$=5.7 Hz, $J_{2,3}$=5.4 Hz), 5.11 (d, 1H, 3'-OH, $J_{3'-3'OH}$=4.8 Hz), 4.16 (bddd, 1H, H-3', $J_{2',3'}$=5.4 Hz, $J_{3',4'}$=4.0 Hz), 3.92-3.97 (m, 1H, H-4'), 3.91 (q, 2H, CH$_3$—CH$_2$), 3.79 (t, 2H, NO—CH$_2$), 2.72-2.80 (m, 1H, 5'-CH$_2$), 2.54-2.59 (m, 1H, 5'-CH$_2$), 2.34 (bt, 2H, NCH$_3$—CH$_2$), 2.17 (bs, 3H, N—CH$_3$), 1.83 (s, 3H, C—CH$_3$), 1.39-1.60 (bm, 4H, NOCH$_2$—CH$_2$CH$_2$), 1.18 (t, 3H, OCH$_2$—CH$_3$).

Example 67

5'-[(carboethoxyethyl)methylamino]-5'-Deoxy-8-methyladenosine (33a). The general procedure previously described for 6a was used to prepare 33a using 4a (500 mg, 1.69 mm), ethyl 3-chloropropionate (270 mg, 1.97 mm), DIEA (109 mg, 0.14 ml, 0.84 mm), and DMF (5 ml). The reaction mixture was heated at 60° C. for 2 days. Starting material remained but since the solution was getting darker, heating was stopped. The product was purified by column chromatography (6:1:0.1 chloroform:methanol:NH$_4$OH) to give sticky solid: yield 210 mg (31%); MS m/z 395 (M+H)⁺; $^1$HNMR (DMSO-d$_6$) δ 8.08 (s, 1H, H-2), 7.11 (bs, 2H, 6-NH$_2$), 5.74 (d, 1H, H-1', $J_{1',2'}$=5.6 Hz), 5.33 (bd, 1H, OH-2'), 5.16 (bd, 1H, OH-3'), 5.12 (bddd, 1H, H-2', $J_{1',2'}$=5.6 Hz, $J_{2',3'}$=5.5 Hz), 4.21 (bddd, 1H, H-3', $J_{2',3'}$=5.5 Hz, $J_{3',4'}$=4.3 Hz), 4.01 (q, 2H, CH$_3$—CH$_2$), 3.91-4.00 (m, 1H, H-4'), 2.70-2.77 (m, 1H, 5'-CH$_2$), 2.54-2.66 (m, 3H, 5'-CH$_2$, CO—CH$_2$), 2.53 (s, 3H, 8-CH$_3$), 2.38 (t, 2H, NCH$_3$—CH$_2$), 2.16 (bs, 3H, N—CH$_3$), 1.15 (t, 3H, OCH$_2$—CH$_3$).

Example 68

5'-[(carboethoxyethyl)methylamino]-5'-Deoxy-8-ethyladenosine (33b). Compound 33b was prepared by the same procedure as described for the preparation of 6a and 33a using 4b (260 mg, 0.84 mm), ethyl 3-chloropropionate (138 mg, 1.0 mm), DIEA (53 mg, 0.07 ml, 0.41 mm), and DMF (4 ml). After column chromatography (elution with 7:1:0.1 chloroform:methanol:NH$_4$OH), a glassy sticky solid was obtained: yield 153 mg (44%), MS: m/z 409 (M+H)⁺; $^1$HNMR (DMSO-d$_6$) δ 8.08 (s, 1H, H-2), 7.10 (bs, 2H, 6-NH$_2$), 5.71 (d, 1H, H-1', $J_{1',2'}$=5.5 Hz), 5.32 (bd, 1H, OH-2', $J_{2'-2'OH}$=5.0 Hz), 5.16 (bd, 1H, OH-3', $J_{3'-3'OH}$=5.1 Hz), 5.12 (ddd, 1H, H-2', $J_{1',2'}$=5.5 Hz, $J_{2',3'}$=5.7 Hz, $J_{2'-2'OH}$=5.0 Hz), 4.14 (ddd, 1H, H-3', $J_{2',3'}$=5.7 Hz, $J_{3',4'}$=4.1 Hz, $J_{3'-3'OH}$=5.1 Hz), 4.01 (q, 2H, CH$_3$—CH$_2$), 3.91-3.98 (m, 1H, H-4'), 2.87 (q, 2H, CH$_2$ of 8-Et), 2.71-2.79 (m, 1H, 5'-CH$_2$), 2.51-2.65 (m, 3H, 5'-CH$_2$, CO—CH$_2$), 2.38 (t, 2H, NCH$_3$—CH$_2$), 2.16 (bs, 3H, N—CH$_3$), 1.30 (t, 31-1, CH$_3$ of 8-Et), 1.15 (t, 3H, OCH$_2$—CH$_3$).

Example 69

5'-[(carboxamidoethyl)methylamino]-5'-Deoxy-8-methyladenosine sulfate (1.5:1 salt) (34a). Compound 33a (89 mg, 0.22 mm) was dissolved in 5 ml of methanolic ammonia and the solution was stirred for 5 days at room temperature. The reaction mixture was concentrated to dryness and purified by column chromatography (4:1:0.2 chloroform:methanol:NH$_4$OH). The desired fractions were collected, concentrated, and dried in vacuo. The product was dissolved in 8 ml of EtOH and 2N H$_2$SO$_4$ was added drop wise. The compound was precipitated out, which was filtered, and washed with EtOH. This product, which was hygroscopic in nature, was dissolved in water (2 ml) and lyophilized to give a white solid: yield 65 mg (55%), MS: m/z 366 (M+H)⁺; $^1$HNMR (D$_2$O) δ 8.43 (s, 1H, H-2), 6.09 (d, 1H, H-1', $J_{1',2'}$=5.9 Hz), 5.0-5.30 (bm, 1H, H-2'), 4.61-4.70 (bm, 1H, H-4'), 4.51-4.54 (bm, 1H, H-3'), 3.30-3.89 (bm, 5H, N—CH$_3$CH$_2$), 2.96 (bs, 2H, 5'-CH$_2$), 2.77 (bs, 2H, NH$_2$CO—CH$_2$), 2.70 (s, 3H, 8-CH$_3$); UV λ$_{max}$, nm, pH 1, 258.4 (∈ 14,900), pH 7, 260.1 (∈ 14,900), pH 13, 260.1 (∈ 15,300).

Example 70

5'-[(carboxamidoethyl)methyamino]-5'-Deoxy-8-ethyladenosine sulfate (1.1:1 salt) (34b). The procedure was the same as disclosed above for 34a using 33b (149 mg, 0.36 mm) and methanolic ammonia (5 ml): yield 94 mg (51%), MS: m/z 380 (M+H)$^+$; $^1$HNMR (DMSO-d$_6$) δ 8.08 (s, 1H, H-2), 7.31 (bs, 1H, CO—NH$_2$), 7.10 (bs, 2H, 6-NH$_2$), 6.71 (bs, 1H, CO—NH$_2$), 5.72 (d, 1H, H-1', J$_{1',2'}$=5.4 Hz), 5.31 (d, 1H, OH-2', J$_{2'-2'OH}$=6.2 Hz), 5.16 (d, 1H, OH-3', J$_{3'-3'OH}$=5.5 Hz), 5.09 (ddd, 1H, H-2', J$_{1',2'}$=5.4 Hz, J$_{2',3'}$=5.7 Hz, J$_{2'-2'OH}$=6.2 Hz), 4.17 (ddd, 1H, H-3', J$_{2',3'}$=5.7 Hz, J$_{3',4'}$=4.3 Hz, J$_{3'-3'OH}$=5.5 Hz), 3.92-3.99 (m, 1H, H-4'), 2.87 (q, 2H, CH$_3$—CH$_2$), 2.69-2.75 (m, 1H, 5'-CH$_2$), 2.52-2.60 (m, 3H, CO—CH$_2$, 5'-CH$_2$), 2.18 (bs, 2H, NCH$_3$—CH$_2$), 2.16 (s, 3H, N—CH$_3$), 1.30 (t, 3H, CH$_3$ of 8-Et); $^1$HNMR (D$_2$O) δ 8.38 (s, 1H, H-2), 6.09 (d, 1H, H-1', J$_{1',2'}$=6.2 Hz), 5.33 (bs, 1H, H-2'), 4.56-4.62 (m, 1H, H-4'), 4.51-4.54 (m, 1H, H-3'), 3.87-3.96 (bm, 2H, NH$_2$CO—CH$_2$), 3.56 (s, 3H, N—CH$_3$), 2.98-3.80 (bm, 2H, CH$_3$—CH$_2$), 2.96 (bs, 2H, 5'-CH$_2$), 2.72-2.82 (m, 2H, NCH$_3$—CH$_2$), 1.39 (s, 3H, CH$_3$ of 8-Et); UV λ$_{max}$, nm, pH 1, 259.4 (∈ 15,200), pH 7, 260.8 (∈ 15,100), pH 13, 260.6 (∈ 15,500).

Example 71

5'-[(carboethoxymethyl)methyamino]-5'-Deoxy-8-methyladenosine (35). Compound 35 was prepared by the same procedure as described for the preparation of 6a using 4a (415 mg, 1.41 mm), ethyl chloroacetate (207 mg, 0.18 ml, 1.68 mm), DIEA (91 mg, 0.12 ml, 0.70 mm), and DMF (5 ml): yield 204 mg (38%), MS: m/z 381 (M+H)$^+$; $^1$HNMR (DMSO-d$_6$) δ 8.06 (s, 1H, H-2), 7.11 (bs, 2H, 6-NH$_2$), 5.73 (d, 1H, H-1', J$_{1',2'}$=5.4 Hz), 5.33 (bd, 1H, OH-2', J$_{2'-2'OH}$=4.7 Hz), 5.19 (bd, 1H, OH-3', J$_{3'-3'OH}$=4.9 Hz), 5.03 (ddd, 1H, H-2', J$_{1',2'}$=5.4 Hz, J$_{2',3'}$=5.7 Hz, J$_{2'-2'OH}$=4.7 Hz), 4.17 (ddd, 1H, H-3', J$_{2',3'}$=5.7 Hz, J$_{3',4'}$=4.4 Hz, J$_{3'-3'OH}$=4.9 Hz), 4.02 (q, 2H, CH$_3$—CH$_2$), 3.92-3.99 (m, 1H, H-4'), 3.27 (bs, 2H, NCH$_3$—CH$_2$), 2.83-2.90 (m, 1H, 5'-CH$_2$), 2.70-2.79 (m, 1H, 5'-CH$_2$), 2.53 (s, 3H, 8-CH$_3$), 2.31 (s, 3H, N—CH$_3$), 1.13 (t, 3H, OCH$_2$—CH$_3$); UV λ$_{max}$, nm, pH 1, 258.9 (∈ 16,100), pH 7, 260 (∈ 15,900), pH 13, 260.1 (∈ 16,200).

Example 72

5'-[(carboxamidomethyl)methyamino]-5'-Deoxy-8-methyladenosine sulfate (1.45:1 salt) (36). The same procedure used to prepare 34a was used to prepare 36 using 35 (200 mg, 0.52 mm) and methanolic ammonia (5 ml): yield 105 mg (39%), MS: m/z 352 (M+H)$^+$; $^1$HNMR (DMSO-d$_6$) δ 8.08 (s, 1H, H-2), 7.11 (bs, 2H, CO—NH$_2$), 7.07 (bs, 2H, 6-NH$_2$), 5.74 (d, 1H, H-1', J$_{1',2'}$=5.2 Hz), 5.34 (d, 1H, OH-2', J$_{2'-2'OH}$=5.9 Hz), 5.21 (d, 1H, OH-3', J$_{3'-3'OH}$=5.7 Hz), 4.97 (ddd, 1H, H-2', J$_{1',2'}$=5.2 Hz, J$_{2',3'}$=5.5 Hz, J$_{2'-2'OH}$=5.9 Hz), 4.21 (ddd, 1H, H-3', J$_{2',3'}$=5.5 Hz, J$_{3',4'}$=5.2 Hz, J$_{3'-3'OH}$=5.7 Hz), 3.94-4.01 (m, 1H, H-4'), 2.94 (d, 1H, NCH$_3$—CH$_2$, J=15.7 Hz), 2.88 (d, 1H, NCH$_3$—CH$_2$, J=15.7 Hz), 2.75-2.80 (m, 1H, 5'-CH$_2$), 2.63-2.70 (m, 1H, 5'-CH$_2$), 2.53 (s, 3H, 8-CH$_3$), 2.23 (s, 3H, N—CH$_3$), $^1$HNMR (D$_2$O) δ 8.40 (s, 1H, H-2), 6.08 (d, 1H, H-1', J$_{1',2'}$=4.8 Hz), 5.01 (t, 1H, H-2', J$_{2',3'}$=5.2 Hz), 4.60 (t, 1H, H-3', J$_{3',4'}$=4.9 Hz), 4.50-4.59 (m, 1H, H-4'), 4.03-4.17 (m, 2H, NH$_2$CO—CH$_2$), 3.82-3.92 (m, 1H, 5'-CH$_2$), 3.68-3.76 (m, 1H, 5'-CH$_2$), 3.03 (s, 3H, N—CH$_3$), 2.70 (s, 3H, 8-CH$_3$); UV λ$_{max}$, nm, pH 1, 259 (∈ 15,900), pH 7, 259.7 (∈ 16,100), pH 13, 260.2 (∈ 16,100).

Mutagenesis and Plasmid Construction

Plasmids in the pQE30 vector for the production of recombinant wild type and F223A mutant hAdoMetDC in *E. coli* that was used for crystallography were produced as described previously (23). This construct replaces the N-terminal methionine with MRGS(H)$_6$GS— or purification by immobilized metal affinity chromatography. A different plasmid also based on the pQE30 vector was used for the production of protein for the hAdoMetDC enzyme assays. In this plasmid, the (H)$_6$ tag was located at the carboxyl end replacing the terminal -QQQQQS. The position of the (H)$_6$ tag did not alter the activity of the purified enzyme.

Protein Expression and Purification

The wild type hAdoMetDC was purified based on the protocol described by Ekstrom et al. (20). The plasmid encoding the enzyme is in the pQE30 vector and was transformed into JM109 strain *E. coli* cells. The cells were grown as an overnight culture in LB media at 37° C. and then introduced into larger cell cultures with both of the cultures containing 100 mg/mL ampicillin. The cells were grown until they reached an O.D$_{600}$ of 0.6 and then were induced with 100 mg/L isopropyl-1-thio-β-D galactopyranoside (IPTG). The cells were allowed to grow overnight at 15° C. and were then harvested by centrifugation, washed using a wash buffer which contained 20 mM Na$_2$HPO$_4$, pH 7.0, 500 mM NaCl, 2.5 mM putrescine, 0.02% Brij-35 and 10 mM imidazole, and stored at −80° C. The frozen cell pellet was thawed, suspended in the wash buffer, and lysed using a French press at 1500 psi. The cellular debris and the lysate were separated by centrifugation at 12000 g. Talon metal affinity resin was equilibrated with the wash buffer and then the lysate and the resin were gently spun together for 1.5 hours. The resin was loaded onto a column and washed with a volume of wash buffer equivalent to 15-20 times the column volume. Next, the column was washed in the same manner with wash buffer containing 25 mM imidazole. The protein was then eluted with buffer containing 100-200 mM imidazole. The eluted protein was concentrated to around 10 ml and passed through a Sephadex G-75 column pre-equilibrated with 10 mM Hepes, pH 7.5, 2.5 mM putrescine, 5 mM DTT, 0.1 mM EDTA, 0.02% Brij-35, and 300 mM NaCl. The buffer was run through the column and the fractions containing the protein were identified by UV at 280 nm. The protein was concentrated to ~10 mg/mL and stored at −80° C. The purification of the F223A mutant was similar to that of the native enzyme.

Crystallization

The protein was thawed on ice and buffer exchanged to 10 mM Hepes, pH 7.5, 200 mM NaCl and 1 mM DTT using Bio-rad buffer exchange chromatography columns (Bio-rad Laboratories, Hercules, Calif. 94547). The native protein was incubated with a 4-6 molar excess of MAOBEA and MAOEMA for 24 hours prior to crystallization. The F223A mutant was diluted to ~6 mg/mL and incubated with a 4-6 molar excess of MeAdoMet for 24 hours prior to crystallization. Crystals of both the native and the mutant complexes were grown using the hanging drop method at 22° C. in 13-16% PEG 8000, 100 mM Tris, pH 8.0-9.0, and 10 mM DTT. Crystals appeared overnight and were stable for 1-2 weeks.

Data Collection and Processing

The data for the MAOEMA complex was collected at home source on a Rigaku R-axis IV+ detector with a Cu Kα radiation from a Rigaku RU-300 rotating anode generator. The data for the MAOBEA complex was collected at the 8BM station of NE-CAT beam line at the Advanced Photon Source (APS) using a ADSC quantum 315 detector. The data for the AdoMetDC F223A mutant with MeAdoMet was collected at the F2 station of CHESS using an ADSC Quantum 4 detector. All the crystals were flash frozen under liquid nitrogen or liquid nitrogen stream. The diffraction quality of the crystals strongly depended on the cryoprotection of the crystals. The crystals were sequentially transferred to a solution containing the well solution with 2%, 5%, 8%, 15% and 18% glycerol with 1-2 min equilibration between each step.

The data for all of the complexes was indexed, integrated and scaled using the HKL2000 (24) program suite. The data collection statistics are summarized in Table 1.

Structure Determination and Refinement

The structures of all of the complexes were determined by molecular replacement using the structure of native AdoMetDC with MeAdoMet bound (PDB 1I7B) as the search model, and the CNS program suite (25). The model building for the MAOEMA and MAOBEA complex was done using the program O (26). The model building for the AdoMetDC F223A mutant complexed with MeAdoMet was done by using program coot (27). The conformations of the ligand molecules were determined by the difference fo-fc and the composite omit maps. The parameters and the topology files for the ligands were generated using the hic-up server (28). The difference maps also showed density for a molecule of putrescine bound in all the three structures. The refinement statistics of the complexes are given in Table 2.

Molecular Modeling of MeAdoMet in the Active Site of AdoMetDC

Determination of the conformational preference of ligands in the active site of AdoMetDC was carried out by the program Macromodel version 7.2 (29). The base shell of atoms included any residue within 20.0 Å of the active site (from pdb 1I7B) and was used as the starting model for conformational search and energy minimization. The ligand was added to the active site followed by removal of water molecules and an appropriate hydrogen treatment. The covalent bond between the amino terminal of the ligand and the pyruvoyl group was made.

The resulting structure was subjected to 50,000 mixed Monte Carlo MCMM/lowmode conformational search steps (30) (31) allowing residues in the 5 Å shell around the active site to move. However, the residues H5, E67, C226 and E247 were fixed. The generated structures were energy minimized to a gradient of 0.05 kJ/mol using the AMBER* force field (32, 33), distance dependent dielectric with a dielectric constant of 4, and a TNCG minimization technique (34). The global minimum of this search (after convergence) was taken and fine tuned at a gradient of 0.01 kJ/mol with just the ligand allowed to move. The jobs were run with the base starting in each syn and anti conformations for completeness. The AMBER* parameters for the sulphonium ion were adapted from the work done by Dr. Markham et al. (35).

Modeling of MAOBEA in the Active Site of AdoMetDC

The modeling of the terminal three atoms of MAOBEA was done by using conformational searching and molecular mechanics using the program Macromodel version 7.2. Since the position of the rest of the ligand and the protein was determined to high accuracy by the electron density, all of the protein and the ligand except the last three atoms were fixed during the conformational search. Torsional rotation was allowed around C5-C4 and C4-O1 bonds during the conformational search. The structures generated by the Monte Carlo search were minimized to a gradient of 0.01 kJ/mol using the AMBER* force field, distance dependent dielectric with a dielectric constant of 4, and a TNCG minimization technique. A quick look at the top 5 minimum structures showed that they were similar and the global minimum of the search was considered to obtain the coordinates of the disordered terminal atoms of MAOBEA.

Assay of AdoMetDC Activity and Determination of Inhibitor $IC_{50}$ Values

AdoMetDC was assayed by measuring the release of $^{14}CO_2$ from S-adenosyl-L-[carboxy-$^{14}$C]methionine (Amersham Pharmacia Biotech, ~60 mCi/mmol) (36). Assay of 30 ng of C-terminal his-tagged AdoMetDC under these conditions results in ~7000 cpm with a background of 30, and an activity of ~1.5 pmol/min/ng protein. For determination of the abilities of compounds to inhibit AdoMetDC, the enzyme activity was determined in the presence of no inhibitor and at least 5 concentrations of each potential inhibitor. The $IC_{50}$ values were determined from curve fitting to plots of the inhibitor concentration versus the % inhibition of AdoMetDC.

Results

Modeling of MeAdoMet in the Active Site of AdoMetDC

Figure 1B:
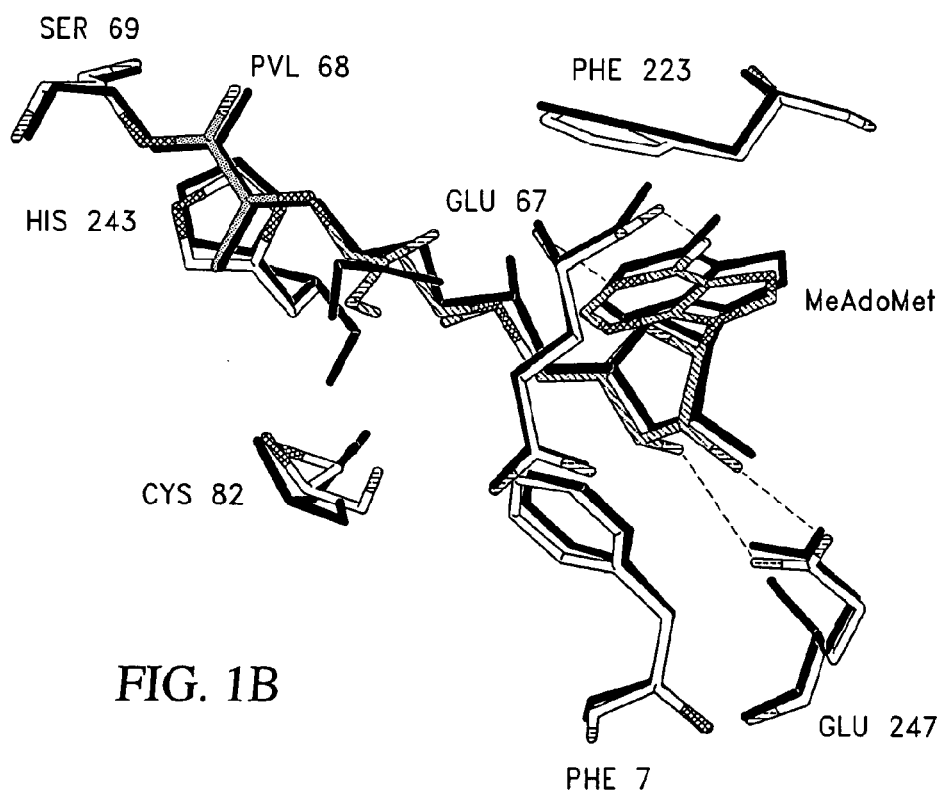
FIG. 1B illustrates the structure derived from modeling of MeAdoMet in the active site of AdoMetDC (shown as the darker shape) is superimposed on the actual crystal structure (shown as the lighter shade).

The crystal structures of AdoMetDC complexed with MeAdoMet or the inhibitors MHZPA and MAOEA have shown that the ligand binds with the adenine base in the unusual syn conformation.[23] The active site residues of AdoMetDC with MeAdoMet bound are shown in FIG. 1A. However, NMR data coupled with molecular modeling studies suggest that, in solution, AdoMet assumes an anti conformation as an energy minimum.[35] A survey of crystal structures in which AdoMet is bound has shown the substrate to assume a position with a range of glycosidic torsion angles, and has revealed that the anti conformation is preferred in most structures but the syn conformation is observed in some.[35] In order to explain the conformational preferences and the related energetics of ligand binding to AdoMetDC, the modeling of MeAdoMet in the active site of AdoMetDC was done. Since MeAdoMet is tethered to the active site of AdoMetDC through covalent bonding to the pyruvoyl group, docking involving positional and orientational sampling was not performed. Instead, a conformational search to locate the populated low energy conformations of AdoMet in the AdoMetDC active site was performed using the mixed Monte Carlo/Low Mode conformational search method within the MacroModel program.[29-31] The conformational search started with AdoMet in either the anti or syn conformation and in each case the five lowest energy structures from the search exhibit a syn conformation for the adenine nucleoside. A superposition of the modeled structure with the crystal structure (FIG. 1B) indicates that the results of the conformational search match well with those observed crystallographically. Conformational searches were also done for AdoMet, 5'-deoxy-5'-(dimethylsulfonio)adenosine (MMTA), MHZPA, and MAOEA binding to AdoMetDC, and each yielded a syn conformation of the base (data not shown). The ribose makes key hydrogen bonds to E247 and the adenine base stacks between F7 and F223 and also makes hydrogen bonds to the backbone amide and C-terminal carboxyl group of E67. The main interactions constraining the base to the syn conformation are the pi-pi stacking of the base with F223 and with F7 and two hydrogen bonds between the base and the backbone of E67.

Virtual Mutations in the Active Site of AdoMetDC

Figure 2A:
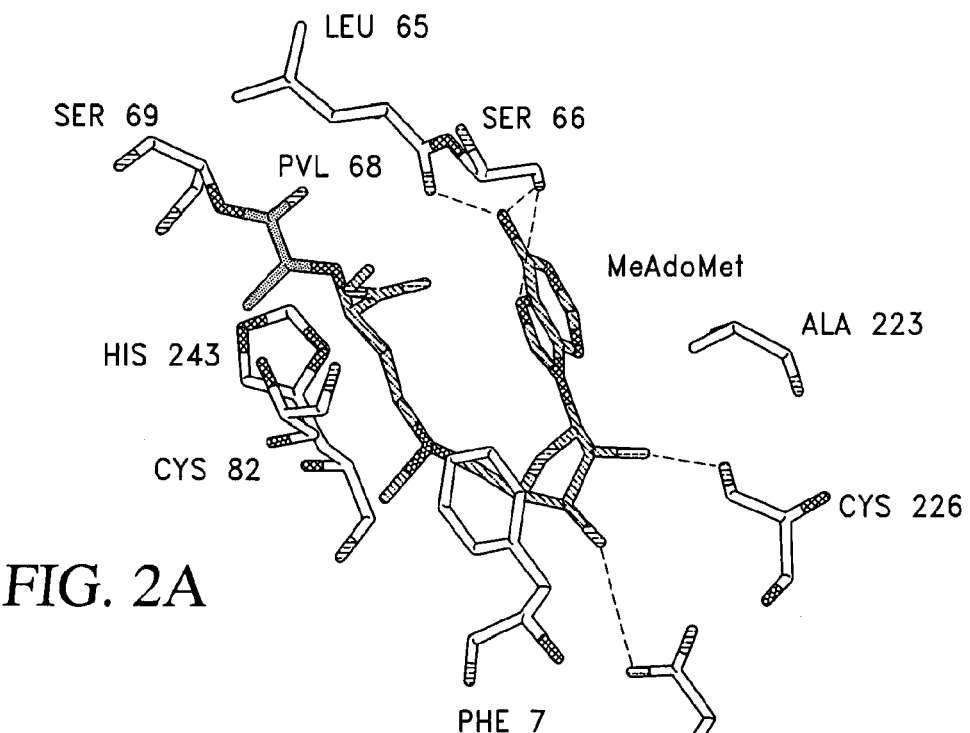
FIGS. 2 A and B illustrate the modeling of hAdoMetDC F223A and hAdoMetDC F7A, respectively complexed with MeAdoMet.
Figure 2B:
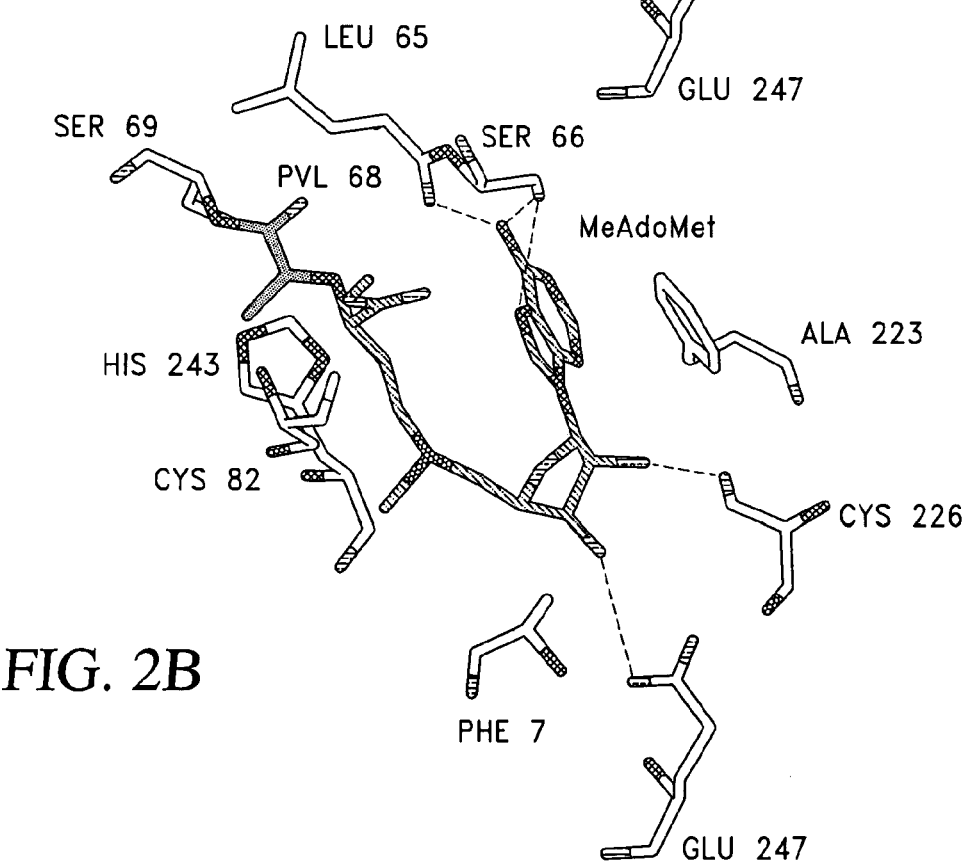

Virtual mutations were made to study the effect of various residues on the conformation of the bound nucleoside. Conformational searching with MacroModel employing the AdoMetDC F223A and F7A single amino acid mutants, with MeAdoMet in the active site, resulted in a mixture of syn and anti conformations in the low energy ensemble. With each of the mutations, the global minimum was an anti conformation of the adenine base closely followed by a syn conformation with an energy difference of ~0.5 kcal/mol. The global minimum energy conformation of the ligand bound in the anti conformation in the F223A mutant exhibits major changes compared to the $2^{nd}$ lowest energy conformer which adopts the syn conformation. In the F223A binding site, the ribose of the global minimum energy structure is displaced and makes hydrogen bonds to E247 and C226 instead of to E247 alone (FIG. 2A). This change makes the ligand curve upon itself, the sulfonium stacks over the adenine base, and the adenine base makes three hydrogen bonds to S66. In the F7A binding site, the ligand assumes a similar conformation as with the F223A mutant. The F223 residue undergoes a torsional change to accommodate the conformational change of the ligand and also stacks with the adenine base (FIG. 2B). The presence of the anti conformation in low energy structures of the ligand in the enzyme active site where virtual mutations have been made suggests the importance of the phenyl groups in maintaining the syn conformation of the ligand within the wild-type enzyme binding site. The crystal structure of the F223A mutant complexed with MeAdoMet was also obtained.

Tertiary Structure of AdoMetDC and the F223A Mutant

The dimer of human AdoMetDC (hAdoMetDC) is a four layer αββα sandwich. The proenzyme consists of 334 amino acid residues and the enzyme undergoes autoprocessing to give the α and the β subunits.[20] The autoprocessing yields the active enzyme with the pyruvoyl cofactor The pyruvoyl group is located at the end of the N terminal β sheet and the active site involves residues from both of the β sheets. The binding site of putrescine, which activates both the autoprocessing and decarboxylation reactions of hAdoMetDC, is located well away from the ligand binding site within the wild-type enzyme. Experimental conditions for the purification of the enzyme included putrescine at sufficient concentration to ensure high occupancy of the putresine binding site. The loops between the residues 1-4, 21-27, 165-173, 288-299, 329-334 are disordered in the crystal structures. The structure of the AdoMetDC F223A mutant is similar to that of the wild type protein.

Crystal Structure of the AdoMetDC F223A Mutant Complexed with MeAdoMet

Figure 3:
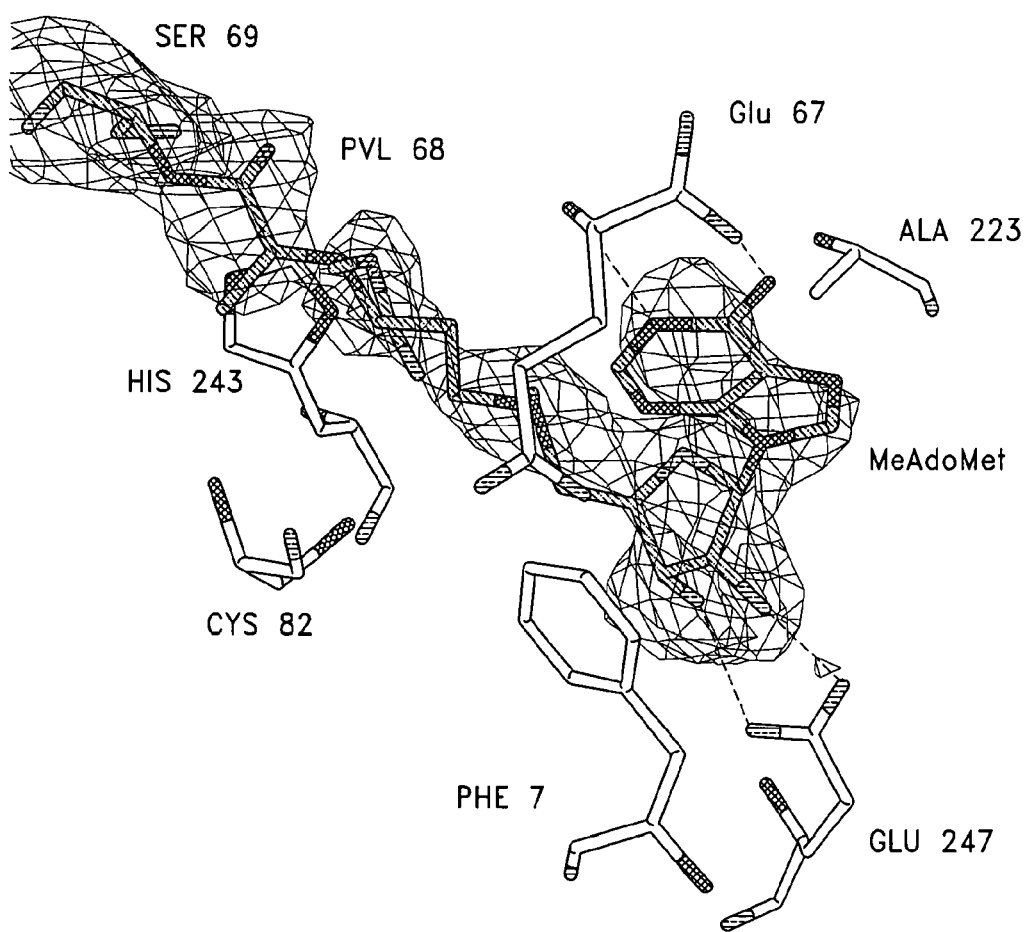
FIG. 3 illustrates the crystal structure of MeAdoMet in the active site of the AdoMetDC F223A mutant.

The crystal structure of hAdoMetDC F223A complexed with MeAdoMet was solved using molecular replacement. The difference fo-fc density shows that MeAdoMet is covalently bound to the enzyme and the adenine base adopts a clear syn conformation (FIG. 3). The composite omit map density, as expected, shows no density for F223. The ribose makes two hydrogen bonds to E247 which anchor the ligand and the base is held in syn conformation by stacking interactions with F7 and hydrogen bonds to E67. A molecule of putrescine per monomer is present in the putrescine binding site in the mutant protein. A superposition of MeAdoMet in the F223A structure and the native structure shows that there is no appreciable change in the position or conformation of the ligand. The loops disordered in the wild type protein are also disordered in the mutant.

Synthesis and Biochemical Analysis of Potential Inhibitors of hAdoMetDC

Several series of AdoMet structural analogues were synthesized with substituents ranging from a methyl group to a phenyl group at the 8 position of adenine. Each of these compounds was then assayed for their ability to inhibit hAdoMetDC and $IC_{50}$ values for the inhibition were determined (Table 3).

The inhibitors tested fall into four groups, as noted in the Chemical Synthesis section. One group (7a-c, 9a-f, 12) has an aminooxyalkyl side chain at C-5', which can form a Schiff base with the pyruvate of AdoMetDC.[18,41,42] Compounds of this group were potent inactivators with a 4-aminooxybutyl group being slightly superior to a 2-aminooxyethyl addition. A second group of compounds (13d, e, f, j, k, l, m) had an amide or a hydrazide side chain at C-5' and a third group of inhibitors (14a, b, d, e, f; 15a, b, c, d; 17c, d) had an aminoalkylamino side chain at C-5'. Also related to the third group by the synthetic method are 18a and 18c, which, respectively, have a guanidine and an amidoxime at the end of the C-5' side chain. The compounds of groups 2 and 3 were less potent (particularly those with the aminoalkylamino, guanidine, or amidoxime side chain) but are more likely to be stable under in vivo conditions. The final group of compounds consisted of 5'-dimethylamino (19a, b) or 5'-dimethylsulfonio (21b, d) compounds. Compound 21d has previously reported to be an AdoMetDC inhibitor with a $K_i$ in the μM range.[43] As shown in Table 3, the replacement of sulfur by nitrogen slightly improves the AdoMetDC inactivation.

Within each of these groups, there was a consistent improvement of inhibitory activity when an 8-methyl substituent was added to the adenine ring. The reduction in the $IC_{50}$ value varied from 3.4-fold for compound 9d to 15-17-fold for compounds 19a and 13d. There was an 8-fold increase in potency when an adenine 8-methyl substituent was added to compound 12 (MAOEA) forming compound 7a. This is consistent with the concept that the 8-methyl substitution on adenine biases the corresponding nucleoside toward the syn conformation and that this is the form that is bound at the active site. An adenine 8-hydroxy substituent resulted in slightly increased potency over no substituent, but was not as effective as the 8-methyl substituent (compare 9c to 9e and 9e). Larger 8-substitutions did not improve the effectiveness. An 8-phenyl addition to compounds 12, 9f and 14d abolished the inhibitory activity. Smaller additions such as 8-ethyl (compare 9d and 9e, 13d and 13e, and 17c and 17d) or 8-methylamino (compare 7a and 7b and 17c and 14a) were tolerated but were worse than 8-methyl.

Crystal Structure of 7a

The crystal structure of native hAdoMetDC with 7a was solved using molecular replacement. As noted above, 7a is structurally similar to the previously studied inhibitor MAOEA except that it has a methyl substitution at the 8-position on the adenine base. The electron density indicates that the amino terminal of 7a makes a Schiff base with the pyruvoyl group of the enzyme. The adenine base of 7a adopts a syn conformation in the crystal structure as expected. The electron density for the complex of 7a is shown in FIGS. 4A(5A). There is one molecule of putrescine bound in the putrescine binding site.

Crystal Structure of 9e

The crystal structure of native hAdoMetDC with 9e was solved using molecular replacement. 9e is similar to MAOEA except for an ethyl substituent on the 8-position of the adenine base and two extra carbon atoms between the tertiary nitrogen (near ribose) and the terminal nitrogen. The presence of a long linker between the ribose and the amino terminus makes this ligand interesting to study. The electron density maps show no density for Schiff base formation between the pyruvoyl group and the amino terminus of the ligand. There is no density for the terminal three atoms of the ligand and there is good density for the rest of the ligand (FIG. 4B.). The position of the last three atoms was obtained by modeling them to an energetically favorable conformation using molecular modeling. The density around the pyruvoyl group fits it well and does not show any evidence of formation of a Schiff base. The ribose makes the critical hydrogen bonds to E247 and anchors the ligand. The base is held in the syn conformation and is stabilized by pi-pi stacking. The density of the ethyl substituent on the base is well defined and indicates that the terminal ethyl group is not disordered.

Discussion

The active site of AdoMetDC is defined by the pyruvoyl group. The interactions of various ligands at the active site were elucidated from the crystal structures obtained from complexes of the enzyme with the inhibitors MHZPA, MAOEA, MeAdoMet, MGBG and CGP48664A, which were reported previously.[23] The crystal structure of MeAdoMet covalently bound to the enzyme most closely approximates the substrate AdoMet in the active site. The crystal structure shows key interactions of MeAdoMet with the enzyme including: 1. hydrogen bonding of the ribose oxygens with E247; 2. stacking interaction of the adenine ring with F223 and F7; 3. hydrogen bonding of the 6-amino substituent of the adenine ring with the terminal carboxyl group of E67; and 4. hydrogen bonding of N' of the adenine ring with the amide N—H of E67 (FIG. 1A). Similar interactions are also present in the structures of MHZPA and MAOEA complexed with hAdoMetDC. The glycosidic angle for the adenine base in these three structures ranges from 128° to 139° which indicates a strong preference for the syn conformation of the adenosine derived nucleoside. The syn conformation is stabilized by the pi-pi stacking of the adenine base with F223 and F7 as well as hydrogen bonding to the protein backbone. Crystal structures of MGBG and CGP48664A with the enzyme show that they stack in between the two phenyl rings and make hydrogen bonds to E247 and other residues of the protein.

The molecular modeling of MeAdoMet in the active site of hAdoMetDC was performed by using mixed Monte Carlo/Low Mode conformational searching as previously described. The glycosidic torsional angle was free to rotate during the conformational search which would allow the a wide range of rotomers that are compatible with the steric constraints of the active site before energy minimization. The low energy structures show that the adenine derived nucleosides prefer to attain a syn conformation in the active site of hAdoMetDC. The conformational preference of AdoMet in solution and in vacuo has been studied by Markham et al.[35] The studies based on $^1$H NMR and calculations based on NMR constraints have shown that AdoMet prefers an anti conformation in solution and a syn conformation in a vacuum. In solution, the energy difference between the anti and the corresponding syn conformation, which includes steric, electrostatic and the solvation contributions, is around −34 kJ/mol. Our crystal structures and modeling results show that the enzyme prefers to bind ligands in the energetically unfavorable syn conformation and that maintenance of this conformation is aided by pi-pi interactions with residues of the protein containing aromatic rings. Typical pi-pi interactions of parallel geometry account for a stabilization of 2-3 kcal/mol.[44] There are many stabilizing factors which aid the ligand in overcoming the glycosidic torsional barrier during binding to the enzyme. An additional factor that may contribute to stabilization of the syn conformation of the nucleoside involves interaction of the sulfonium ion with the adenine base. Ab initio calculations at the Hartree Fock 6-31G** level were done on AdoMet with F223 and F7 positioned near AdoMet (based on crystal structure pdb id 1I7B) to obtain single point energy and corresponding charges on atoms. These calculations have shown that the $N^3$ of the adenine base has a charge of −0.79 and is present at a distance of 3.4 Å from the sulfonium ion which carries a charge of +0.39 on it (data not shown). Thus, there is a favorable electrostatic interaction between these two atoms that stabilizes the syn conformation The roles of F223 and F7 in AdoMetDC were previously studied through crystal structures and kinetic experiments.[23] The crystal structures of AdoMetDC with inhibitors like MGBG and CGP48664A have shown that the phenyl rings give rise to stacked structures that encompass the entire length of MGBG and the bicyclic ring of CGP48664A. Kinetic data from reaction of hAdoMetDC F223A and F7A mutants with the substrate AdoMet have shown that there is a 45 fold reduction of the specificity constant ($k_{cat}/k_m$) for the F7A mutant and a 1400 fold decrease with the F223A mutant. The kinetic data on inhibition by inhibitors like MGBG and CGP48664A have shown a significant increase in the $IC_{50}$ values for both mutants when compared to the wild-type enzyme. The decrease in activity was greater for the F223A mutant than the F7A mutant. These findings are also supported by the fact that the adenine base is closer to the F223 ring than to the F7 ring. The structural and conformational properties of MeAdoMet in the active site of the hAdoMetDC F223A mutant was investigated.

The conformational searches with virtual mutations were done to understand the roles of F223 and F7 in stabilizing the syn conformation. In contrast to calculations done with the wild type enzyme structure, in which only the syn conformation was observed for the ensemble of low energy structure, the global minimum from both the mutations has the base in an anti conformation and the next higher energy structure has the base in a syn conformation. The difference in the energy between these conformations is about 0.5 kJ/mol, which is within the error limit of the molecular mechanics based calculations. The energy difference between the syn and anti conformation of both structures is low and the enzyme, in fact, prefers to bind the ligands in the syn conformation as seen from the X-ray structure of hAdoMetDC F223A with MeAdoMet bound in the active site. Thus, although the modeling studies were incapable of accurately predicting that the syn conformation of the nucleoside would be maintained in the F223A mutant, it was possible to infer from these studies that the binding affinity of the nucleoside for the enzyme would be diminished.

The data from the crystal structure of hAdoMetDC F223A with MeAdoMet shows a clear density of the adenine base in a syn conformation. The adenine base still maintains a favorable pi-pi interaction with the F7 residue and the ribose makes two key hydrogen bonds to E247. These findings show that one pair of pi-pi interaction and electrostatic interactions can hold the base in the syn conformation and that the F7 residue is instrumental in maintaining the conformation of MeAdoMet and other ligands in the active site.

The structures of AdoMetDC with MHZPA, MAOEA, MeAdoMet, MGBG and CGP48664A have shown that E247 is instrumental in making key hydrogen bonds to the ligands holding them in proper conformation to fit into the active site.[23] It is common for the ribose oxygens of most nucleosides to make key hydrogen bonds to aspartate, glutamate or carbonyl groups of the enzyme which hold them in a proper conformation for catalytic activity. In AdoMetDC, the ribose of AdoMet analogues is held in place by E247 through two hydrogen bonds which facilitate the Schiff base formation between the terminal nitrogen and the pyruvoyl group and also place the adenine base in a position to stack between the phenyl rings. The hAdoMetDC F223A crystal structure shows that the ribose of MeAdoMet still makes the two hydrogen bonds to E247 which tether it in the conformation which allows the adenine base to make favorable pi-pi interactions with F7 and attain a syn conformation.

The present disclosure establishes that adding a methyl group to the $C^8$ of adenine resulted in compounds that were 8 to 18-fold better inhibitors of the enzyme as compared to the un-substituted parent compounds and therefore is a preferred aspect of this disclosure. However, as mentioned above, the un-substituted parent compounds are also contemplated as being aspects within the scope of this disclosure. Certain compounds having larger substituents such as greater than 3 carbon atoms provided no benefit over the un-substituted parent compounds and therefore are not preferred aspects of this disclosure. In fact, the 8-phenyl substituent rendered the compounds much less able to inhibit hAdoMetDC. Modeling studies of the active site had indicated that there should be sufficient space to accommodate the larger groups with the adenine in the syn conformation. A more detailed look at the area occupied by adenine $C^8$ substituents has indicated that this area is near the solvent interface. Therefore, although there is, sterically, sufficient room for large substituents, those chosen were hydrophobic groups that would not be compatible with proximity to the solvent interface. Based on biochemical results, the penalty of incompletely burying a hydrophobic group within a hydrophobic cavity in the protein, which increases with the size of the substituted group, is apparently greater than the gain from biasing the inhibitor toward the syn conformation.

The compound 7a is structurally similar to the previously studied MAOEA and has a methyl substitution on the 8-position of the adenine base. The crystal structure of the complex of 7a with hAdoMetDc shows clear density for Schiff base formation with the pyruvoyl group, indicating that it acts similarly to MAOEA as an inhibitor of AdoMetDC. The ribose makes hydrogen bonds to E247, the adenine base stacks in a syn conformation, the 6-amino substituent of the adenine base makes a hydrogen bond with the backbone carboxyl group of E67, and the amide hydrogen of E67 is hydrogen bonded to $N^3$ of the adenine ring. The distance between the $N^3$ nitrogen which bears an appreciable negative charge and the tertiary nitrogen having a formal positive charge in its physiologically relevant protonated state is 2.94 Å, which is smaller than the distance found in MeAdoMet which has a sulfur atom in the corresponding position. The methyl substituent on the adenine ring also forces the base to attain a syn conformation and enhances the electrostatic effects thus explaining the decrease of the distance between the $N^3$ nitrogen and the tertiary nitrogen when compared to MHZPA and MAOEA, which have no substituent at the $C^8$ of adenine.

Structures of many of the AdoMet analogues bound to AdoMetDC have shown that they inhibit the enzyme through Schiff base formation with the pyruvoyl group of the enzyme. The linker length between the tertiary ammonium/sulfur and the terminal nitrogen of those inhibitors has been 3-4 atoms which makes the formation of a Schiff base geometrically and sterically feasible. 9e has a linker length of five atoms. The electron density map for the complex of 9e shows a break in the density after the pyruvoyl group which suggests that there is no Schiff base formation. There is good density for the ligand except at the three terminal atoms which are disordered and have no density. The position of the last three atoms was fixed in an energetically favorable conformation using molecular mechanics. The five atoms of the linker region appear to cause a sterically unfavorable situation for formation of the Schiff base. The ligand is held tightly in the active site by hydrogen bonds to E247 and the pi stacking interactions with F7 and F223 and thus little movement is allowed to accommodate that which appears to be needed to adjust to the longer linker region and accomplish Schiff base formation.

AdoMetDC can bind the substrate/ligands by initially interacting with the highly populated anti conformation in solution and then induce a rotation in the adenine base to the syn conformation or by binding to substrate/ligands already in the syn conformation, the solution equilibrium concentration of which is small, with only minor conformational changes required. The results suggest that 8-substitution increases the population of inhibitor molecules in the syn conformation thereby increasing the inhibition of AdoMetDC. The exact mechanism of ligand binding, however, by AdoMetDC is still not known.

Experimental Section

Mutagenesis and Plasmid Construction

Plasmids in the pQE30 vector for the production of recombinant wild type and F223A mutant hAdoMetDC in *E. coli* that was used for crystallography were produced as described previously.[23] This construct replaces the N-terminal methionine with MRGS(H)$_6$GS— for purification by immobilized metal affinity chromatography. A different plasmid also based on the pQE30 vector was used for the production of protein for the hAdoMetDC enzyme assays. In this plasmid, the (H)$_6$ tag was located at the carboxyl end replacing the terminal -QQQQQS. The position of the (H)$_6$ tag did not alter the activity of the purified enzyme.

Protein Expression and Purification

The wild type hAdoMetDC was purified based on the protocol described by Ekstrom et al.[20] The plasmid encoding the enzyme is in the pQE30 vector and was transformed into JM109 strain *E. coli* cells. The cells were grown as an overnight culture in LB media at 37° C. and then introduced into larger cell cultures with both of the cultures containing 100 mg/mL ampicillin. The cells were grown until they reached an O.D$_{600}$ of 0.6 and then were induced with 100 mg/L isopropyl1-thio-β-D galactopyranoside (IPTG). The cells were allowed to grow overnight at 15° C. and were then harvested by centrifugation, washed using a wash buffer which contained 20 mM Na$_2$HPO$_4$, pH 7.0, 500 mM NaCl, 2.5 mM putrescine, 0.02% Brij-35 and 10 mM imidazole, and stored at −80° C. The frozen cell pellet was thawed, suspended in the wash buffer, and lysed using a French press at 1500 psi. The cellular debris and the lysate were separated by centrifugation at 12000 g. Talon metal affinity resin was equilibrated with the wash buffer and then the lysate and the resin were gently spun together for 1.5 hours. The resin was loaded onto a column and washed with a volume of wash buffer equivalent to 15-20 times the column volume. Next, the column was washed in the same manner with wash buffer containing 25 mM imidazole. The protein was then eluted with buffer containing 100-200 mM imidazole. The eluted protein was concentrated to around 10 ml and passed through a Sephadex G-75 column pre-equilibrated with 10 mM Hepes, pH 7.5, 2.5 mM putrescine, 5 mM DTT, 0.1 mM EDTA, 0.02% Brij-35, and 300 mM NaCl. The buffer was run through the column and the fractions containing the protein were identified by UV at 280 nm. The protein was concentrated to ~10 mg/mL and stored at −80° C. The purification of the F223A mutant was similar to that of the native enzyme.

Crystallization

The protein was thawed on ice and buffer exchanged to 10 mM Hepes, pH 7.5, 200 mM NaCl and 1 mM DTT using Bio-rad buffer exchange chromatography columns (Bio-rad Laboratories, Hercules, Calif. 94547). The native protein was incubated with a 4-6 molar excess of 9e and 7a for 24 hours prior to crystallization. The F223A mutant was diluted to ~6 mg/mL and incubated with a 4-6 molar excess of MeAdoMet for 24 hours prior to crystallization. Crystals of both the native and the mutant complexes were grown using the hanging drop method at 22° C. in 13-16% PEG 8000, 100 mM Tris, pH 8.0-9.0, and 10 mM DTT. Crystals appeared overnight and were stable for 1-2 weeks.

Data Collection and Processing

The data for the 7a complex was collected at home source on a Bruker CCD detector with a Cu Kα radiation from a Rigaku RU-300 rotating anode generator. The data for the 9e complex was collected at the 8BM station of NE-CAT beam line at the Advanced Photon Source (APS) using a ADSC quantum 315 detector. The data for AdoMetDC F223A with MeAdoMet was collected at the F2 station of CHESS using an ADSC Quantum 4 detector. All the crystals were flash frozen under liquid nitrogen or liquid nitrogen stream. The diffraction quality of the crystals strongly depended on the cryoprotection of the crystals. The crystals were sequentially transferred to a solution containing the well solution with 2%, 5%, 8%, 15% and 18% glycerol with 1-2 min equilibration between each step.

The data for all of the complexes was indexed, integrated and scaled using the HKL2000 (24) program suite. The data collection statistics are summarized in Table 1.

Structure Determination and Refinement

The structures of all of the complexes were determined by molecular replacement using the structure of native AdoMetDC with MeAdoMet bound (PDB 1I7B) as the search model, and the CNS program suite.[25] The model building for the 7a and 9e complex was done using the program O.[26] The model building for AdoMetDC F223A complexed with MeAdoMet was done by using program coot.[27] The conformations of the ligand molecules were determined by the difference fo-fc and the composite omit maps. The parameters and the topology files for the ligands were generated using the hic-up server.[28] The difference maps also showed density for a molecule of putrescine bound in all three of the structures. The refinement statistics of the complexes are given in Table 2.

Molecular Modeling of MeAdoMet in the Active Site of AdoMetDC

Determination of the conformational preference of ligands in the active site of AdoMetDC was carried out with Macromodel version 7.2[29] available from Schrödinger, L. L. C. The protein was truncated to a shell of atoms that included any residue that contained an atom within 20.0 Å of MeAdoMet located in the active site of AdoMetDC (from pdb 1I7B) and was used as the starting model for conformational searching/energy minimization. Removal of water molecules from this "docking shell" was followed by appropriate hydrogen treatment aided by Schrödinger's protein preparation utility that aids in the generation of appropriate ionic states and histidine tautomers for active site amino acids and minimizes the protein's potential energy gradient through a series of constrained energy minimizations. For the conformational searches, the appropriate ligand was added to the active site and, where appropriate, the covalent bond between the amino terminus of the ligand and the pyruvoyl group was made.

The resulting structures were subjected to 50,000 mixed Monte Carlo MCMM/Low Mode conformational search steps[30,31] allowing residues within a 5 Å shell surrounding the active site to freely move during each Monte Carlo/Low Mode step and subsequent energy minimization step of the search. All other protein atoms were constrained to their starting position. Residues H5, E67, C226 and E247 were also constrained to their starting position. The energy minimization step was considered to have converged when the energy gradient was less than 0.05 kJ/mol. The AMBER* force field,[32,33] with a distance dependent dielectric "constant" further attenuated by a factor of 4 was employed for the calculations, and the energy minimizations relied upon the TNCG minimization technique.[34] The global minimum and low energy ensemble of structures within 15 kJ/mol of the global minimum (after convergence) were further refined by energy minimization until a gradient less than 0.01 kJ/mol was obtained with just the ligand allowed to move during this subsequent energy minimization procedure. All protein atoms during this process were constrained to their starting position. The jobs were run with the nucleoside starting in both the syn and anti conformations for completeness. The AMBER* parameters for the sulfonium ion were adapted from the work done by Dr. Markham et al.[35]

Modeling of 9e in the Active Site of AdoMetDC

The modeling of the terminal three atoms of 9e was done by using conformational searching with Macromodel version 7.2 as described above. Since the position of the rest of the ligand and the protein was determined to high accuracy by fitting to the electron density determined by X-ray diffraction, all of the protein and the ligand atoms except the last three non-hydrogen atoms and their attached hydrogens were fixed during the conformational search. Torsional rotation was allowed around C5-C4 and C4-O1 bonds during the conformational search. A quick look at the top 5 minimum structures showed that they were similar and the global minimum of the search was utilized to obtain the coordinates of the disordered terminal atoms of 9e.

Assay of AdoMetDC Activity and Determination of Inhibitor $IC_{50}$ Values

AdoMetDC was assayed by measuring the release of $^{14}CO_2$ from S-adenosyl-L-[carboxy-$^{14}$C]methionine (Amersham Pharmacia Biotech, ~60 mCi/mmol) (36). Assay of 30 ng of C-terminal his-tagged AdoMetDC under these conditions results in ~7000 cpm with a background of 30, and an activity of ~1.5 pmol/mining protein. For determination of the abilities of compounds to inhibit AdoMetDC, the enzyme activity was determined in the presence of no inhibitor and at least 5 concentrations of each potential inhibitor. The $IC_{50}$ values were determined from curve fitting to plots of the inhibitor concentration versus the % inhibition of AdoMetDC.

Target Synthesis

TLC analysis was performed on Analtech precoated (250 μm) silica gel GF plates. Melting points were determined on a Mel-Temp apparatus and are uncorrected. Purifications by flash chromatography were carried out on Merck silica gel (230-400 mesh). Evaporations were performed with a rotary evaporator, higher boiling solvents (DMF, pyridine) were removed in vacuo (<1 mm, bath to 35° C.). Products were dried in vacuo (<1 mm) at 22-25° C. over $P_2O_5$. The mass spectral data were obtained with a Varian-MAT 311A mass spectrometer in the fast atom bombardment (FAB) mode or with Bruker BIOTOF II by electrospray ionization (ESI). $^1$HNMR spectra were recorded on a Nicolet NT-300 NB spectrometer operating at 300.635 MHz. Chemical shifts in $CDCl_3$ and $Me_2SO$-$d_6$ are expressed in parts per million downfield from tetramethylsilane (TMS) and in $D_2O$ Chemical shifts are expressed in parts per million downfield from sodium 3-(trimethylsilyl)propionate-2,2,3,3-$d_4$ (TMSP). Chemical shifts (δ) listed for multiplets were measured from the approximate centers, and relative integrals of peak areas agreed with those expected for the assigned structures. UV absorption spectra were determined on a Perkin-Elmer Lambda 19 spectrometer by dissolving each compound in MeOH or EtOH, and diluting 10-fold with 0.1 N HCl, pH 7 buffer, or 0.1 N NaOH. Numbers in parentheses are extinction coefficients ($\epsilon \times 10^{-3}$). Microanalyses were performed by Atlantic Microlab, Inc. (Atlanta, Ga.) or the Spectroscopic and Analytical Department of Southern Research Institute. Analytical results indicated by element symbols were within ±0.4% of the theoretical values, and where solvents are indicated in the formula, their presence was confirmed by $^1$HNMR.

In solution, AdoMet maintains a range of conformations from syn to anti and in between. AdoMetDC can bind the substrate/ligands by picking up the highly populated anti conformation and then rotating the adenine base to the syn conformation or by picking up ligands in the syn conformation from the solution directly with no conformational change needed. The above results have shown that the presence of ligand with the syn conformation populated increases the inhibition of AdoMetDC. The exact mechanism of ligand binding by AdoMetDC is still not known.

TABLE 1

Data collection statistics for AdoMetDC complexes.

|  | hAdoMetDC F223A + MeAdoMet | hAdoMetDC + 7a | hAdoMetDC + 9e |
|---|---|---|---|
| Wavelength | 0.9795 | 1.5418 | 0.9795 |
| Space Group (Å) | C2 | C2 | C2 |
| a (Å) | 95.98 | 96.78 | 94.43 |
| b (Å) | 44.25 | 44.46 | 50.04 |
| c (Å) | 70.83 | 70.55 | 70.41 |
| β | 104.52 | 104.17 | 105.34 |
| Resolution (Å) | 2.62 | 2.43 | 1.83 |
| Total/Unique reflections | 23532/8160 | 26010/10403 | 83134/26894 |
| Redundancy | 2.9(2.6) | 2.5(1.9) | 3.1(3.1) |
| % complete | 92.9(91.2) | 93.6(86.8) | 95.6(95.5) |
| I/σ | 13.3(2.0) | 10.9(2.9) | 13.5(2.7) |
| Rsym | 7.7(45.2) | 9.0(33.8) | 7.2(54.8) |
| Matthews no | 1.90 | 1.92 | 2.09 |
| Solvent content | 34.07 | 34.77 | 39.67 |

Values in parenthesis are for the highest resolution shell.

TABLE 2

Refinement statistics for AdoMetDC complexes.

|  | hAdoMetDC F223A + MeAdoMet | hAdoMetDC + 7a | hAdoMetDC + 9e |
|---|---|---|---|
| Resolution (Å) | 2.62 | 2.43 | 1.83 |
| R-factor | 0.198 | 0.191 | 0.204 |
| R-free | 0.278 | 0.247 | 0.233 |
| No of non-H atoms |  |  |  |
| Protein | 2511 | 2437 | 2400 |
| Ligand | 28 | 25 | 29 |
| Water | 78 | 80 | 140 |
| B-factors |  |  |  |
| Protein (Å$^2$) | 43.1 | 33.2 | 31.0 |
| Ligand (Å$^2$) | 57.9 | 39.6 | 34.1 |
| Putrescine (Å$^2$) | 37.8 | 28.8 | 43.0 |
| rms deviations |  |  |  |
| bonds (Å) | 0.008 | 0.008 | 0.006 |
| angles | 1.3 | 1.3 | 1.2 |
| dihedrals | 24.7 | 24.6 | 24.9 |
| Ramachandran plot |  |  |  |
| Most favored region (%) | 83.8 | 89.4 | 90.7 |
| Additional favored region (%) | 15.5 | 8.7 | 8.1 |
| Generously allowed region (%) | 0.4 | 1.5 | 0.8 |
| Disallowed region (%) | 0.4 | 0.4 | 0.4 |

TABLE 3

Ability of potential inhibitors to inhibit hAdoMetDC. Each of the potential inhibitors were assayed as described in "Materials and Methods" for the ability to inhibit hAdoMetDC. At least 5 concentrations of each compound were used and $IC_{50}$ values were calculated from curve fits to plots of inhibitor concentration versus % inhibition of hAdoMetDC.

| Compound | IC50 |
|---|---|
| 7a | 7 nM |
| 7b | 86 nM |
| 7c | <5% inhibition at 100 μM |
| 9a | 49 nM |
| 9b | <5% inhibition at 100 μM |
| 9c | 11 nM |
| 9d | 5 nM |
| 9e | 15 nM |
| 9f | 18 nM |
| 12 (MAOEA) | 55 nM |
| 13d | 400 nM |
| 13e | 4 μM |
| 13f | <5% inhibition at 100 μM |
| 13j | 7 μM |
| 13k | 170 nM |
| 13l | 1.5 μM |
| 13m | 31 μM |
| 14a | 440 μM |
| 14b | <5% inhibition at 100 μM |
| 14d | 500 μM |
| 14e | <5% inhibition at 100 μM |
| 14f | 88 μM |
| 15a | <5% inhibition at 100 μM |
| 15b | <5% inhibition at 100 μM |
| 15c | <5% inhibition at 100 μM |
| 15d | <5% inhibition at 100 μM |
| 17c | 70 μM |
| 17d | 420 μM |
| 18a | <5% inhibition at 100 μM |
| 18c | 157 μM |
| 19a | 600 nM |
| 19b | 9 μM |
| 21b | 3 μM |
| 21d | 15 μM |

Figure Legends

The following table shows the formulae for various compounds according to the present disclosure.

|  |  | Calculated, % | | | | Found, % | | | |
|---|---|---|---|---|---|---|---|---|---|
| Compound | Empirical Formula | C | H | N | S | C | H | N | S |
| 7a | $C_{14}H_{23}N_7O_4 \cdot 2.2H_2SO_4 \cdot 0.1C_2H_5OH \cdot 0.5H_2O$ | 29.26 | 5.01 | 16.82 |  | 29.48 | 5.21 | 16.47 |  |
| 7b | $C_{14}H_{24}N_8O_4 \cdot 2.1H_2SO_4 \cdot 0.3C_2H_5OH \cdot 0.2H_2O$ | 29.63 | 5.17 | 18.93 | 11.37 | 29.43 | 5.20 | 19.05 | 11.13 |
| 7c | $C_{19}H_{25}N_7O_4 \cdot 2.0H_2SO_4 \cdot 3H_2O$ | 34.28 | 5.29 | 14.72 | 9.63 | 34.21 | 5.34 | 14.59 | 9.59 |
| 9a | $C_{16}H_{28}N_8O_4 \cdot 0.4H_2SO_4 \cdot 0.2C_2H_5OH \cdot 0.9H_2O$ | 42.71 | 6.95 | 24.30 | 2.78 | 42.53 | 6.84 | 24.16 | 2.56 |
| 9b | $C_{21}H_{29}N_7O_4 \cdot 1.75H_2SO_4 \cdot 0.05C_2H_5OH \cdot 2.4H_2O$ | 38.36 | 5.73 | 14.84 | 8.49 | 38.23 | 5.74 | 14.78 | 8.59 |
| 9c | $C_{15}H_{25}N_7O_5 \cdot 1.9H_2SO_4 \cdot 0.1C_2H_5OH \cdot 2H_2O$ | 29.91 | 5.51 | 16.06 | 9.98 | 30.03 | 5.49 | 16.14 | 9.74 |
| 9d | $C_{16}H_{27}N_7O_4 \cdot 1.9H_2SO_4 \cdot 0.4C_2H_5OH$ | 34.42 | 5.70 | 16.71 |  | 34.56 | 5.67 | 16.70 |  |
| 9e | $C_{17}H_{29}N_7O_4 \cdot 1.9H_2SO_4 \cdot 0.2C_2H_5OH$ | 35.36 | 5.79 | 16.58 |  | 35.49 | 5.87 | 16.61 |  |
| 9f | $C_{15}H_{25}N_7O_4 \cdot 2.0H_2SO_4 \cdot 0.3C_2H_5OH \cdot 1.5H_2O$ | 30.99 | 5.65 | 16.22 | 10.61 | 31.02 | 5.40 | 16.30 | 10.49 |
| 12 | $C_{13}H_{21}N_7O_4 \cdot 1.0H_2SO_4 \cdot 0.5C_2H_5OH \cdot 1.0H_2O$ | 35.14 | 5.90 | 20.49 |  | 34.91 | 6.06 | 20.69 |  |
| 13c | $C_{16}H_{24}N_6O_5 \cdot 0.5CHCl_3 \cdot 0.3CH_3OH$ | 49.59 | 6.19 | 21.22 |  | 49.72 | 6.29 | 21.17 |  |
| 13d | $C_{15}H_{23}N_7O_4 \cdot 1.5H_2SO_4 \cdot 0.8H_2O$ | 34.19 | 5.27 | 18.60 | 9.12 | 34.34 | 5.03 | 18.45 | 9.12 |
| 13e | $C_{16}H_{25}N_7O_4 \cdot 1.1H_2SO_4 \cdot 1.05H_2O$ | 37.96 | 5.83 | 19.36 | 6.95 | 37.64 | 5.84 | 19.43 | 6.81 |
| 13f | $C_{14}H_{21}N_7O_4 \cdot 1.45H_2SO_4 \cdot 0.2C_2H_5OH \cdot 1.3H_2O$ | 32.55 | 5.18 | 18.92 | 8.97 | 32.35 | 5.24 | 18.87 | 8.80 |
| 13j | $C_{14}H_{21}N_7O_4 \cdot 1.9H_2SO_4 \cdot 1.6H_2O$ | 29.68 | 4.98 | 17.31 | 10.75 | 29.54 | 4.68 | 17.05 | 10.64 |
| 13k | $C_{15}H_{24}N_8O_4 \cdot 2.0H_2SO_4 \cdot 2.7H_2O$ | 28.81 | 5.38 | 17.92 | 10.25 | 28.93 | 5.30 | 17.66 | 10.19 |
| 13l | $C_{14}H_{22}N_8O_4 \cdot 2.0H_2SO_4 \cdot 2.0H_2O$ | 28.09 | 5.05 | 18.72 | 10.71 | 27.81 | 5.14 | 19.10 | 10.51 |
| 13m | $C_{14}H_{22}N_8O_4 \cdot 0.2CH_3OH \cdot 0.4H_2O$ | 44.88 | 6.25 | 29.48 |  | 44.91 | 6.17 | 29.44 |  |
| 14a | $C_{15}H_{26}N_8O_3 \cdot 2.4H_2SO_4 \cdot 0.2C_2H_5OH$ | 30.27 | 5.27 | 18.34 |  | 30.25 | 5.28 | 18.54 |  |
| 14b | $C_{20}H_{27}N_8O_3 \cdot 2.2H_2SO_4 \cdot 0.1C_2H_5OH \cdot 2.5H_2O$ | 28.45 | 1.36 | 4.74 |  | 28.75 | 1.38 | 4.79 |  |
| 14d | $C_{14}H_{23}N_7O_3 \cdot 2.0H_2SO_4 \cdot 0.25C_2H_5OH \cdot 0.7H_2O$ | 31.23 | 5.40 | 17.58 |  | 31.21 | 5.49 | 17.48 |  |
| 14e | $C_{13}H_{21}N_7O_3 \cdot 0.25CHCl_3 \cdot 0.5H_2O$ | 47.80 | 7.24 | 27.09 |  | 47.76 | 7.13 | 27.03 |  |
| 14f | $C_{14}H_{23}N_7O_3 \cdot 0.5CH_3OH \cdot 0.3H_2O$ | 48.53 | 7.19 | 27.32 |  | 48.73 | 7.17 | 27.09 |  |
| 15a | $C_{15}H_{26}N_8O_3 \cdot 2.4H_2SO_4 \cdot 0.2C_2H_5OH$ | 35.73 | 5.49 | 14.44 |  | 35.92 | 5.39 | 14.49 |  |
| 15b | $C_{20}H_{27}N_8O_3 \cdot 1.7H_2SO_4 \cdot 0.05C_2H_5OH \cdot 3.3H_2O$ | 37.32 | 5.82 | 15.15 | 8.67 | 37.29 | 5.79 | 15.18 | 8.40 |
| 15c | $C_{13}H_{21}N_7O_3 \cdot 0.05CH_3OH \cdot 0.1H_2O$ | 47.97 | 6.60 | 30.00 |  | 47.70 | 6.86 | 29.95 |  |
| 15d | $C_{14}H_{23}N_7O_3 \cdot 0.4CH_3OH \cdot 0.7H_2O$ | 43.93 | 6.19 | 27.06 |  | 44.15 | 6.27 | 27.18 |  |
| 17c | $C_{15}H_{25}N_7O_3 \cdot 2.0H_2SO_4 \cdot 2.5H_2O$ | 30.40 | 5.78 | 16.54 | 10.52 | 30.55 | 5.85 | 16.19 | 10.82 |
| 17d | $C_{16}H_{27}N_7O_3 \cdot 2.5H_2SO_4 \cdot 2.5H_2O$ | 29.72 | 5.61 | 15.16 |  | 29.86 | 5.57 | 14.81 |  |
| 18a | $C_{14}H_{23}N_9O_3 \cdot 0.05CHCl_3 \cdot 3.5H_2O$ | 38.84 | 6.97 | 29.01 |  | 38.54 | 6.65 | 29.25 |  |
| 18c | $C_{14}H_{22}N_8O_4 \cdot 1.2C_2H_5OH \cdot 0.2CH_3OH$ | 46.58 | 7.06 | 26.18 |  | 46.93 | 7.22 | 26.43 |  |
| 19a | $C_{13}H_{20}N_6O_3 \cdot 0.35CHCl_3 \cdot 0.5C_2H_5OH$ | 45.43 | 6.14 | 22.95 |  | 45.54 | 5.85 | 22.79 |  |
| 19b | $C_{12}H_{18}N_6O_3 \cdot 0.35CH_3OH$ | 48.55 | 6.40 | 27.50 |  | 48.80 | 6.40 | 27.23 |  |
| 21b | $C_{13}H_{20}ClN_5O_3S \cdot 2H_2O$ | 39.24 | 6.07 | 17.60 |  | 39.35 | 5.97 | 17.55 |  |
| 21d | $C_{12}H_{18}ClN_5O_3S \cdot 1.5H_2O \cdot 0.1C_2H_5OH$ | 38.96 | 5.80 | 18.32 | 8.44 | 38.98 | 5.68 | 18.29 | 8.57 |

Disclosed compounds in this application have been found to inhibit S-adenosylmethionine decarboxylase and therefore are potentially useful in treating tumors and cancers in a mammal and especially humans. In addition, compounds in this application are useful in treating parasitic infections, such as protozoal infections including trypanosomiasis, malaria, or infections pulmonary inflammation caused by *Pneumocystis cainii* such as pulmonary inflammation.

Discussion of Figures

FIG. 1: Crystal structure of hAdoMetDC and comparison to a structure derived from modeling. A. Shown is the actual crystal structure of hAdoMetDC with MeAdoMet in the active site. The active site pyruvoyl group is shown in magenta. The ligand carbon atoms are shown in green. MeAdoMet makes a Schiff base to the pyruvoyl group. The ribose makes two hydrogen bonds to E247 (shown in red). The adenine base stacks between F223 and F7 in the unusual syn conformation. The hydrogen bonds between the adenine base and the backbone of Glu67 stabilize the syn conformation.

B. The structure derived from modeling of MeAdoMet in the active site of AdoMetDC (shown in darker shade) is superimposed on the actual crystal structure (shown in lighter shape). The modeling result agrees well with the experimentally determined crystal structure.

FIG. 2: Modeling of hAdoMetDC F223A and hAdoMetDC F7A complexed with MeAdoMet.

Global minimum of modeling of MeAdoMet in the active site of the F223A mutant (A.) and the F7A mutant (B.) of hAdoMetDC (see Materials and Methods for details). The pyruvoyl group is shown as the next to darkest shade and the ligand carbon atoms are shown as the next to lightest shade. The adenine base attains an anti conformation in these complexes. The ribose makes one hydrogen bond to E247 and the other to the backbone carbonyl of C226. The adenine base makes three hydrogen bonds to S66. In the F7A model (B.) the F223 residue changes its conformation to stack with the adenine base of MeAdoMet in the anti conformation.

FIG. 3: Crystal structure of MeAdoMet in the active site of the AdoMetDC F223A mutant.

Shown is the experimentally determined (see Materials and Methods") structure of the complex of MeAdoMet with AdoMetDC F223A. The carbon atoms of the ligand and the connecting chain are shown as the next to lightest shade. The 1fo-fc density contoured at 2.5σ shows the adenine base in the syn conformation and the formation of a Schiff base between the terminal nitrogen and the pyruvoyl group. The pyruvoyl group and the S69 residue are omitted for the calculation of the map. The ribose makes two key hydrogen bonds to E247. The adenine ring stacks with F7 and makes two hydrogen bonds to the backbone of E67.

FIG. 4: Structures of potential inhibitors of hAdoMetDC. All compounds were synthesized as described in "Materials and Methods".

Figures 5A, 5B:
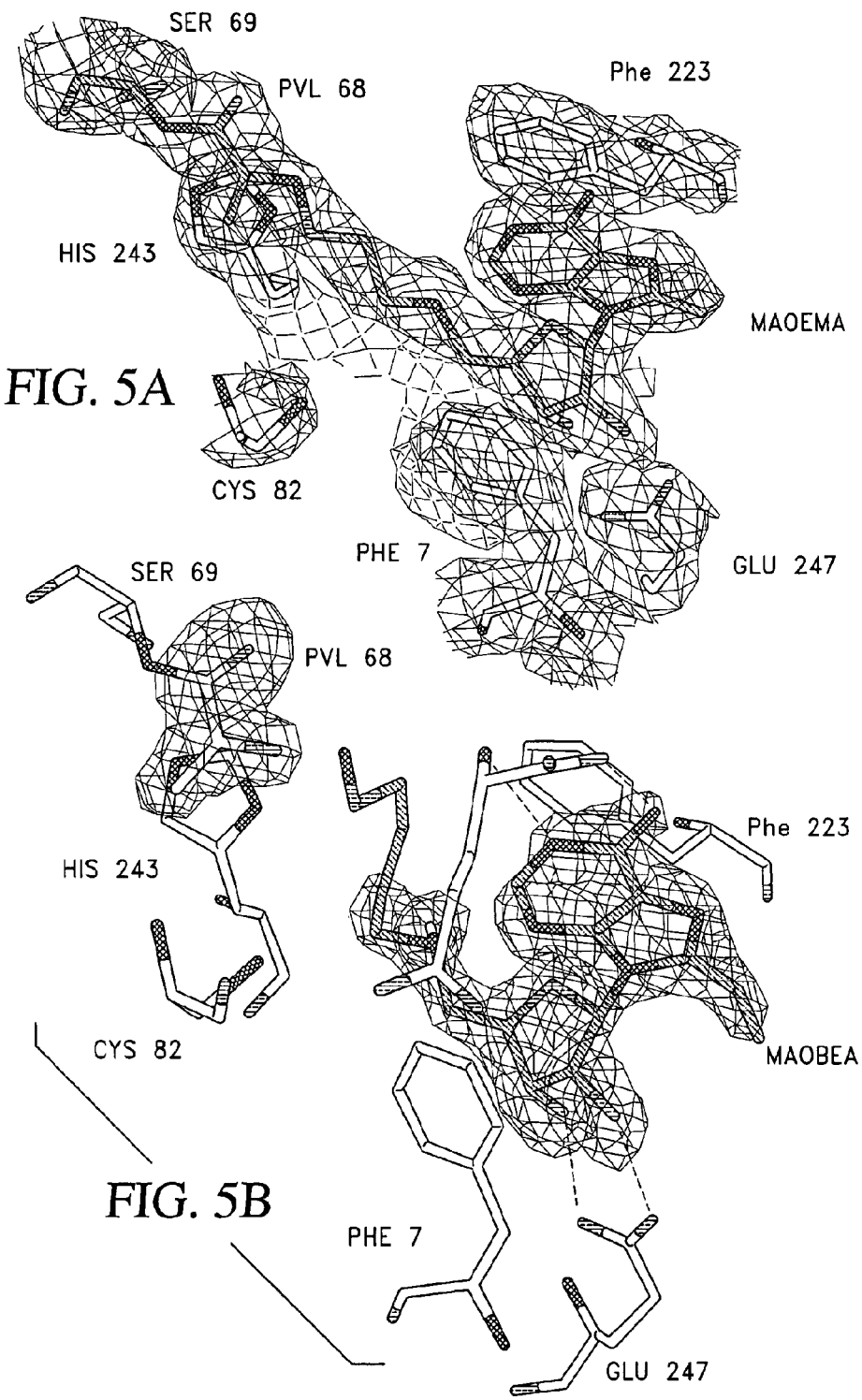
FIG. 5 illustrates interaction of hAdoMetDC with two inhibitors of the enzyme.

FIG. 5: Interaction of hAdoMetDC with two inhibitors of the enzyme. A. The experimentally determined structure of the complex of hAdoMetDC with MAOEMA is shown (see Materials and Methods for details). The carbon atoms of the ligand and the connecting chain are shown as the next to lightest shade.

The composite omit map density contoured at 1.0σ shows the adenine base stacking in the syn conformation and the formation of the Schiff base. E67 has been omitted for clarity. B. The experimentally determined structure of hAdoMetDC with MAOBEA in the active site is shown. The ligand carbon atoms are shown as the next to lightest shade. The 1fo-fc density contoured at 3.0σ shows that the adenine base stacks in the syn conformation. There is no evidence from the electron density for the formation of a Schiff base and there is no density for the terminal three atoms of the ligand. The pyruvoyl group is omitted for the calculation of the map. The position of the last three atoms is determined by modeling.

Formulations

The compounds of the present disclosure can be administered by any conventional means available for use in conjunction with pharmaceuticals, either as individual therapeutic agents or in a combination of therapeutic agents. They can be administered alone, but generally administered with a pharmaceutical carrier selected on the basis of the chosen route of administration and standard pharmaceutical practice. The compounds can also be administered in conjunction with other therapeutic agents such as interferon (IFN), interferon α-2a, interferon α-2b, consensus interferon (CIFN), ribavirin, amantadine, remantadine, interleukine-12, ursodeoxycholic acid (UDCA), and glycyrrhizin.

The pharmaceutically acceptable carriers described herein, for example, vehicles, adjuvants, excipients, or diluents, are well-known to those who are skilled in the art. Typically, the pharmaceutically acceptable carrier is chemically inert to the active compounds and has no detrimental side effects or toxicity under the conditions of use. The pharmaceutically acceptable carriers can include polymers and polymer matrices.

The compounds of this disclosure can be administered by any conventional method available for use in conjunction with pharmaceuticals, either as individual therapeutic agents or in a combination of therapeutic agents.

The dosage administered will, of course, vary depending upon known factors, such as the pharmacodynamic characteristics of the particular agent and its mode and route of administration; the age, health and weight of the recipient; the nature and extent of the symptoms; the kind of concurrent treatment; the frequency of treatment; and the effect desired. A daily dosage of active ingredient can be expected to be about 0.001 to 1000 milligrams (mg) per kilogram (kg) of body weight, with the preferred dose being 0.1 to about 30 mg/kg.

Dosage forms (compositions suitable for administration) contain from about 1 mg to about 500 mg of active ingredient per unit. In these pharmaceutical compositions, the active ingredient will ordinarily be present in an amount of about 0.5-95% weight based on the total weight of the composition.

The active ingredient can be administered orally in solid dosage forms, such as capsules, tablets, and powders, or in liquid dosage forms, such as elixirs, syrups and suspensions. It can also be administered parenterally, in sterile liquid dosage forms. The active ingredient can also be administered intranasally (nose drops) or by inhalation of a drug powder mist. Other dosage forms are potentially possible such as administration transdermally, via patch mechanism or ointment.

Formulations suitable for oral administration can contain (a) liquid solutions, such as an effective amount of the compound dissolved in diluents, such as water, saline, or orange juice; (b) capsules, sachets, tablets, lozenges, and troches, each containing a predetermined amount of the active ingredient, as solids or granules; (c) powders; (d) suspensions in an appropriate liquid; and (e) suitable emulsions. Liquid formulations may include diluents, such as water and alcohols, for example, ethanol, benzyl alcohol, propylene glycol, glycerin, and the polyethylene alcohols, either with or without the addition of a pharmaceutically acceptable surfactant, suspending agent, or emulsifying agent. Capsule forms can be of the ordinary hard- or soft-shelled gelatin type containing, for example, surfactants, lubricants, and inert fillers, such as lactose, sucrose, calcium phosphate, and corn starch. Tablet forms can include one or more of the following: lactose, sucrose, mannitol, corn starch, potato starch, alginic acid, microcrystalline cellulose, acacia, gelatin, guar gum, colloidal silicon dioxide, croscarmellose sodium, talc, magnesium stearate, calcium stearate, zinc stearate, stearic acid, and other excipients, colorants, diluents, buffering agents, disintegrating agents, moistening agents, preservatives, flavoring agents, and pharmacologically compatible carriers. Lozenge forms can comprise the active ingredient in a flavor, usually sucrose and acacia or tragacanth, as well as pastilles comprising the active ingredient in an inert base, such as gelatin and glycerin, or sucrose and acadia, emulsions, and gels containing, in addition to the active ingredient, such carriers as are known in the art.

The compounds of the present disclosure, alone or in combination with other suitable components, can be made into aerosol formulations to be administered via inhalation. These aerosol formulations can be placed into pressurized acceptable propellants, such as dichlorodifluoromethane, propane, and nitrogen. They also may be formulated as pharmaceuticals for non-pressured preparations, such as in a nebulizer or an atomizer.

Formulations suitable for parenteral administration include aqueous and non-aqueous, isotonic sterile injection solutions, which can contain anti-oxidants, buffers, bacteriostats, and solutes that render the formulation isotonic with the blood of the intended recipient, and aqueous and non-aqueous sterile suspensions that can include suspending agents, solubilizers, thickening agents, stabilizers, and preservatives. The compound can be administered in a physiologically acceptable diluent in a pharmaceutical carrier, such as a sterile liquid or mixture of liquids, including water, saline, aqueous dextrose and related sugar solutions, an alcohol, such as ethanol, isopropanol, or hexadecyl alcohol, glycols, such as propylene glycol or polyethylene glycol such as poly(ethyleneglycol) 400, glycerol ketals, such as 2,2-dimethyl-1,3-dioxolane-4-methanol, ethers, an oil, a fatty acid, a fatty acid ester or glyceride, or an acetylated fatty acid glyceride with or without the addition of a pharmaceutically acceptable surfactant, such as a soap or a detergent, suspending agent, such as pectin, carbomers, methylcellulose, hydroxypropylmethylcellulose, or carboxymethylcellulose, or emulsifying agents and other pharmaceutical adjuvants.

Oils, which can be used in parenteral formulations, include petroleum, animal, vegetable, or synthetic oils. Specific examples of oils include peanut, soybean, sesame, cottonseed, corn, olive, petrolatum, and mineral. Suitable fatty acids for use in parenteral formulations include oleic acid, stearic acid, and isostearic acid. Ethyl oleate and isopropyl myristate are examples of suitable fatty acid esters. Suitable soaps for use in parenteral formulations include fatty alkali metal, ammonium, and triethanolamine salts, and suitable detergents include (a) cationic detergents such as, for example, dimethyldialkylammonium halides, and alkylpyridinium halides, (b) anionic detergents such as, for example, alkyl, aryl, and olefin sulfonates, alkyl, olefin, ether, and monoglyceride sulfates, and sulfosuccinates, (c) nonionic detergents such as, for example, fatty amine oxides, fatty acid alkanolamides, and polyoxyethylene polypropylene copolymers, (d) amphoteric detergents such as, for example, alkyl β-aminopropionates, and 2-alkylimidazoline quaternary ammonium salts, and (e) mixtures thereof.

The parenteral formulations typically contain from about 0.5% to about 25% by weight of the active ingredient in solution. Suitable preservatives and buffers can be used in such formulations. In order to minimize or eliminate irritation at the site of injection, such compositions may contain one or more nonionic surfactants having a hydrophile-lipophile balance (HLB) of from about 12 to about 17. The quantity of surfactant in such formulations ranges from about 5% to about 15% by weight. Suitable surfactants include polyethylene sorbitan fatty acid esters, such as sorbitan monooleate and the high molecular weight adducts of ethylene oxide with a hydrophobic base, formed by the condensation of propylene oxide with propylene glycol.

Pharmaceutically acceptable excipients are also well-known to those who are skilled in the art. The choice of excipient will be determined in part by the particular compound, as well as by the particular method used to administer the composition. Accordingly, there is a wide variety of suitable formulations of the pharmaceutical composition of the present disclosure. The following methods and excipients are merely exemplary and are in no way limiting. The pharmaceutically acceptable excipients preferably do not interfere with the action of the active ingredients and do not cause adverse side-effects. Suitable carriers and excipients include solvents such as water, alcohol, and propylene glycol, solid absorbants and diluents, surface active agents, suspending agent, tableting binders, lubricants, flavors, and coloring agents.

The formulations can be presented in unit-dose or multi-dose sealed containers, such as ampules and vials, and can be stored in a freeze-dried (lyophilized) condition requiring only the addition of the sterile liquid excipient, for example, water, for injections, immediately prior to use. Extemporaneous injection solutions and suspensions can be prepared from sterile powders, granules, and tablets. The requirements for effective pharmaceutical carriers for injectable compositions are well known to those of ordinary skill in the art. See *Pharmaceutics and Pharmacy Practice*, J.B. Lippincott Co., Philadelphia, Pa., Banker and Chalmers, Eds., 238-250 (1982) and *ASHP Handbook on Injectable Drugs*, Toissel, 4th ed., 622-630 (1986).

Formulations suitable for topical administration include lozenges comprising the active ingredient in a flavor, usually sucrose and acacia or tragacanth; pastilles comprising the active ingredient in an inert base, such as gelatin and glycerin, or sucrose and acacia; and mouthwashes comprising the active ingredient in a suitable liquid carrier; as well as creams, emulsions, and gels containing, in addition to the active ingredient, such carriers as are known in the art.

Additionally, formulations suitable for rectal administration may be presented as suppositories by mixing with a variety of bases such as emulsifying bases or water-soluble bases. Formulations suitable for vaginal administration may be presented as pessaries, tampons, creams, gels, pastes, foams, or spray formulas containing, in addition to the active ingredient, such carriers as are known in the art to be appropriate.

Suitable pharmaceutical carriers are described in Remington's Pharmaceutical Sciences, Mack Publishing Company, a standard reference text in this field.

The dose administered to an animal, particularly a human, in the context of the present disclosure should be sufficient to affect a therapeutic response in the animal over a reasonable time frame. One skilled in the art will recognize that dosage will depend upon a variety of factors including a condition of the animal, the body weight of the animal, as well as the severity and stage of the condition being treated.

A suitable dose is that which will result in a concentration of the active agent in a patient which is known to affect the desired response. The preferred dosage is the amount which results in maximum inhibition of the condition being treated, without unmanageable side effects.

The size of the dose also will be determined by the route, timing and frequency of administration as well as the existence, nature, and extend of any adverse side effects that might accompany the administration of the compound and the desired physiological effect.

Useful pharmaceutical dosage forms for administration of the compounds according to the present disclosure can be illustrated as follows:

Hard Shell Capsules

A large number of unit capsules are prepared by filling standard two-piece hard gelatine capsules each with 100 mg of powdered active ingredient, 150 mg of lactose, 50 mg of cellulose and 6 mg of magnesium stearate.

Soft Gelatin Capsules

A mixture of active ingredient in a digestible oil such as soybean oil, cottonseed oil or olive oil is prepared and injected by means of a positive displacement pump into molten gelatin to form soft gelatin capsules containing 100 mg of the active ingredient. The capsules are washed and dried. The active ingredient can be dissolved in a mixture of polyethylene glycol, glycerin and sorbitol to prepare a water miscible medicine mix.

Tablets

A large number of tablets are prepared by conventional procedures so that the dosage unit was 100 mg of active ingredient, 0.2 mg. of colloidal silicon dioxide, 5 mg of magnesium stearate, 275 mg of microcrystalline cellulose, 11 mg. of starch, and 98.8 mg of lactose. Appropriate aqueous and non-aqueous coatings may be applied to increase palatability, improve elegance and stability or delay absorption.

Immediate Release Tablets/Capsules

These are solid oral dosage forms made by conventional and novel processes. These units are taken orally without water for immediate dissolution and delivery of the medication. The active ingredient is mixed in a liquid containing ingredient such as sugar, gelatin, pectin and sweeteners. These liquids are solidified into solid tablets or caplets by freeze drying and solid state extraction techniques. The drug compounds may be compressed with viscoelastic and thermoelastic sugars and polymers or effervescent components to produce porous matrices intended for immediate release, without the need of water.

Moreover, the compounds of the present disclosure can be administered in the form of nose drops, or metered dose and a nasal or buccal inhaler. The drug is delivered from a nasal solution as a fine mist or from a powder as an aerosol.

As regards these applications, the present method includes the administration to an animal, particularly a mammal, and more particularly a human, of a therapeutically effective amount of the compound effective in the inhibition of S-adenosylmethionine decarboxylase, or the inhibition of a parasitic infection or the inhibition of an infection from caused by *Pneumocystis cainii* or of neoplasia and tumor growth.

The foregoing description illustrates and describes the disclosure. Additionally, the disclosure shows and describes only the preferred embodiments but, as mentioned above, it is to be understood that it is capable to use in various other combinations, modifications, and environments and is capable of changes or modifications within the scope of the invention concepts as expressed herein, commensurate with the above teachings and/or the skill or knowledge of the relevant art. The embodiments described herein above are further intended to explain best modes known by applicant and to enable others skilled in the art to utilize the disclosure in such, or other, embodiments and with the various modifications required by the particular applications or uses thereof. Accordingly, the description is not intended to limit the invention to the form disclosed herein. Also, it is intended to the appended claims be construed to include alternative embodiments.

Still other objects and advantages of the present disclosure will become readily apparent by those skilled in the art from the following detailed description, wherein it is shown and described only the preferred embodiments, simply by way of illustration of the best mode. As will be realized, the disclosure is capable of other and different embodiments, and its several details are capable of modifications in various obvious respects, without departing from the disclosure. Accordingly, the description is to be regarded as illustrative in nature and not as restrictive.

All publications and patent applications cited in this specification are herein incorporated by reference, and for any and all purposes, as if each individual publication or patent application were specifically and individually indicated to be incorporated by reference.

REFERENCES (1) Hackert, M. L.; Pegg, A. E. Pyruvoyl-dependent enzymes. In *Comprehensive Biological Catalysis*; Sinnott, M. L., Ed.; Academic Press: London, 1997; pp 201-216.

(2) Pegg, A. E.; Xiong, H.; Feith, D.; Shantz, L. M. S-Adenosylmethionine Decarboxylase: Structure, Function and Regulation by Polyamines. *Biochem. Soc. Trans.,* 1998, 26, 580-586.

(3) Tabor, C. W.; Tabor, H. Polyamines. *Annu. Rev. Biochem.,* 1984, 53, 749-790.

(4) Tabor, C. W.; Tabor, H. Methionine Adenosyltransferase (S-Adenosylmethionine Synthetase) and S-Adenosylmethionine Decarboxylase. *Advan. Enzymol. Related Areas Mol. Biol.,* 1984, 56, 251-282.

(5) van Poelje, P. D.; Snell, E. E. Pyruvoyl-dependent Enzymes. *Ann. Rev. Biochem.,* 1990, 59, 29-59.

(6) Wallace, H. M.; Fraser, A. V.; Hughes, A. A Perspective of Polyamine Metabolism. *Biochem. J.,* 2003, 376, 1-14.

(7) Casero, R. A., Jr.; Celano, P.; Ervin, S. J.; Applegren, N. B.; Wiest, L.; Pegg, A. E. Isolation and Characterization of a cDNA Clone that Codes for Human Spermidine/Spermine N1-acetyltransferase. *J. Biol. Chem.,* 1991, 266, 810-4.

(8) Pegg, A. E. Polyamine Metabolism and its Importance in Neoplastic Growth and as a Target for Chemotherapy. *Cancer Res.,* 1988, 48, 759-774.

(9) Gerner, E. W.; Meyskens, F. L., Jr. Polyamines and Cancer: Old Molecules, New Understanding. *Nat. Rev. Cancer,* 2004, 4, 781-792.

(10) Metcalf, B. W.; Bey, P.; Danzin, C.; Jung, M. J.; Casara, P.; Vevert, J. P. Catalytic Irreversible Inhibition of Mammalian Ornithine Decarboxylase (E C 4 1 1 17) by Substrate and Product Analogs. *J. Amer. Chem. Soc.,* 1978, 100, 2551-2553.

(11) Bewley, M. C.; Graziano, V.; Jiang, J.; Matz, E.; Studier, F. W.; Pegg, A. E.; Coleman, C. S.; Flanagan, J. M. Structures of Wild-type and Mutant Human Spermidine/Spermine N1-Acetyltransferase, a Potential Therapeutic Drug Target. *Proc Natl Acad Sci USA,* 2006, 103, 2063-8.

(12) Alhonen-Hongisto, L.; Seppanen, P.; and Janne, J. Intracellular Putrescine and Spermidine Deprivation Induces Increased Uptake of the Natural Polyamines and Methylglyoxal bis(guanylhydrazone). *Biochem. J.,* 1980, 192, 941-5.

(13) Meyskens, F. L., Jr.; Gerner, E. W. Development of Difluoromethylornithine (DFMO) as a Chemoprevention Agent. *Clin. Cancer Res.,* 1999, 5, 945-51.

(14) Fabian, C. J.; Kimler, B. F.; Brady, D. A.; Mayo, M. S.; Chang, C. H.; Ferraro, J. A.; Zalles, C. M.; Stanton, A. L.; Masood, S.; Grizzle, W. E.; Boyd, N. F.; Arneson, D. W.; Johnson, K. A. A Phase II Breast Cancer Chemoprevention Trial of Oral Alpha-difluoromethylornithine: Breast Tissue, Imaging, and Serum and Urine Biomarkers. *Clin. Cancer Res.,* 2002, 8, 3105-17.

(15) Basuroy, U. K.; Gerner, E. W. Emerging Concepts in Targeting the Polyamine Metabolic Pathway in Epithelial Cancer Chemoprevention and Chemotherapy. *J. Biochem. (Tokyo),* 2006, 139, 27-33.

(16) Williams-Ashman, H. G.; Schenone, A. Methylglyoxal bis(guanylhydrazone) as a Potent Inhibitor of Mammalian and Yeast S-adenosylmethionine Decarboxylases. *Biochem. Biophys. Res. Commun.,* 1972, 46, 288-295.

(17) Millward, M. J.; Joshua, A.; Kefford, R.; Aamdal, S.; Thomson, D.; Hersey, P.; Toner, G.; Lynch, K. Multicentre Phase II Trial of the Polyamine Synthesis Inhibitor SAM486A (CGP48664) in Patients with Metastatic Melanoma. *Invest. New Drugs,* 2005, 23, 253-6.

(18) Shantz, L. M.; Stanley, B. A.; Secrist, J. A., III; and Pegg, A. E. Purification of Human S-adenosylmethionine Decarboxylase Expressed in *Escherichia coli* and Use of this Protein to Investigate the Mechanism of Inhibition by the Irreversible Inhibitors, 5'-Deoxy-5'-[(3-hydrazinopropyl)methylamino]adenosine and 5'{[(Z)-4-Amino-2-butenyl]methylamino-5'-deoxyadenosine. *Biochemistry,* 1992, 31, 6848-6855.

(19) Danzin, C.; Marchal, P.; Casara, P. Irreversible Inhibition of Rat S-Adenosylmethionine Decarboxylase by 5'-{[(Z)-4-Amino-2-butenyl]methylamino}-5'-deoxyadenosine. *Biochem. Pharmacol.,* 1990, 40, 1499-1503.

(20) Ekstrom, J. E.; Matthews, I. I.; Stanley, B. A.; Pegg, A. E.; Ealick, S. E. The Crystal Structure of Human S-Adenosylmethionine Decarboxylase at 2.25 Å Resolution Reveals a Novel Fold. *Structure,* 1999, 7, 583-595.

(21) Tolbert, W. D.; Zhang, Y.; Cottet, S. E.; Bennett, E. M.; Ekstrom, J. L.; Pegg, A. E.; Ealick, S. E. Mechanism of Human S-Adenosylmethionine Decarboxylase Proenzyme Processing as Revealed by the Structure of the S68A Mutant. *Biochemistry,* 2003, 42, 2386-95.

(22) Ekstrom, J. L.; Tolbert, W. D.; Xiong, H.; Pegg, A. E.; Ealick, S. E. Structure of a human S-Adenosylmethionine Decarboxylase Self-processing Ester Intermediate and Mechanism of Putrescine Stimulation of Processing as Revealed by the H243A Mutant. *Biochemistry,* 2001, 40, 9495-9504.

(23) Tolbert, D. W.; Ekstrom, J. L.; Mathews, I. I.; Secrist, J. A., III; Kapoor, P.; Pegg, A. E.; Ealick, S. E. The Structural Basis for Substrate Specificity and Inhibition of Human S-Adenosylmethionine Decarboxylase. *Biochemistry,* 2001, 40, 9484-9494.

(24) Otwinowski, Z.; Minor, W. Processing of X-Ray Diffraction Data Collected in Oscillation Mode. *Methods Enzymol.,* 1997, 276, 307-326.

(25) Brünger, A. T.; Adams, P. D.; Clore, G. M.; DeLano, W. L.; Gros, P.; Grosse-Kunstleve, R. W.; Jiang, J. S.; Kuszewski, J.; Nilges, M.; Pannu, N. S.; Read, R. J.; Rice, L. M.; Simonson, T.; Warren, G. L. Crystallography & NMR System: A New Software Suite for Macromolecular Structure Determination. *Acta Crystallogr.,* 1998, D 54, 905-21.

(26) Jones, T. A.; Zou, J.-Y.; Cowan, S. W.; Kjeldgaard, M. Improved Methods for the Building of Protein Models in Electron Density Maps and the Location of Errors in These Models. *Acta Crystallogr.,* 1991, A 47, 110-119.

(27) Emsley, P.; Cowtan, K. Coot: Model-Building Tools for Molecular Graphics. *Acta Crystallogr D Biol Crystallogr.,* 2004, 60, 2126-32.

(28) Kleywegt, G. J.; Jones, T. A. Databases in Protein Crystallography. *Acta Crystallogr D Biol Crystallogr.,* 1998, 54, 1119-31.

(29) Mohamadi, F.; Richards, N. G. J.; Guida, W. C.; Liskamp, R.; Lipton, M.; Caufield, C.; Chang, G.; Hendrickson, T.; Still, W. C. Macromodel—an Integrated Software System for Modeling Organic and Bioorganic Molecules Using Molecular Mechanics. *Journal of Computational Chemistry,* 1990, 11, 440-467. Macro-Model is distributed by Schrödinger, L.L.C, New York, N.Y.

(30) Chang, G.; Guida, W. C.; Still, W. C. An Internal Coordinate Monte-Carlo Method for Searching Conformational Space. *J. Amer. Chem. Soc.,* 1989, 111, 4379-4386.

(31) Kolossavary, I.; Guida, W. C. Low-Mode Conformational Search Elucidated: Application to C39H80 and Flexible Docking of 9-Deazaguanine Inhibitors into PNP. *Journal of Computational Chemistry,* 1999, 20, 1671-1684.

(32) Weiner, S. J.; Kollman, P. A.; Case, D. A.; Singh, U. C.; Ghio, C.; Alagona, G.; Profeta, S.; Weiner, P. A New Force-Field for Molecular Mechanical Simulation of Nucleic-Acids and Proteins. *J. Amer. Chem. Soc.,* 1984, 106, 765-784.

(33) Weiner, S. J.; Kollman, P. A.; Nguyen, D. T.; Case, D. A. An All Atom Force-Field for Simulations of Proteins and Nucleic-Acids. *Journal of Computational Chemistry,* 1986, 7, 230-252.

(34) Ponder, J. W.; Richards, F. M. An Efficient Newton-Like Method for Molecular Mechanics Energy Minimization of Large Molecules. *Journal of Computational Chemistry,* 1987, 8, 1016-1024.

(35) Markham, G. D.; Norrby, P. O.; Bock, C. W. S-Adenosylmethionine Conformations in Solution and in Protein Complexes: Conformational Influences of the Sulfonium Group. *Biochemistry,* 2002, 41, 7636-46.

(36) Shantz, L. M.; Pegg, A. E. (1998) Assay of S-Adenosylmethionine Decarboxylase, in *Methods in Molecular Biology, Vol 79: Polyamine Protocols*; Morgan, D. M. L., Ed.; Humana Press Inc.: New Jersey, 1998; pp 45-50.

(37) Secrist, J. A., III. New Substrate Analogues as Inhibitors of S-Adenosylmethionine Decarboxylase. *Nucleosides Nucleotides,* 1987, 6, 73-83.

(38) Mitsunobu, O. The Use of Diethyl Azodicarbonylate and Triphenylphosphine in Synthesis and Transformation of Natural Products. *Synthesis,* 1981, 1-28.

(39) Ikehara, M.; Uesugi, S.; Kaneko, M. Bromination of Adenine Nucleoside and Nucleotide. *Chem. Comm.,* 1967, 17-18.

(40) Van Aerschot, A. A.; Mamos, P.; Weyns, N. J.; Ikeda, S.; De Clercq, E.; Herdewijn, P. A. Antiviral activity of C-Alkylated Purine Nucleosides Obtained by Cross-Coupling with Tetraalkyltin Reagents. *J. Med. Chem.,* 1993, 36, 2938-2942.

(41) (a) Long, R. A.; Robins, R. K.; Townsend, L. B. Purine Nucleosides. XV. The Synthesis of 8-Amino- and 8-Substituted Aminopurine Nucleosides. *J. Org. Chem.,* 1967, 32, 2751-2756; (b) Reese, C. B.; Chattopadhyaya, J. B. Reactions Between 8-Bromoadenosine and Amines. Chemistry of 8-Hydrazinoadenosine. *Synthesis,* 1977, 725-726.

(42) Kohyama, N.; Katashima, T.; Yamamoto, Y. Synthesis of Novel 2-Aryl AICAR Derivatives. *Synthesis,* 2004, 2799-2804.

(43) (a) Borchardt, R. T.; Huber, J. A.; Wu, Y. S. *J. Org. Chem.,* 1976, 41, 565-567. (b) van Tilburg, E. W.; von Frijtag Drabbe Künzel, J. K.; de Groote, M.; Vollinga, R. C.; Lorenzen, A.; IJzerman, A. P. $N^6$,5'-Disubstituted Adenosine derivatives as Partial Agonists for the Human Adenosine $A_3$ Receptor. *J. Med. Chem.,* 1999, 42, 1393-1400.

(44) Gani, D.; Johnson, A. W. The Base-Sugar Conformation of Certain Derivatives of Adenosine. *J. Chem. Soc. Perkin Trans.* 1, 1982, 1197-1204.

(45) Kuhn, R.; Jahn, W. Vom Adenosin abgeleitete Thioäther and S-Oxide, *Chem. Ber.,* 1965, 98, 1699-1704.

(46) Schmidt, R. R.; Schloz, U.; Schwille, D. Synthese 5'-modifizierter Adenosinderivate. *Chem. Ber.,* 1968, 101, 590-594.

(47) Minnick, A. A.; Kenyon, G. L. General Synthetic Approach to Stable Nitrogen Analogs of S-Adenosylmethionine. *J. Org. Chem.,* 1988, 53, 4952-4961.

(48) Khomutov, A. R.; Vepsalainen, J. J.; Shvetsov, A. S.; Hyvonen, T.; Keinanen, T. A.; Pustobaev, V. N.; Eloranta, T. O.; Khomutov, R. M. Synthesis of Hydroxylamine Analogues of Polyamines. *Tetrahedron,* 1996, 52, 13751-13766.

(49) Webb, R. R.; Kaneko, T. Synthesis of 1-(aminooxy)-4-[(3-nitro-2-pyridyl)dithio]butane and 1-(Aminooxy)-4-[3-nitro-2-pyridyl)dithio]but-2-ene, Novel Heterobifunctional Cross-Linking Reagents. *Bioconjugate Chem.,* 1990, 1, 96-99.

(50) Kucznierz, R; Grams, F.; Leinert, H.; Marzenell, K.; Engh, R. A.; von der Saal, W. Tetrahydro-isoquinoline-Based Factor Xa Inhibitors. *J. Med. Chem.,* 1998, 41, 4983-4994.

(51) Pankaskie, M.; Abdel-Monem, M. M. Inhibitors of Polyamine Biosynthesis. 8. Irreversible Inhibition of Mammalian S-Adenosyl-L-methionine Decarboxylase by Substrate Analogues. *J. Med. Chem.,* 1980, 23, 121-127.

(52) Tavale, S. S.; Sobell, H. M. Crystal and Molecular Structure of 8-Bromoguanosine and 8-Bromoadenosine, Two Purine Nucleosides in the Syn Conformation. *J Mol Biol.,* 1970, 48, 109-23.

(53) Ikehara, M.; Uesugi, S.; Yoshida, K. Studies on the Conformation of Purine Nucleosides and Their 5'-Phosphates. *Biochemistry*, 1972, 11, 830-6.
(54) Takenaka, H.; Ikehara, M.; Tonomura, Y. Interaction Between Actomyosin and 8-Substituted ATP Analogs. *Proc Natl Acad Sci USA*, 1978, 75, 4229-33.
(55) Stolarski, R.; Hagberg, C. E.; Shugar, D. Studies on the Dynamic Syn-Anti Equilibrium in Purine Nucleosides and Nucleotides with the Aid of 1H and 13C NMR Spectroscopy. *Eur J Biochem*, 1984, 138, 187-92.
(56) Secrist, J. A., III. New Substrate Analogues as Inhibitors of S-Adenosylmethionine Decarboxylase. *Nucleosides Nucleotides*, 1987, 6, 73-84.
(57) Pegg, A. E.; Jones, D. B.; Secrist, J. A., III. Effect of Inhibitors of S-Adenosylmethionine Decarboxylase on Polyamine Content and Growth of L1210 Cells. *Biochemistry*, 1988, 27, 1408-1415.
(58) Kolb, M.; Danzin, C.; Barth, J.; Calverie, N. Synthesis and Biochemical Properties of Chemically Stable Product Analogues of the Reaction Catalyzed By S-Adenosylmethionine Decarboxylase. *J. Med. Chem.*, 1982, 25, 550-556.
(59) Sinnokrot, M. O.; Valeev, E. F.; Sherrill, C. D. Estimates of the ab initio limit for pi-pi interactions: The benzene dimer. *J. Amer. Chem. Soc.*, 2002, 124, 10887-10893.

What is claimed is:
1. A compound represented by the formula;

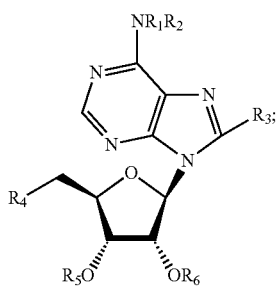

pharmaceutically acceptable salt thereof; and solvate thereof; wherein each of $R_1$ and $R_2$ individually is selected from the group consisting of H and alkyl; $R_4$ is selected from the group consisting of $NR_7R_8$; each of $R_7$ and $R_8$ individually is selected from the group consisting of alkyl, $(CH_2)_n NR_1R_2$, $(CH_2)_n CONR_1R_2$ and $(CH_2)_n C=ONR_1R_2$; wherein n is a whole number integer from 1 to 8; each of $R_5$ and $R_6$ individually is selected from the group consisting of H and acyl; and wherein $R_3$ is alkyl.

2. The compound according to claim 1 wherein each $R_1$ and $R_2$ is H.

3. The compound according to claim 1 wherein each $R_5$ and $R_6$ is H.

4. The compound according to claim 1 wherein $R_3$ is methyl.

5. A pharmaceutical composition comprising an effective amount of a compound or pharmaceutically acceptable salt thereof, or solvate thereof, according to claim 1, and a pharmaceutically acceptable carrier.

6. A method of treating a host suffering from a parasitic infection or an infection from caused by *Pneumocystis cainii* which comprises administering to said host an effective amount of a compound; pharmaceutically acceptable salt thereof or solvate thereof, according to claim 1.

7. The method according to claim 6 wherein said infection is a protozoal infection.

8. The method according to claim 7 wherein said infection is trypanosomiasis or malaria.

9. A pharmaceutical composition comprising an effective amount of a compound or pharmaceutically acceptable salt thereof, or a solvate thereof, according to claim 2, and a pharmaceutically acceptable carrier.

10. A pharmaceutical composition comprising an effective amount of a compound or pharmaceutically acceptable salt thereof, or a solvate thereof, according to claim 3, and a pharmaceutically acceptable carrier.

11. A pharmaceutical composition comprising an effective amount of a compound or pharmaceutically acceptable salt thereof, or a solvate thereof, according to claim 1, and a pharmaceutically acceptable carrier.

12. A pharmaceutical composition comprising an effective amount of a compound or pharmaceutically acceptable salt thereof, or a solvate thereof, according to claim 4, and a pharmaceutically acceptable carrier.

13. A method for inhibiting S-adenosylmethionine decarboxylase in a host in need thereof which comprises administering to said host an effective amount of a compound; pharmaceutically acceptable salt thereof or solvate thereof, according to claim 2.

14. A method for inhibiting S-adenosylmethionine decarboxylase in a host in need thereof which comprises administering to said host an effective amount of a compound; pharmaceutically acceptable salt thereof or solvate thereof, according to claim 3.

15. A method for inhibiting S-adenosylmethionine decarboxylase in a host in need thereof which comprises administering to said host an effective amount of a compound; pharmaceutically acceptable salt thereof or solvate thereof, according to claim 1.

16. A method for inhibiting S-adenosylmethionine decarboxylase in a host in need thereof which comprises administering to said host an effective amount of a compound; pharmaceutically acceptable salt thereof or solvate thereof, according to claim 4.

17. A method of treating a host suffering from a parasitic infection or an infection from caused by *Pneumocystis cainii* which comprises administering to said host an effective amount of a compound; pharmaceutically acceptable salt thereof or solvate thereof, according to claim 2.

18. A method of treating a host suffering from a parasitic infection or an infection from caused by *Pneumocystis cainii* which comprises administering to said host an effective amount of a compound; pharmaceutically acceptable salt thereof or solvate thereof, according to claim 3.

19. A method of treating a host suffering from a parasitic infection or an infection from caused by *Pneumocystis cainii* which comprises administering to said host an effective amount of a compound; pharmaceutically acceptable salt thereof or solvate thereof, according to claim 4.

* * * * *